US010626106B2

(12) United States Patent
Jakob et al.

(10) Patent No.: US 10,626,106 B2
(45) Date of Patent: Apr. 21, 2020

(54) SUBSTITUTED PYRROLIDINE AMIDES I

(71) Applicant: Gruenenthal GmbH, Aachen (DE)

(72) Inventors: Florian Jakob, Aachen (DE); Jo Alen, Vliermaal (BE); Sebastian Krüger, Aachen (DE); Markus Schade, Aachen (DE); Daniela Friebe, Aachen (DE); Stephanie Hennen, Aachen (DE)

(73) Assignee: GRUENENTHAL GMBH, Aachen (DE)

( * ) Notice: Subject to any disclaimer, the term of this patent is extended or adjusted under 35 U.S.C. 154(b) by 0 days.

(21) Appl. No.: 16/223,845

(22) Filed: Dec. 18, 2018

(65) Prior Publication Data

US 2019/0185455 A1 Jun. 20, 2019

(30) Foreign Application Priority Data

Dec. 18, 2017 (EP) ..................................... 17208175

(51) Int. Cl.
| | | |
|---|---|---|
| A61K 31/437 | (2006.01) | |
| A61K 31/416 | (2006.01) | |
| C07D 401/14 | (2006.01) | |
| C07D 403/14 | (2006.01) | |
| A61P 29/00 | (2006.01) | |
| C07D 405/14 | (2006.01) | |
| A61P 25/00 | (2006.01) | |
| C07D 417/14 | (2006.01) | |
| A61P 19/02 | (2006.01) | |
| A61P 11/06 | (2006.01) | |
| C07D 413/14 | (2006.01) | |

(52) U.S. Cl.
CPC ............ C07D 401/14 (2013.01); A61P 11/06 (2018.01); A61P 19/02 (2018.01); A61P 25/00 (2018.01); A61P 29/00 (2018.01); C07D 403/14 (2013.01); C07D 405/14 (2013.01); C07D 413/14 (2013.01); C07D 417/14 (2013.01)

(58) Field of Classification Search
None
See application file for complete search history.

(56) References Cited

U.S. PATENT DOCUMENTS

2019/0185470 A1 6/2019 Jakob et al.

FOREIGN PATENT DOCUMENTS

| WO | 2006108699 A1 | 10/2006 |
| WO | 2007122165 A1 | 11/2007 |
| WO | 2008043789 A1 | 4/2008 |
| WO | 2008063116 A1 | 5/2008 |
| WO | 2002076048 A1 | 6/2008 |
| WO | 2009035067 A1 | 3/2009 |
| WO | 2009142569 A1 | 11/2009 |
| WO | 2009142571 A1 | 11/2009 |
| WO | 2015099196 A1 | 7/2015 |
| WO | 2016046260 A1 | 3/2016 |
| WO | 2017034006 A1 | 3/2017 |

OTHER PUBLICATIONS

Hapgood, et al., "Glucocorticoid-independent modulation of GR activity: Implications for immunotherapy", Elsevier, Pharmacology & Therapeutics, 165, pp. 93-113, 2016.
Buttgereit, et al., "Novel glucocorticoids: where are we now and where do we want to go?", Clinical and Experimental Rheumatology, 33, pp. 29-33, 2015.
Hartmann, et al., "Molecular Actions of Glucocorticoids in Cartilage and Bone During Health Disease, and Steroid Therapy", American Physiological Society, Physiol Rev, 96, pp. 409-447, 2016.
De Bosscher, et al., "Actovation of the Glucocorticoid Receptor in Acute Inflamation: the SEDIGRAM Concept", Trends in Pharmacological Sciences, vol. 37, No. 1, pp. 4-16, Jan. 2016.
Buttgereit, et al., "Polymylagia Rheumatica and Giant Cell Arteritis: A Systematic Review", JAMA, 315 (22), pp. 2442-2458, 2016.
Liu, et al., "A practical guide to the monitoring and management of the complications of systemic corticosteroid therapy", Allergy, Asthma & Clinical Immunology, pp. 1-25, 2013.
Senra, et al., "Recent Progress in Transition-Metal- Catalyzed C-N Cross-Couplings: Emerging Approaches Towards Sustainability", Current Organic Synthesis, 8, pp. 53-78, 2011.
Ruiz-Castillo, et al., "Applications of Palladium-Catalyzed C-N Cross-Coupling Reactions", Chemical Reviews, 116, pp. 12564-12649, 2016.
Sambiagio, et al., "Copper catalysed Ullmann type chemistry: from mechanistic aspects to modern development", Chem. Soc. Rev., 43, pp. 3525-3550, 2014.

(Continued)

*Primary Examiner* — Samantha L Shterengarts
(74) *Attorney, Agent, or Firm* — Norris McLaughlin, P.A.

(57) ABSTRACT

The invention relates to compounds according to general formula (I),

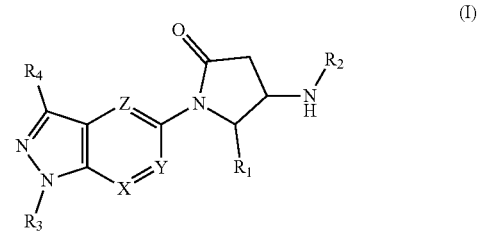

which act as modulators of the glucocorticoid receptor and can be used in the treatment and/or prophylaxis of disorders which are at least partially mediated by the glucocorticoid receptor.

15 Claims, No Drawings

(56) References Cited

OTHER PUBLICATIONS

Surry, et al., "Diamine ligands in copper-catalysed reactions", Chemical Science, 1, pp. 13-31, 2010.
Surry, et al., "Dialkylbiaryl phosphines in PD-catalyzed amination: a user's guide", Chemical Science, 2, pp. 27-50, 2011.
Klapars, et al., "A General and Efficient Copper Catalyst for the Amidation of Aryl Halides and the N-Arylation of Nitrogen Heterocycles", Journal of American Chemical Society, 123, pp. 7727-7729, 2001.
March, et al., "Attack by Nitrogen at an Acyl Carbon", Chapter 16, E, Acyl Substitution Reactions, pp. 1427-1473.
Greene, et al., "Protection for the Amino Group", Protective Groups in Organic Synthesis, Third Edition, pp. 494-653, 1999.
Bisol, et al., "Nucleophilic Ring-Opening of Epoxide and Aziridine Acetates for the Stereodivergent Synthesis of B-Hydroxy and B-Amino y-Lactams", Journal of Organic Chemistry, 76, pp. 948-962, 2011.
Pohmakotr, et al., "Highly Diasteroselective Synthesis of B-Carboxy-y-lactams adn Their Ethyl Esters via Sc(OTf)3-Catalyzed Imino Mukaiyama-Aldol Type Reaction of 2,5-Bis(trimethylsilyloxy)furan with Imines", Journal of Organic Chemistry, 72, pp. 5016-5019, 2007.
Wei, et al., "Diasteroselective Synthesis of y-Lactams by a One-Pot, Four-Component Reaction", Organic Letters, vol. 9, No. 20, pp. 4077-4080, 2007.
Biggs-Houck, et al., "Carbon-Carbon Bond-Forming Reactions of a-Thioaryl Carbonyl Compounds for the Synthesis of Complex Heterocyclic Molecules", Journal of Organic Chemistry, 77, pp. 160-172, 2012.
Ma, et al., "A modified Curtis reaction: an efficient and simple method for direct isolation of free amine", Elsevier, Tetrahedron Letters, 51, pp. 385-386, 2010.
Pelletier, et al., "Nitro-Mannich/Lactamization Cascades for the Direct Stereoselective Synthesis of Pyrrolidin-2-ones", Organic Letters, vol. 11, No. 20, pp. 4512-4515, 2009.
Bianchi, et al., "Aquivion PFSA as a Novel Solid and Reusable Acid Catalyst in the Synthesis of 2-Pyrrolidin-2-ones in Flow", ACS Sustainable Chemistry Engineering, 3, pp. 1873-1880, 2015.
March, et al., "The Reduction of Nitriles to Aldehydes", Chapter 19, Reductions, pp. 1815-1844.
Liu, et al., "Studies on the Synthesis of Bioactives of 4-Amino Derivatives of Tetramic Acid", Journal of Heterocyclic Chem., 51, pp. E25-E33, 2014.
March, et al., "E. Hydrogen on Both Sides", Chapter 15, Reactions in Which Hydrogen Adds to One Side, pp. 1053-1247.
March, et al., "B. Attack at Non-Carbonyl Multiple-Bonded Heteroatoms", Chapter 19, Reductions, pp. 1811-1869.
Diad, et al., "Copper-Prompted Carbon-Heteroatom Bond Cross-Coupling with Boronic Acids and Derivatives", Synthesis, No. 6, pp. 829-856, 2011, NY, USA.
Fischer, et al., "Palladium- and copper-mediated N-aryl bond formation reactions for the synthesis of biological active compounds", Beilstein Journal of Organic Chemistry, 7, pp. 59-73, 2011.
Antilla, et al., "Copper-Diamine-Catalyzed N-Arylation of Pyrroles, Pyrazoles, Indazoles, Imidazoles and Triazoles", Journal of American Chemical Society, 69, pp. 5578-5587, 2004.

SUBSTITUTED PYRROLIDINE AMIDES I

This application claims foreign priority benefit of European Application No. 17 208 175.4, filed Dec. 18, 2017, the disclosure of which patent application is incorporated herein by reference The invention relates to compounds according to general formula (I)

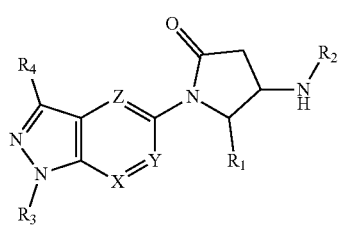

which act as modulators of the glucocorticoid receptor and can be used in the treatment and/or prophylaxis of disorders which are at least partially mediated by the glucocorticoid receptor.

Glucocorticoids (GC) exert strong anti-inflammatory, immunosuppressive and disease-modifying therapeutic effects mediated by the glucocorticoid receptor (GR). They have been widely used to treat inflammatory and immune diseases for decades and still represent the most effective therapy in those conditions. However, chronic GC treatment of inflammatory diseases such as asthma, rheumatoid arthritis, inflammatory bowel disease, chronic obstructive pulmonary disease, acute respiratory distress syndrome, cystic fibrosis, osteoarthritis, polymyalgia rheumatica and giant cell arteritis is hampered by GC-associated adverse effects. These undesired side effects include insulin resistance, diabetes, hypertension, glaucoma, depression, osteoporosis, adrenal suppression and muscle wasting with osteoporosis and diabetes being the most severe ones from the physician's point of view (Hapgood J P. et al., Pharmacol Ther. 2016 September; 165: 93-113; Buttgereit F. et al, Clin Exp Rheumatol. 2015 July-August; 33(4 Suppl 92):S29-33; Hartmann K. et al, Physiol Rev. 2016 April; 96(2):409-47).

One example of an oral glucocorticoid is prednisone which is frequently prescribed for the treatment of several inflammatory disorders (De Bosscher K et al., Trends Pharmacol Sci. 2016 January; 37(1):4-16; Buttgereit F. et al., JAMA. 2016; 315(22):2442-2458). As GC cause adrenal suppression, prednisolone withdrawal symptoms can be severe if the drug is discontinued abruptly when all the signs of the disease have disappeared. Thus gradual GC tapering to physiological doses is frequently part of treatment protocols to reduce the risk of relapse and other withdrawal symptoms (Liu D. et al., Allergy Asthma Clin Immunol. 2013 Aug. 15; 9(1):30). Therefore, there is high medical need for novel potent anti-inflammatory drugs with less adverse effects.

Recent research has focused on the development of partial agonists or selective glucocorticoid receptor modulators which activate the pathways for the inhibition of inflammation but avoid targeting the pathways that lead to the GC-associated adverse effects. Most of these effects have been demonstrated to be mediated by different GR-dependent genomic mechanisms termed transactivation and transrepression. The anti-inflammatory actions of GC are mainly attributable to the transrepression of inflammatory genes while certain side effects are predominantly mediated via transactivation of several genes. According to the nature of a ligand the GR can be selectively modulated in a specific conformation which favors transrepression over transactivation resulting in an improved therapeutic benefit (De Bosscher K et al., Trends Pharmacol Sci. 2016 January; 37(1):4-16). The concept of such dissociating ligands was already defined about two decades ago and several compounds have been identified and were evaluated in preclinical and clinical testing but none of them has as yet been approved for clinical use.

Compounds which are active as modulators of the glucocorticoid receptor are also known e.g. from WO 2007/122165, WO 2008/076048 and WO 2008/043789, WO 2009/035067, WO 2009/142571, WO 2016/046260, and WO 2017/034006.

It was an object of the invention to provide novel compounds which are modulators of the glucocorticoid receptor and which preferably have advantages over the compounds of the prior art. The novel compounds should in particular be suitable for use in the treatment and/or prophylaxis of disorders or diseases which are at least partially mediated by the glucocorticoid receptor.

This object has been achieved by the subject-matter as described herein.

It was surprisingly found that the compounds according to the invention are highly potent modulators of the glucocorticoid receptor.

The invention relates to a compound according to general formula (I),

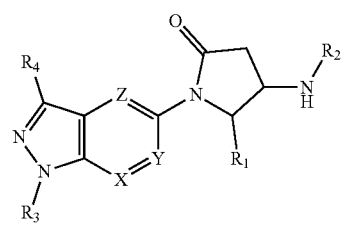

wherein
$R_1$ represents —$C_{1-10}$-alkyl; —$C_{3-10}$-cycloalkyl; —$C_{1-6}$-alkylene-$C_{3-10}$-cycloalkyl; 3 to 7 membered heterocycloalkyl; —$C_{1-6}$-alkylene-(3 to 7 membered heterocycloalkyl); aryl; —$C_{1-6}$-alkylene-aryl; 5 or 6-membered heteroaryl; or —$C_{1-6}$-alkylene-(5 or 6-membered heteroaryl);
$R_2$ represents —C(=O)—$C_{1-10}$-alkyl; —C(=O)—$C_{3-10}$-cycloalkyl; —C(=O)—$C_{1-6}$-alkylene-$C_{3-10}$-cycloalkyl; —C(=O)-(3 to 7 membered heterocycloalkyl); —C(=O)—$C_{1-6}$-alkylene-(3 to 7 membered heterocycloalkyl); —C(=O)-aryl; —C(=O)—$C_{1-6}$-alkylene-aryl; —C(=O)-(5 or 6-membered heteroaryl); —C(=O)—$C_{1-6}$-alkylene-(5 or 6-membered heteroaryl); —S(=O)$_{1-2}$—$C_{1-10}$-alkyl; —S(=O)$_{1-2}$—$C_{3-10}$-cycloalkyl; —S(=O)$_{1-2}$—$C_{1-6}$-alkylene-$C_{3-10}$-cycloalkyl; —S(=O)$_{1-2}$-(3 to 7 membered heterocycloalkyl); —S(=O)$_{1-2}$—$C_{1-6}$-alkylene-(3 to 7 membered heterocycloalkyl); —S(=O)$_{1-2}$-aryl; —S(=O)$_{1-2}$—$C_{1-6}$-alkylene-aryl; —S(=O)$_{1-2}$-(5 or 6-membered heteroaryl); or —S(=O)$_{1-2}$—$C_{1-6}$-alkylene-(5 or 6-membered heteroaryl);
$R_3$ represents 3 to 7 membered heterocycloalkyl; —$C_{1-6}$-alkylene-(3 to 7 membered heterocycloalkyl); 5 or 6-membered heteroaryl; —$C_{1-6}$-alkylene-(5 or 6-membered heteroaryl); —C(=O)-(3 to 7 membered heterocycloalkyl); —C(=O)—$C_{1-6}$-alkylene-(3 to 7 membered heterocycloalkyl); —C(=O)-(5 or 6-membered heteroaryl); —C(=O)—$C_{1-6}$-alkylene-(5 or 6-membered heteroaryl); —S(=O)$_{1-2}$-(3 to 7 membered heterocycloalkyl); —S(=O)$_{1-2}$—$C_{1-6}$-alkylene-(3 to 7 membered heterocycloalkyl); —S(=O)$_{1-2}$-(5 or 6-membered heteroaryl); or —S(=O)$_{1-2}$—$C_{1-6}$-alkylene-(5 or 6-membered heteroaryl);

$R_4$ represents —H; —F; —Cl; —Br; —I; —CN; —$CF_3$; —$CF_2H$; —$CFH_2$ or cyclopropyl;

X represents N or $CR_5$; wherein $R_5$ represents —H; —F; —Cl; —Br; —I; —CN; —$C_{1-10}$-alkyl or —$C_{3-10}$-cycloalkyl;

Y represents N or $CR_6$; wherein $R_6$ represents —H; —F; —Cl; —Br; —I; —CN; —$C_{1-10}$-alkyl or —$C_{3-10}$-cycloalkyl;

Z represents N or $CR_7$; wherein $R_7$ represents —H; —F; —Cl; —Br; —I; —CN; —$C_{1-10}$-alkyl or —$C_{3-10}$-cycloalkyl;

wherein —$C_{1-10}$-alkyl, —$C_{1-4}$-alkyl and —$C_{1-6}$-alkylene- in each case independently from one another is linear or branched, saturated or unsaturated;

wherein —$C_{1-10}$-alkyl, —$C_{1-4}$-alkyl, —$C_{1-6}$-alkylene-, —$C_{3-10}$-cycloalkyl and 3 to 7 membered heterocycloalkyl in each case independently from one another are unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —C(=O)—$C_{1-6}$-alkyl; —C(=O)—OH; —C(=O)—$OC_{1-6}$-alkyl; —C(=O)—$NH_2$; —C(=O)—NH($C_{1-6}$-alkyl); —C(=O)—N($C_{1-6}$-alkyl)$_2$; —OH; =O; —$OCF_3$; —$OCF_2H$; —$OCFH_2$; —$OCF_2Cl$; —$OCFCl_2$; —O—$C_{1-6}$-alkyl; —O—C(=O)—$C_{1-6}$-alkyl; —O—C(=O)—O—$C_{1-6}$-alkyl; —O—(CO)—NH($C_{1-6}$-alkyl); —O—C(=O)—N($C_{1-6}$-alkyl)$_2$; —O—S(=O)$_2$—$NH_2$; —O—S(=O)$_2$—NH($C_{1-6}$-alkyl); —O—S(=O)$_2$—N($C_{1-6}$-alkyl)$_2$; —$NH_2$; —NH($C_{1-6}$-alkyl); —N($C_{1-6}$-alkyl)$_2$; —NH—C(=O)—$C_{1-6}$-alkyl; —NH—C(=O)—O—$C_{1-6}$-alkyl; —NH—C(=O)—$NH_2$; —NH—C(=O)—NH($C_{1-6}$-alkyl); —NH—C(=O)—N($C_{1-6}$-alkyl)$_2$; —N($C_{1-6}$-alkyl)-C (=O)—$C_{1-6}$-alkyl; —N($C_{1-6}$-alkyl)-C(=O)—O—$C_{1-6}$-alkyl; —N($C_{1-6}$-alkyl)-C(=O)—$NH_2$; —N($C_{1-6}$-alkyl)-C (=O)—NH($C_{1-6}$-alkyl); —N($C_{1-6}$-alkyl)-C(=O)—N($C_{1-6}$-alkyl)$_2$; —NH—S(=O)$_2$OH; NH—S(=O)$_2$—$C_{1-6}$-alkyl; —NH—S(=O)$_2$—O—$C_{1-6}$-alkyl; —NH—S(=O)$_2$—$NH_2$; —NH—S(=O)$_2$—NH($C_{1-6}$-alkyl); —NH—S(=O)$_2$N($C_{1-6}$-alkyl)$_2$; —N($C_{1-6}$-alkyl)-S(=O)$_2$—OH; —N($C_{1-6}$-alkyl)-S(=O)$_2$—$C_{1-6}$-alkyl; —N($C_{1-6}$-alkyl)-S(=O)$_2$—O—$C_{1-6}$-alkyl; —N($C_{1-6}$-alkyl)-S(=O)$_2$—$NH_2$; —N($C_{1-6}$-alkyl)-S(=O)$_2$—NH($C_{1-6}$-alkyl); —N($C_{1-6}$-alkyl)-S(=O)$_2$—N($C_{1-6}$-alkyl)$_2$; —$SCF_3$; —$SCF_2H$; —$SCFH_2$; —S—$C_{1-6}$-alkyl; —S(=O)—$C_{1-6}$-alkyl; —S(=O)$_2$—$C_{1-6}$-alkyl; —S(=O)$_2$—OH; —S(=O)$_2$—O—$C_{1-6}$-alkyl; —S(=O)$_2$—$NH_2$; —S(=O)$_2$—NH($C_{1-6}$-alkyl); —S(=O)$_2$—N($C_{1-6}$-alkyl)$_2$; —$C_{3-6}$-cycloalkyl; 3 to 6-membered heterocycloalkyl; phenyl; 5 or 6-membered heteroaryl; —O—$C_{3-6}$-cycloalkyl; —O-(3 to 6-membered heterocycloalkyl); —O-phenyl; —O-(5 or 6-membered heteroaryl); —C(=O)—$C_{3-6}$-cycloalkyl; —C(=O)-(3 to 6-membered heterocycloalkyl); —C(=O)-phenyl; —C(=O)-(5 or 6-membered heteroaryl); —S(=O)$_2$—($C_{3-6}$-cycloalkyl); —S(=O)$_2$-(3 to 6-membered heterocycloalkyl); —S(=O)$_2$-phenyl or —S(=O)$_2$-(5 or 6-membered heteroaryl);

wherein aryl and 5 or 6-membered heteroaryl in each case independently from one another are unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —$C_{1-4}$-alkylene-$CF_3$; —$C_{1-4}$-alkylene-$CF_2H$; —$C_{1-4}$-alkylene-$CFH_2$; —C(=O)—$C_{1-6}$-alkyl; —C(=O)—OH; —C(=O)—$OC_{1-6}$-alkyl; —C(=O)—NH(OH); —C(=O)—$NH_2$; —C(=O)—NH($C_{1-6}$-alkyl); —C(=O)—N($C_{1-6}$-alkyl)$_2$; —OH; =O; —$OCF_3$; —$OCF_2H$; —$OCFH_2$; —$OCF_2Cl$; —$OCFCl_2$; —O—$C_{1-6}$-alkyl; —O—$C_{3-6}$-cycloalkyl; —O-(3 to 6-membered heterocycloalkyl); —$NH_2$; —NH ($C_{1-6}$-alkyl); —N($C_{1-6}$-alkyl)$_2$; —NH—C(=O)—$C_{1-6}$-alkyl; —N($C_{1-6}$-alkyl)-C(=O)—$C_{1-6}$-alkyl; —NH—C(=O)—$NH_2$; —NH—C(=O)—NH($C_{1-6}$-alkyl); —NH—C(=O)—N($C_{1-6}$-alkyl)$_2$; —N($C_{1-6}$-alkyl)-C(=O)—NH($C_{1-6}$-alkyl); —N($C_{1-6}$-alkyl)-C(=O)—N($C_{1-6}$-alkyl)$_2$; —NH—S(=O)$_2$—$C_{1-6}$-alkyl; —$SCF_3$; —S—$C_{1-6}$-alkyl; —S(=O)—$C_{1-6}$-alkyl; —S(=O)$_2$—$C_{1-6}$-alkyl; —S(=O)$_2$—$NH_2$; —S(=O)$_2$—NH($C_{1-6}$-alkyl); —S(=O)$_2$—N($C_{1-6}$-alkyl)$_2$; —$C_{3-6}$-cycloalkyl; —$C_{1-4}$-alkylene-$C_{3-6}$-cycloalkyl; 3 to 6-membered heterocycloalkyl; —$C_{1-4}$-alkylene-(3 to 6-membered heterocycloalkyl); phenyl or 5 or 6-membered heteroaryl;

in the form of the free compound or a physiologically acceptable salt thereof.

In a preferred embodiment, the compound according to the invention is present in form of the free compound. For the purpose of specification, "free compound" preferably means that the compound according to the invention is not present in form of a salt. Methods to determine whether a chemical substance is present as the free compound or as a salt are known to the skilled artisan such as $^{14}N$ or $^{15}N$ solid state NMR, x-ray diffraction, x-ray powder diffraction, IR, Raman, XPS. $^1H$-NMR recorded in solution may also be used to consider the presence of protonation.

In another preferred embodiment, the compound according to the invention is present in form of a physiologically acceptable salt. For the purposes of this specification, the term "physiologically acceptable salt" preferably refers to a salt obtained from a compound according to the invention and a physiologically acceptable acid or base.

According to the invention, the compound according to the invention may be present in any possible form including solvates, cocrystals and polymorphs. For the purposes of this specification, the term "solvate" preferably refers to an adduct of (i) a compound according to the invention and/or a physiologically acceptable salt thereof with (ii) distinct molecular equivalents of one or more solvents.

Further, the compound according to the invention may be present in form of the racemate, enantiomers, diastereomers, tautomers or any mixtures thereof.

The invention also includes isotopic isomers of a compound of the invention, wherein at least one atom of the compound is replaced by an isotope of the respective atom which is different from the naturally predominantly occurring isotope, as well as any mixtures of isotopic isomers of such a compound. Preferred isotopes are $^2H$ (deuterium), $^3H$ (tritium), $^{13}C$ and $^{14}C$. Isotopic isomers of a compound of the invention can generally be prepared by conventional procedures known to a person skilled in the art.

According to the invention, the terms "—$C_{1-10}$-alkyl", "—$C_{1-8}$-alkyl", "—$C_{1-6}$-alkyl" and "—$C_{1-4}$-alkyl" preferably mean acyclic saturated or unsaturated aliphatic (i.e. non-aromatic) hydrocarbon residues, which can be linear (i.e. unbranched) or branched and which can be unsubstituted or mono- or polysubstituted (e.g. di- or trisubstituted), and which contain 1 to 10 (i.e. 1, 2, 3, 4, 5, 6, 7, 8, 9 or 10), 1 to 8 (i.e. 1, 2, 3, 4, 5, 6, 7 or 8), 1 to 6 (i.e. 1, 2, 3, 4, 5 or 6) and 1 to 4 (i.e. 1, 2, 3 or 4) carbon atoms, respectively. In a preferred embodiment, —$C_{1-10}$-alkyl, —$C_{1-8}$-alkyl, —$C_{1-6}$-alkyl and —$C_{1-4}$-alkyl are saturated. In another preferred embodiment, —$C_{1-10}$-alkyl, —$C_{1-8}$-alkyl, —$C_{1-6}$-alkyl and —$C_{1-4}$-alkyl are not saturated. According to this embodiment, —$C_{1-10}$-alkyl, —$C_{1-8}$-alkyl, —$C_{1-6}$-alkyl and —$C_{1-4}$-alkyl comprise at least one C—C double bond (a C═C-bond) or at least one C—C triple bond (a C≡C-bond). In still another preferred embodiment, —$C_{1-10}$-alkyl, —$C_{1-8}$-alkyl, —$C_{1-6}$-alkyl and —$C_{1-4}$-alkyl are (i) saturated or (ii) not saturated, wherein —$C_{1-10}$-alkyl, —$C_{1-8}$-alkyl, —$C_{1-6}$-alkyl and —$C_{1-4}$-alkyl comprise at least one, preferably one, C—C triple bond (a C≡C-bond).

Preferred —$C_{1-10}$-alkyl groups are selected from methyl, ethyl, ethenyl (vinyl), n-propyl, 2-propyl, 1-propynyl, 2-propynyl, propenyl (—$CH_2CH$═$CH_2$, —CH═CH—$CH_3$, —C(═$CH_2$)—$CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—$CH_2CH$═$CH_2$, —CH═CH—$CH_3$, —C(═$CH_2$)—$CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, n-heptyl, n-octyl, n-nonyl and n-decyl.

Preferred —$C_{1-8}$-alkyl groups are selected from methyl, ethyl, ethenyl (vinyl), n-propyl, 2-propyl, 1-propynyl, 2-propynyl, propenyl (—$CH_2CH$═$CH_2$, —CH═CH—$CH_3$, —C(═$CH_2$)—$CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—$CH_2CH$═$CH_2$, —CH═CH—$CH_3$, —C(═$CH_2$)—$CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, n-heptyl and n-octyl.

Preferred —$C_{1-6}$-alkyl groups are selected from methyl, ethyl, ethenyl (vinyl), n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—$CH_2$—CH═$CH_2$, —CH═CH—$CH_3$, —C(═$CH_2$)—$CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl. Particularly preferred —$C_{1-6}$-alkyl groups are selected from $C_{1-4}$-alkyl groups.

Preferred —$C_{1-4}$-alkyl groups are selected from methyl, ethyl, ethenyl (vinyl), n-propyl, 2-propyl, 1-propynyl, 2-propynyl, propenyl (—$CH_2CH$═$CH_2$, —CH═CH—$CH_3$, —C(═$CH_2$)—$CH_3$), n-butyl, 1-butynyl, 2-butynyl, 1-butenyl, 2-butenyl, isobutyl, sec-butyl, tert-butyl and 3-methylbut-1-ynyl.

Further according to the invention, the terms "—$C_{1-6}$-alkylene-"; "—$C_{1-4}$-alkylene-" and "—$C_1$-2-alkylene-" relate to a linear or branched, preferably linear, and preferably saturated aliphatic residues which are preferably selected from the group consisting of methylene (—$CH_2$—), ethylene (—$CH_2CH_2$—), propylene (—$CH_2CH_2CH_2$— or —C($CH_3$)$_2$—), butylene (—$CH_2CH_2CH_2CH_2$—), pentylene (—$CH_2CH_2CH_2CH_2CH_2$—) and hexylene (—$CH_2CH_2CH_2CH_2CH_2CH_2$—); more preferably methylene (—$CH_2$—) and ethylene (—$CH_2CH_2$—) and most preferably methylene (—$CH_2$—). Preferably, —$C_{1-6}$-alkylene- is selected from —$C_{1-4}$-alkylene-, more preferably from —$C_{1-2}$-alkylene-.

Still further according to the invention, the terms "—$C_{3-10}$-cycloalkyl" and "—$C_{3-6}$-cycloalkyl" preferably mean cyclic aliphatic hydrocarbons containing 3, 4, 5, 6, 7, 8, 9 or 10 carbon atoms and 3, 4, 5 or 6 carbon atoms, respectively, wherein the hydrocarbons in each case can be saturated or unsaturated (but not aromatic), unsubstituted or mono- or polysubstituted.

Preferably, —$C_{3-10}$-cycloalkyl and —$C_{3-6}$-cycloalkyl are saturated. The —$C_{3-10}$-cycloalkyl and —$C_{3-6}$-cycloalkyl can be bound to the respective superordinate general structure via any desired and possible ring member of the cycloalkyl group. The —$C_{3-10}$-cycloalkyl and —$C_{3-6}$-cycloalkyl groups can also be condensed with further saturated, (partially) unsaturated, (hetero)cyclic, aromatic or heteroaromatic ring systems, i.e. with cycloalkyl, heterocyclyl, aryl or heteroaryl residues, which in each case can in turn be unsubstituted or mono- or polysubstituted. Further, —$C_{3-10}$-cycloalkyl and —$C_{3-6}$-cycloalkyl can be singly or multiply bridged such as, for example, in the case of adamantyl, bicyclo[2.2.1]heptyl or bicyclo[2.2.2]octyl. However, preferably, —$C_{3-10}$-cycloalkyl and —$C_{3-6}$-cycloalkyl are neither condensed with further ring systems nor bridged. More preferably, —$C_{3-10}$-cycloalkyl and —$C_{3-6}$-cycloalkyl are neither condensed with further ring systems nor bridged and are saturated. Preferred —$C_{3-10}$-cycloalkyl groups are selected from the group consisting of cyclopropyl, cyclobutyl, cyclopentyl, cyclohexyl, cyclopentenyl, cyclohexenyl, cycloheptyl, cyclooctyl, cyclononyl, cyclodecyl, adamantly, cyclopentenyl, cyclohexenyl, cycloheptenyl, cyclooctenyl, bicyclo[2.2.1]heptyl and bicyclo[2.2.2]octyl. Particularly preferred —$C_{3-10}$-cycloalkyl groups are selected from —$C_{3-6}$-cycloalkyl groups.

Preferred —$C_{3-6}$-cycloalkyl groups are selected from the group consisting of cyclopropyl, cyclobutyl, cyclopentyl, cyclohexyl, cyclopentenyl and cyclohexenyl. Particularly preferred —$C_{3-6}$-cycloalkyl groups are selected from the group consisting of cyclopropyl, cyclobutyl, cyclopentyl and cyclohexyl, most preferably cyclopropyl.

According to the invention, the terms "3 to 7-membered heterocycloalkyl" and "3 to 6-membered heterocycloalkyl" preferably mean heterocycloaliphatic saturated or unsaturated (but not aromatic) residues having 3 to 7, i.e. 3, 4, 5, 6 or 7 ring members and 3 to 6, i.e. 3, 4, 5 or 6 ring members, respectively, wherein in each case at least one, if appropriate also two or three carbon atoms are replaced by a heteroatom or a heteroatom group each selected independently of one another from the group consisting of O, S, S(=O), S(=O)$_2$, N, NH and N($C_{1-4}$-alkyl) such as N(CH$_3$), wherein the carbon atoms of the ring can be unsubstituted or mono- or polysubstituted.

Preferably, 3 to 7-membered heterocycloalkyl and 3 to 6-membered heterocycloalkyl are saturated. The 3 to 7-membered heterocycloalkyl and the 3 to 6-membered heterocycloalkyl groups can also be condensed with further saturated or (partially) unsaturated cycloalkyl or heterocyclyl, aromatic or heteroaromatic ring systems. However, more preferably, 3 to 7-membered heterocycloalkyl and 3 to 6-membered heterocycloalkyl are not condensed with further ring systems. Still more preferably, 3 to 7-membered heterocycloalkyl and 3 to 6-membered heterocycloalkyl are not condensed with further ring systems and are saturated. The 3 to 7-membered heterocycloalkyl and the 3 to 6-membered heterocycloalkyl group can be bound to the superordinate general structure via any desired and possible ring member of the heterocycloaliphatic residue if not indicated otherwise. In a preferred embodiment, 3 to 7-membered heterocycloalkyl and 3 to 6-membered heterocycloalkyl are bound to the superordinate general structure via a carbon atom.

Preferred 3 to 7-membered heterocycloalkyl groups are selected from the group consisting of azepanyl, dioxepanyl, oxazepanyl, diazepanyl, thiazolidinyl, tetrahydrothiophenyl, tetrahydropyridinyl, thiomorpholinyl, tetrahydropyranyl, oxetanyl, oxiranyl, tetrahydrofuranyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, piperazinyl, piperidinyl, pyrazolidinyl, pyranyl; tetrahydropyrrolyl, dihydroquinolinyl, dihydroisoquinolinyl, dihydroindolinyl, dihydroisoindolyl, tetrahydroquinolinyl, tetrahydroisoquinolinyl and tetrahydroindolinyl. Particularly preferred 3 to 7-membered heterocycloalkyl groups are selected from 3 to 6-membered heterocycloalkyl groups.

Preferred 3 to 6-membered heterocycloalkyl groups are selected from the group consisting of tetrahydropyranyl, oxetanyl, oxiranyl, tetrahydrofuranyl, thiazolidinyl, tetrahydrothiophenyl, tetrahydropyridinyl, thiomorpholinyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, piperazinyl, piperidinyl, pyrazolidinyl, pyranyl, tetrahydropyrrolyl, dihydroindolinyl, dihydroisoindolyl and tetrahydroindolinyl. Particularly preferred 3 to 6-membered heterocycloalkyl groups are selected from the group consisting of tetrahydropyranyl, oxetanyl, oxiranyl, and tetrahydrofuranyl.

According to the invention, the term "aryl" preferably means aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted. The aryl can be bound to the superordinate general structure via any desired and possible ring member of the aryl residue. The aryl residues can also be condensed with further saturated or (partially) unsaturated cycloalkyl or heterocycloalkyl, aromatic or heteroaromatic ring systems, which can in turn be unsubstituted or mono- or polysubstituted. In a preferred embodiment, aryl is condensed with a further ring system. Examples of condensed aryl residues are 2H-benzo[b][1,4]oxazin-3(4H)-onyl, 1H-benzo[d]imidazolyl, 2,3-dihydro-1H-indenyl, tetrahydronaphthalenyl, isochroman, 1,3-dihydroisobenzofuranyl, benzodioxolanyl and benzodioxanyl.

Preferably, aryl is selected from the group consisting of phenyl, 1H-benzo[d]imidazolyl, 2H-benzo[b][1,4]oxazin-3 (4H)-onyl, 2,3-dihydro-1H-indenyl, tetrahydronaphthalenyl, isochroman, 1,3-dihydroisobenzofuranyl, 1-naphthyl, 2-naphthyl, fluorenyl and anthracenyl, each of which can be respectively unsubstituted or mono- or polysubstituted. In another preferred embodiment, aryl is not condensed with any further ring system. A particularly preferred aryl is phenyl, unsubstituted or mono- or polysubstituted.

According to the invention, the term "5- to 6-membered heteroaryl" preferably means a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted, if not indicated otherwise. In the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. Preferably, the 5- to 6-membered heteroaryl is bound to the suprordinate general structure via a carbon atom of the heterocycle. The heteroaryl can also be part of a bi- or polycyclic system having up to 14 ring members, wherein the ring system can be formed with further saturated or (partially) unsaturated cycloalkyl or heterocycloalkyl, aromatic or heteroaromatic ring systems, which can in turn be unsubstituted or mono- or polysubstituted, if not indicated otherwise. In a preferred embodiment, the 5- to 6-membered heteroaryl is part of a bi- or polycyclic, preferably bicyclic, system. In another preferred embodiment, the 5- to 6-membered heteroaryl is not part of a bi- or polycyclic system.

Preferably, the 5- to 6-membered heteroaryl is selected from the group consisting of pyridyl (i.e. 2-pyridyl, 3-pyridyl, 4-pyridyl), pyridone (pyridinone), pyrimidinyl, pyridazinyl, pyrazinyl, pyrrolyl, imidazolyl, pyrazolyl, oxazolyl, isoxazolyl, thiazolyl, isothiazolyl, furanyl, thienyl (thiophenyl), triazolyl, thiadiazolyl, 4,5,6,7-tetrahydro-2H-indazolyl, 2,4,5,6-tetrahydrocyclo-penta[c]pyrazolyl, benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, imidazothiazolyl, indazolyl, indolizinyl, indolyl, isoquinolinyl, naphthyridinyl, oxazolyl, oxadiazolyl, phenazinyl, phenothiazinyl, phthalazinyl, purinyl, phenazinyl, tetrazolyl and triazinyl. Particularly preferred 5- to 6-membered heteroaryl are selected from the group consisting of pyridyl (i.e. 2-pyridyl, 3-pyridyl, 4-pyridyl). As pyridones can be regarded as pyridines that are substituted with =O, for the purpose of the specification the definition of pyridines that may optionally be substituted with =O covers pyridones.

The compounds according to the invention are defined by substituents, for example by $R_1$, $R_2$, $R_3$ and $R_4$ ($1^{st}$ generation substituents) which may optionally be for their part themselves be substituted ($2^{nd}$ generation substituents). Depending on the definition, these substituents of the substituents can optionally be for their part resubstituted ($3^{rd}$ generation substituents). If, for example, $R_1$=—$C_{1-10}$-alkyl ($1^{st}$ generation substituent), then the —$C_{1-10}$-alkyl can for its part be substituted, for example with a —NH($C_{1-6}$-alkyl) ($2^{nd}$ generation substituent). This produces the functional group $R_1$=(—$C_{1-10}$-alkyl-NH—$C_{1-6}$-alkyl). The —NH—$C_{1-6}$-alkyl can then for its part be resubstituted, for example with —Cl ($3^{rd}$ generation substituent). Overall, this produces the functional group $R_1$=—$C_{1-10}$-alkyl-NH—$C_{1-6}$-alkyl, wherein the —$C_{1-6}$-alkyl of the —NH—$C_{1-6}$-alkyl is substituted by —Cl.

However, in a preferred embodiment, the $3^{rd}$ generation substituents may not be resubstituted, i.e. there are then no $4^{th}$ generation substituents. More preferably, the $2^{nd}$ generation substituents may not be resubstituted, i.e. there are no $3^{rd}$ generation substituents.

If a residue occurs multiply within a molecule, then this residue can have respectively different meanings for various substituents: if, for example, both $R_2$ and $R_3$ denote —$C_{1-6}$-alkyl, then —$C_{1-6}$-alkyl can e.g. represent ethyl for $R_2$ and can represent methyl for $R_3$.

In connection with the terms "—$C_{1-10}$-alkyl", "—$C_{1-6}$-alkyl", "—$C_{1-4}$-alkyl", "—$C_{3-10}$-cycloalkyl", "—$C_{3-6}$-cycloalkyl", "3 to 7 membered heterocycloalkyl", "3 to 6-membered heterocycloalkyl", "—$C_{1-6}$-alkylene-", "—$C_{1-4}$-alkylene-" and "—$C_{1-2}$-alkylene-", the term "substituted" refers in the sense of the invention, with respect to the corresponding residues or groups, to the single substitution (monosubstitution) or multiple substitution (polysubstitution), e.g. disubstitution or trisubstitution; more preferably to monosubstitution or disubstitution; of one or more hydrogen atoms each independently of one another by at least one substituent. In case of a multiple substitution, i.e. in case of polysubstituted residues, such as di- or trisubstituted residues, these residues may be polysubstituted either on different or on the same atoms, for example trisubstituted on the same carbon atom, as in the case of —$CF_3$, —$CH_2CF_3$ or disubstituted as in the case of 1,1-difluorocyclohexyl, or at various points, as in the case of —CH(OH)—CH=CH—$CHCl_2$ or 1-chloro-3-fluorocyclohexyl. The multiple substitution can be carried out using the same or using different substituents.

In relation to the terms "aryl", "phenyl", "heteroaryl" and "5- to 6-membered heteroaryl", the term "substituted" refers in the sense of this invention to the single substitution (monosubstitution) or multiple substitution (polysubstitution), e.g. disubstitution or trisubstitution, of one or more hydrogen atoms each independently of one another by at least one substituent. The multiple substitution can be carried out using the same or using different substituents.

According to the invention, preferably —$C_{1-10}$-alkyl-, —$C_{1-6}$-alkyl, —$C_{1-4}$-alkyl, —$C_{3-10}$-cycloalkyl, —$C_{3-6}$-cycloalkyl, 3 to 7 membered heterocycloalkyl, 3 to 6-membered heterocycloalkyl, —$C_{1-6}$-alkylene-, —$C_{1-4}$-alkylene- and —$C_{1-2}$-alkylene- in each case independently from one another are unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —C(=O)—$C_{1-6}$-alkyl; —C(=O)—OH; —C(=O)—O$C_{1-6}$-alkyl; —C(=O)—$NH_2$; —C(=O)—NH($C_{1-6}$-alkyl); —C(=O)—N($C_{1-6}$-alkyl)$_2$; —OH; =O; —$OCF_3$; —$OCF_2H$; —$OCFH_2$; —$OCF_2Cl$; —$OCFCl_2$; —O—$C_{1-6}$-alkyl; —O—C(=O)—$C_{1-6}$-alkyl; —O—C(=O)—O—$C_{1-6}$-alkyl; —O—(CO)—NH($C_{1-6}$-alkyl); —O—C(=O)—N($C_{1-6}$-alkyl)$_2$; —O—S(=O)$_2$—$NH_2$; —O—S(=O)$_2$—NH($C_{1-6}$-alkyl); —O—S(=O)$_2$—N($C_{1-6}$-alkyl)$_2$; —$NH_2$; —NH($C_{1-6}$-alkyl); —N($C_{1-6}$-alkyl)$_2$; —NH—C(=O)—$C_{1-6}$-alkyl; —NH—C(=O)—O—$C_{1-6}$-alkyl; —NH—C(=O)—$NH_2$; —NH—C(=O)—NH($C_{1-6}$-alkyl); —NH—C(=O)—N($C_{1-6}$-alkyl)$_2$; —N($C_{1-6}$-alkyl)-C(=O)—$C_{1-6}$-alkyl; —N($C_{1-6}$-alkyl)-C(=O)—O—$C_{1-6}$-alkyl; —N($C_{1-6}$-alkyl)-C(=O)—$NH_2$; —N($C_{1-6}$-alkyl)-C(=O)—NH($C_{1-6}$-alkyl); —N($C_{1-6}$-alkyl) -C(=O)—N($C_{1-6}$-alkyl)$_2$; —NH—S(=O)$_2$OH; —NH—S(=O)$_2$—$C_{1-6}$-alkyl; —NH—S(=O)$_2$—O—$C_{1-6}$-alkyl; —NH—S(=O)$_2$—$NH_2$; —NH—S(=O)$_2$—NH($C_{1-6}$-alkyl); —NH—S(=O)$_2$N($C_{1-6}$-alkyl)$_2$; —N($C_{1-6}$-alkyl)-S(=O)$_2$—OH; —N($C_{1-6}$-alkyl)-S(=O)$_2$—$C_{1-6}$-alkyl; —N($C_{1-6}$-alkyl)-S(=O)$_2$—O—$C_{1-6}$-alkyl; —N($C_{1-6}$-alkyl)-S(=O)$_2$—$NH_2$; —N($C_{1-6}$-alkyl)-S(=O)$_2$—NH($C_{1-6}$-alkyl); —N($C_{1-6}$-alkyl)-S(=O)$_2$—N($C_{1-6}$-alkyl)$_2$; —$SCF_3$; —$SCF_2H$; —$SCFH_2$; —S—$C_{1-6}$-alkyl; —S(=O)—$C_{1-6}$-alkyl; —S(=O)$_2$—$C_{1-6}$-alkyl; —S(=O)$_2$—OH; —S(=O)$_2$—O—$C_{1-6}$-alkyl; —S(=O)$_2$—$NH_2$; —S(=O)$_2$—NH($C_{1-6}$-alkyl); —S(=O)$_2$—N($C_{1-6}$-alkyl)$_2$; —$C_{3-6}$-cycloalkyl; 3 to 6-membered heterocycloalkyl; phenyl; 5 or 6-membered heteroaryl; —O—$C_{3-6}$-cycloalkyl; —O-(3 to 6-membered heterocycloalkyl); —O-phenyl; —O-(5 or 6-membered heteroaryl); —C(=O)—$C_{3-6}$-cycloalkyl; C(=O)-(3 to 6-membered heterocycloalkyl); —C(=O)-phenyl; —C(=O)-(5 or 6-membered heteroaryl); —S(=O)$_2$—($C_{3-6}$-cycloalkyl); —S(=O)$_2$-(3 to 6-membered heterocycloalkyl); —S(=O)$_2$-phenyl and —S(=O)$_2$-(5 or 6-membered heteroaryl).

Preferred substituents of —$C_{1-10}$-alkyl, —$C_{1-6}$-alkyl, —$C_{1-4}$-alkyl, —$C_{3-10}$-cycloalkyl, —$C_{3-6}$-cycloalkyl, 3 to 7 membered heterocycloalkyl, 3 to 6-membered heterocycloalkyl, —$C_{1-6}$-alkylene - and —$C_{1-4}$-alkylene- are selected from the group consisting of —F; —Cl; —Br; —I; —CN; —$C_{1-6}$-alkyl; —$CF_3$; —$CF_2H$; —$CFH_2$; —C(=O)—$NH_2$; —C(=O)—NH($C_{1-6}$-alkyl); —C(=O)—N($C_{1-6}$-alkyl)$_2$; —OH; —$OCF_3$; —$OCF_2H$; —$OCFH_2$; —O—$C_{1-6}$-alkyl; —$NH_2$; —NH($C_{1-6}$-alkyl); —N($C_{1-6}$-alkyl)$_2$; —$SCF_3$; —$SCF_2H$; —$SCFH_2$; —S—$C_{1-6}$-alkyl; —S(=O)—$C_{1-6}$-alkyl; —S(=O)$_2$—$C_{1-6}$-alkyl; —$C_{3-6}$-cycloalkyl; 3 to 6-membered heterocycloalkyl; phenyl and 5 or 6-membered heteroaryl; and particularly preferably —F, —CN, —$CH_3$, —$CH_2CH_3$, —$CF_3$; —$CF_2H$; —$CFH_2$; —C(=O)—$NH_2$; —C(=O)—NH($CH_3$); —C(=O)—N($CH_3$)$_2$; —OH, —$NH_2$, —$OCH_3$, —$SCH_3$, —S(=O)$_2$($CH_3$), —S(=O)($CH_3$), —N($CH_3$)$_2$, cyclopropyl and oxetanyl. According to this embodiment, —$C_{1-10}$-alkyl, —$C_{1-6}$-alkyl, —$C_{1-4}$-alkyl, —$C_{3-10}$-cycloalkyl, —$C_{3-6}$-cycloalkyl, 3 to 7 membered heterocycloalkyl, 3 to 6-membered heterocycloalkyl are preferably each independently from one another unsubstituted, mono- di- or trisubstituted, more preferably unsubstituted or mono-substituted or disubstituted with a substituent selected from the group consisting of —F; —Cl; —Br; —I; —CN; —$C_{1-6}$-alkyl; —$CF_3$; —$CF_2H$; —$CFH_2$; —C(=O)—$NH_2$; —C(=O)—NH($C_{1-6}$-alkyl); —C(=O)—N($C_{1-6}$-alkyl)$_2$; —OH; —$OCF_3$; —$OCF_2H$; —$OCFH_2$; —O—$C_{1-6}$-alkyl; —$NH_2$; —NH($C_{1-6}$-alkyl); —N($C_{1-6}$-alkyl)$_2$; —$SCF_3$; —$SCF_2H$; —$SCFH_2$; —S—$C_{1-6}$-alkyl; —S(=O)—$C_{1-6}$-alkyl; —S(=O)$_2$—$C_{1-6}$-alkyl; —$C_{3-6}$-cycloalkyl; 3 to 6-membered heterocycloalkyl; phenyl and 5 or 6-membered heteroaryl. Preferably, —$C_{1-6}$-alkylene- groups and —$C_{1-4}$-alkylene- groups are unsubstituted.

According to the invention, preferably aryl, phenyl and 5 or 6-membered heteroaryl in each case independently from one another are unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —$C_{1-4}$-alkylene-$CF_3$; $C_{1-4}$-alkylene-$CF_2H$; —$C_{1-4}$-alkylene-$CFH_2$; —C(=O)—$C_{1-6}$-alkyl; —C(=O)—OH; —C(=O)—O$C_{1-6}$-alkyl; —C(=O)—NH(OH); —C(=O)—$NH_2$; —C(=O)—NH($C_{1-6}$-alkyl); —C(=O)—N($C_{1-6}$-alkyl)$_2$; =O; —OH; —$OCF_3$; —$OCF_2H$; —$OCFH_2$; —$OCF_2Cl$; —$OCFCl_2$; —O—$C_{1-6}$-alkyl; —O—$C_{3-6}$-cycloalkyl; —O-(3 to 6-membered heterocycloalkyl); —NH₂; —NH(C₁₋₆-alkyl); —N(C₁₋₆-alkyl)₂; —NH—C(=O)—C₁₋₆-alkyl; —N(C₁₋₆-alkyl)-C(=O)—C₁₋₆-alkyl; —NH—C(=O)—NH₂; —NH—C(=O)—NH(C₁₋₆-alkyl); —NH—C(=O)—N(C₁₋₆-alkyl)₂; —N(C₁₋₆-alkyl)-C(=O)—NH(C₁₋₆-alkyl); —N(C₁₋₆-alkyl)-C(=O)—N(C₁₋₆-alkyl)₂; —NH—S(=O)₂—C₁₋₆-alkyl; —SCF₃; —S—C₁₋₆-alkyl; —S(=O)—C₁₋₆-alkyl; —S(=O)₂—C₁₋₆-alkyl; —S(=O)₂—NH₂; —S(=O)₂—NH(C₁₋₆-alkyl); —S(=O)₂—N(C₁₋₆-alkyl)₂; —C₃₋₆-cycloalkyl; —C₁₋₄-alkylene-C₃₋₆-cycloalkyl; 3 to 6-membered heterocycloalkyl; —C₁₋₄-alkylene-(3 to 6-membered heterocycloalkyl); phenyl or 5 or 6-membered heteroaryl.

Preferred substituents of aryl, phenyl and 5 or 6-membered heteroaryl are selected from the group consisting of —F; —Cl; —Br; —I; —CN; —C₁₋₆-alkyl; —CF₃; —CF₂H; —CFH₂; —C₁₋₄-alkylene-CF₃; —C₁₋₄-alkylene-CF₂H; —C₁₋₄-alkylene-CFH₂; —OH; —OCF₃; —OCF₂H; —OCFH₂; —O—C₁₋₆-alkyl; —O—C₃₋₆-cycloalkyl and —C₃₋₆-cycloalkyl; and particularly preferably of —F; —Cl; —Br; —CN; —CH₃; —CH₂CH₃; —CF₃; —CF₂H; —CFH₂; —CH₂—CF₃; =O; —OH; —OCF₃; —OCF₂H; —OCFH₂; —O—CH₃; —O-cyclopropyl and cyclopropyl. According to this embodiment, aryl, phenyl and 5 or 6-membered heteroaryl are preferably each independently from one another unsubstituted, mono- di- or trisubstituted, more preferably unsubstituted or monosubstituted or disubstituted with a substituent selected from the group consisting of —F; —Cl; —Br; —I; —CN; —C₁₋₆-alkyl; —CF₃; —CF₂H; —CFH₂; —C₁₋₄-alkylene-CF₃; —C₁₋₄-alkylene-CF₂H; —C₁₋₄-alkylene-CFH₂; =O; —OH; —OCF₃; —OCF₂H; —OCFH₂; —O—C₁₋₆-alkyl; —O—C₃₋₆-cycloalkyl and —C₃₋₆-cycloalkyl. A particularly preferred substituted 5 or 6-membered heteroaryl is N-methyl-2-oxo-pyridyl.

In a preferred embodiment, the compound according to the invention has a stereochemistry according to general formula (II), (III), (IV) or (V)

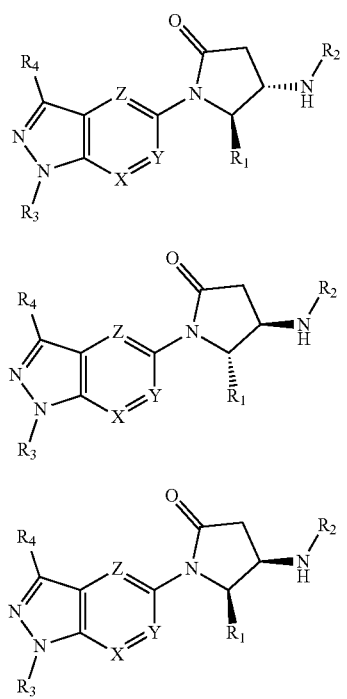

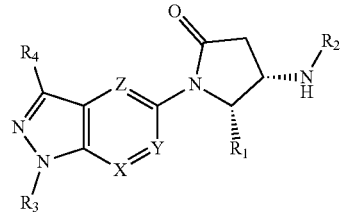

In a preferred embodiment, the compound according to the invention has a stereochemistry according to general formula (II) or (III), such that the residues —R₁ and —NH—R₂ on the pyrrolidone ring are oriented trans. Preferably, the compound according to the invention has a stereochemistry according to general formula (II). Preferably, the compound according to the invention has a stereochemistry according to general formula (III). The stereochemistry according to general formula (II) is particularly preferred.

In another preferred embodiment, the compound according to the invention has a stereochemistry according to general formula (IV) or (V), such that the residues —R₁ and —NH—R₂ on the pyrrolidone ring are oriented cis. Preferably, the compound according to the invention has a stereochemistry according to general formula (IV). Preferably, the compound according to the invention has a stereochemistry according to general formula (V).

In the compound of the invention according to any of general formulas (I), (II), (III), (IV) or (V), R₁ represents —C₁₋₁₀-alkyl; —C₃₋₁₀-cycloalkyl; —C₁₋₆-alkylene-C₃₋₁₀-cycloalkyl; 3 to 7 membered heterocycloalkyl; —C₁₋₆-alkylene-(3 to 7 membered hetero cyclo alkyl); aryl; —C₁₋₆-alkylene-aryl; 5 or 6-membered heteroaryl; or —C₁₋₆-alkylene-(5 or 6-membered heteroaryl).

In a preferred embodiment, R₁ represents —C₃₋₁₀-cycloalkyl; —C₁₋₆-alkylene-C₃₋₁₀-cycloalkyl; aryl; or 5 or 6-membered heteroaryl.

In particularly preferred embodiments, R₁ represents
(i) cyclopropyl, unsubstituted;
(ii) —CH₂-cyclopropyl, unsubstituted;
(iii) phenyl, unsubstituted or mono- or disubstituted with substituents independently of one another selected from the group consisting of —F, —Cl, —Br, —CH₃, —CF₃, —CN, cyclopropyl, and —OCH₃, wherein phenyl is optionally annealed to a dioxolane ring by a substituent —O—CH₂CH₂—O—; or
(iv) pyridyl, unsubstituted or mono- or disubstituted with substituents independently of one another selected from the group consisting of —F, —Cl, —Br, —CH₃, —CF₃, —CN, and —OCH₃.

In the compound of the invention according to any of general formulas (I), (II), (III), (IV) or (V), R₂ represents —C(=O)—C₁₋₁₀-alkyl; —C(=O)—C₃₋₁₀-cycloalkyl; —C(=O)—C₁₋₆-alkylene-C₃₋₁₀-cycloalkyl; —C(=O)-(3 to 7 membered heterocycloalkyl); —C(=O)—C₁₋₆-alkylene-(3 to 7 membered heterocycloalkyl); —C(=O)-aryl; —C(=O)—C₁₋₆-alkylene-aryl; —C(=O)-(5 or 6-membered heteroaryl); —C(=O)—C₁₋₆-alkylene-(5 or 6-membered heteroaryl); —S(=O)₁₋₂—C₁₋₁₀-alkyl; —S(=O)₁₋₂—C₃₋₁₀-cycloalkyl; —S(=O)₁₋₂—C₁₋₆-alkylene-C₃₋₁₀-cycloalkyl; —S(=O)₁₋₂-(3 to 7 membered heterocycloalkyl); —S(=O)₁₋₂—C₁₋₆-alkylene-(3 to 7 membered heterocycloalkyl); —S(=O)₁₋₂-aryl; —S(=O)₁₋₂—

$C_{1-6}$-alkylene-aryl; —S(=O)$_{1-2}$-(5 or 6-membered heteroaryl); or —S(=O)$_{1-2}$—$C_{1-6}$-alkylene-(5 or 6-membered heteroaryl).

In a preferred embodiment, $R_2$ represents —C(=O)—$C_{1-10}$-alkyl; —C(=O)—$C_{3-10}$-cycloalkyl; —C(=O)—$C_{1-6}$-alkylene-$C_{3-10}$-cycloalkyl; —C(=O)-(3 to 7 membered heterocycloalkyl); —C(=O)-(5 or 6-membered heteroaryl); —S(=O)$_2$—$C_{1-10}$-alkyl; —S(=O)$_2$—$C_{3-10}$-cycloalkyl; —S(=O)$_2$—$C_{1-6}$-alkylene-$C_{3-10}$-cycloalkyl or —S(=O)$_2$-(5 or 6-membered heteroaryl).

In particularly preferred embodiments, $R_2$ represents
(i) —C(=O)—$C_{1-10}$-alkyl, unsubstituted or mono- or disubstituted with substituents independently of one another selected from the group consisting of —F, —Cl, and —Br;
(ii) —C(=O)-cyclopropyl, unsubstituted or mono- or disubstituted with substituents independently of one another selected from the group consisting of —F, —Cl, —Br, —CH$_3$, —CF$_3$, —CN, and —OCH$_3$;
(iii) —C(=O)-cyclobutyl, unsubstituted or mono- or disubstituted with substituents independently of one another selected from the group consisting of —F, —Cl, —Br, —CH$_3$, —CF$_3$, —CN and —OCH$_3$;
(iv) —C(=O)-2-tetrahydrofuranyl, unsubstituted;
(v) —C(=O)-(5- to 6-membered heteroaryl), wherein said 5- to 6-membered heteroaryl is selected from the group consisting of thiazolyl, pyrazolyl, oxazolyl and 1-oxa-2,4-diazolyl, 1,2,5-oxadiazolyl, isoxazolyl, isothiazolyl, wherein in each case said 5- to 6-membered heteroaryl is unsubstituted or mono- or disubstituted with substituents independently of one another selected from the group consisting of —F, —Cl, —Br, —CH$_3$, —CF$_3$, —CN, =O, and —OCH$_3$;
(vi) —S(=O)$_2$—$C_{1-10}$-alkyl, unsubstituted;
(vii) —S(=O)$_2$-cyclopropyl, unsubstituted;
(viii) —S(=O)$_2$—CH$_2$-cyclopropyl, unsubstituted; or
(ix) —S(=O)$_2$-(5- to 6-membered heteroaryl), wherein said 5- to 6-membered heteroaryl is selected from the group consisting of thiazolyl, pyrazolyl, oxazolyl and 1-oxa-2,4-diazolyl, 1,2,5-oxadiazolyl, isoxazolyl, isothiazolyl, wherein in each case said 5- to 6-membered heteroaryl is unsubstituted or mono- or disubstituted with substituents independently of one another selected from the group consisting of —F, —Cl, —Br, —CH$_3$, —CF$_3$, —CN, =O, and —OCH$_3$.

In the compound of the invention according to any of general formulas (I), (II), (III), (IV) or (V), $R_3$ represents 3 to 7 membered heterocycloalkyl; —$C_{1-6}$-alkylene-(3 to 7 membered heterocycloalkyl); 5 or 6-membered heteroaryl; —$C_{1-6}$-alkylene-(5 or 6-membered heteroaryl); —C(=O)-(3 to 7 membered heterocycloalkyl); —C(=O)—$C_{1-6}$-alkylene-(3 to 7 membered heterocycloalkyl); —C(=O)-(5 or 6-membered heteroaryl); —C(=O)—$C_{1-6}$-alkylene-(5 or 6-membered heteroaryl); —S(=O)$_{1-2}$-(3 to 7 membered heterocycloalkyl); —S(=O)$_{1-2}$—$C_{1-6}$-alkylene-(3 to 7 membered heterocycloalkyl); —S(=O)$_{1-2}$-(5 or 6-membered heteroaryl); or —S(=O)$_{1-2}$—$C_{1-6}$-alkylene-(5 or 6-membered heteroaryl).

In a preferred embodiment, $R_3$ represents 3 to 7 membered heterocycloalkyl; 5 or 6-membered heteroaryl; or —$C_{1-6}$-alkylene-(5 or 6-membered heteroaryl).

In particularly preferred embodiments, $R_3$ represents
(i) piperidinyl, unsubstituted or substituted with —C(=O)-cyclopropyl;
(ii) 5- to 6-membered heteroaryl selected from the group consisting of pyrazolyl, pyridyl, and pyrimidinyl, wherein in each case said 5- to 6-membered heteroaryl is unsubstituted or mono- or disubstituted with substituents independently of one another selected from the group consisting of —F, —Cl, —Br, —CH$_3$, —CF$_3$, —CN, =O, and —OCH$_3$; or
(iii) —CH$_2$-(5- to 6-membered heteroaryl) selected from the group consisting of —CH$_2$-pyrazolyl, —CH$_2$-pyridyl, and —CH$_2$-pyrimidinyl, wherein in each case said 5- to 6-membered heteroaryl is unsubstituted or mono- or disubstituted with substituents independently of one another selected from the group consisting of —F, —Cl, —Br, —CH$_3$, —CF$_3$, —CN, =O, and —OCH$_3$.

In the compound of the invention according to any of general formulas (I), (II), (III), (IV) or (V), $R_4$ represents —H; —F; —Cl; —Br; —I; —CN; —CH$_3$; —CF$_3$; —CF$_2$H; —CFH$_2$ or cyclopropyl.

In a preferred embodiment, $R_4$ represents —H.

In the compound of the invention according to any of general formulas (I), (II), (III), (IV) or (V), X represents N or CR$_5$; wherein $R_5$ represents —H; —F; —Cl; —Br; —I; —CN; —$C_{1-10}$-alkyl or —$C_{3-10}$-cycloalkyl.

In a preferred embodiment, X represents N or CH.

In the compound of the invention according to any of general formulas (I), (II), (III), (IV) or (V), Y represents N or CR$_6$; wherein $R_6$ represents —H; —F; —Cl; —Br; —I; —CN; —$C_{1-10}$-alkyl or —$C_{3-10}$-cycloalkyl.

In a preferred embodiment, Y represents N or CH.

In the compound of the invention according to any of general formulas (I), (II), (III), (IV) or (V), Z represents N or CR$_7$; wherein $R_7$ represents —H; —F; —Cl; —Br; —I; —CN; —$C_{1-10}$-alkyl or —$C_{3-10}$-cycloalkyl.

In a preferred embodiment, Z represents N or CH.

In particularly preferred embodiments,
(i) X represents CR$_5$, preferably CH; Y represents CR$_6$, preferably CH; and Z represents CR$_7$, preferably CH; or
(ii) X represents N; Y represents CR$_6$, preferably CH; and Z represents CR$_7$, preferably CH; or
(iii) X represents CR$_5$, preferably CH; Y represents N; and Z represents CR$_7$, preferably CH; or
(iv) X represents CR$_5$, preferably CH; Y represents CR$_6$, preferably CH; and Z represents N; or
(v) X represents N; Y represents N; and Z represents CR$_7$, preferably CH; or
(vi) X represents N; Y represents CR$_6$, preferably CH; and Z represents N; or
(vii) X represents CR$_5$, preferably CH; Y represents N; and Z represents N; or
(viii) X represents N; Y represents N; and Z represents N.

In particularly preferred embodiments of the invention according to any of general formulas (I), (II), (III), (IV) or (V),
$R_1$ represents phenyl, unsubstituted or mono- or disubstituted with substituents independently of one another selected from the group consisting of —F, —Cl, —Br, —CH$_3$, —CF$_3$, —CN, and —OCH$_3$; and/or
$R_2$ represents —C(=O)—$C_{1-6}$-alkyl; —C(=O)-cyclopropyl; or —C(=O)-cyclobutyl, unsubstituted or mono- or disubstituted with substituents independently of one another selected from the group consisting of —F, —Cl, and —Br; and/or
$R_3$ represents N-methyl-2-oxo-pyridyl.

In a preferred embodiment, the compound according to the invention is selected from the group consisting of
1 N-[(2R,3S)-2-(3-chlorophenyl)-1-[1-(1-methyl-6-oxo-3-pyridyl)indazol-5-yl]-5-oxo-pyrrolidin-3-yl]-2,2-difluoro-propanamide 2  2,2-difluoro-N-[rac-(2R,3S)-2-(2,4-difluorophenyl)-1-[1-(1-methyl-6-oxo-3-pyridyl)indazol-5-yl]-5-oxo-pyrrolidin-3-yl]propanamide 3  2,2-difluoro-N-[rac-(2R,3S)-2-(2,3-dihydro-1,4-benzodioxin-6-yl)-1-[1-(1-methyl-6-oxo-3-pyridyl)indazol-5-yl]-5-oxo-pyrrolidin-3-yl]propanamide 4  2,2-difluoro-N-[(2R,3S)-1-[1-(1-methyl-6-oxo-3-pyridyl)indazol-5-yl]-5-oxo-2-phenyl-pyrrolidin-3-yl]propanamide 5  2,2-difluoro-N-[(2R,3S)-2-(3-fluorophenyl)-1-[1-(1-methyl-6-oxo-3-pyridyl)indazol-5-yl]-5-oxo-pyrrolidin-3-yl]propanamide 6  2,2-difluoro-N-[(2R,3S)-2-(2-fluorophenyl)-1-[1-(1-methyl-6-oxo-3-pyridyl)indazol-5-yl]-5-oxo-pyrrolidin-3-yl]propanamide 7  2,2-difluoro-N-[rac-(2R,3S)-5-oxo-2-phenyl-1-[1-(3-pyridyl)indazol-5-yl]pyrrolidin-3-yl]propanamide 9  2,2-difluoro-N-[rac-(2R,3S)-1-[1-(5-fluoro-2-pyridyl)indazol-5-yl]-5-oxo-2-phenyl-pyrrolidin-3-yl]propanamide 13  5-methyl-N-[(2R,3S)-1-[1-(1-methyl-6-oxo-3-pyridyl)indazol-5-yl]-5-oxo-2-phenyl-pyrrolidin-3-yl]thiazole-2-carboxamide 15  2,2-difluoro-N-[(2R,3S)-2-(4-fluoro-3-methoxy-phenyl)-1-[1-(1-methyl-6-oxo-3-pyridyl)indazol-5-yl]-5-oxo-pyrrolidin-3-yl]propanamide 17  2,2-difluoro-N-[(2R,3S)-2-(4-fluorophenyl)-1-[1-(1-methyl-6-oxo-3-pyridyl)indazol-5-yl]-5-oxo-pyrrolidin-3-yl]propanamide 18  1-fluoro-N-[(2R,3S)-1-[1-(1-methyl-6-oxo-3-pyridyl)indazol-5-yl]-5-oxo-2-phenyl-pyrrolidin-3-yl]cyclopropanecarboxamide 22  2,2-difluoro-N-[rac-(2R,3S)-1-[1-(6-methoxy-3-pyridyl)indazol-5-yl]-5-oxo-2-phenyl-pyrrolidin-3-yl]propanamide 23  2,2-difluoro-N-[rac-(2R,3S)-5-oxo-2-phenyl-1-[1-(4-pyridyl)indazol-5-yl]pyrrolidin-3-yl]propanamide 24  2,2-difluoro-N-[rac-(2R,3S)-1-[1-(6-methyl-3-pyridyl)indazol-5-yl]-5-oxo-2-phenyl-pyrrolidin-3-yl]propanamide 25  2,2-difluoro-N-[rac-(2R,3S)-1-[1-(2-methyl-4-pyridyl)indazol-5-yl]-5-oxo-2-phenyl-pyrrolidin-3-yl]propanamide 26  1-methyl-N-[(2R,3S)-1-[1-(1-methyl-6-oxo-3-pyridyl)indazol-5-yl]-5-oxo-2-phenyl-pyrrolidin-3-yl]cyclopropanecarboxamide 27  2,2-difluoro-N-[rac-(2R,3S)-1-[1-(2-methoxy-4-pyridyl)indazol-5-yl]-5-oxo-2-phenyl-pyrrolidin-3-yl]propanamide 31  2,2-difluoro-N-[rac-(2R,3S)-1-[1-[(2-methoxy-4-pyridyl)methyl]indazol-5-yl]-5-oxo-2-phenyl-pyrrolidin-3-yl]propanamide 32  2,2-difluoro-N-[rac-(2R,3S)-1-[1-[(1-methylpyrazol-3-yl)methyl]indazol-5-yl]-5-oxo-2-phenyl-pyrrolidin-3-yl]propanamide 33  2,2-difluoro-N-[rac-(2R,3S)-1-[1-[(6-methoxy-3-pyridyl)methyl]indazol-5-yl]-5-oxo-2-phenyl-pyrrolidin-3-yl]propanamide 34  2,2-difluoro-N-[rac-(2R,3S)-1-[1-[(1-methyl-6-oxo-3-pyridyl)methyl]indazol-5-yl]-5-oxo-2-phenyl-pyrrolidin-3-yl]propanamide 35  2,2-difluoro-N-[rac-(2R,3S)-1-[1-[1-(cyclopropanecarbonyl)-4-piperidyl]indazol-5-yl]-5-oxo-2-phenyl-pyrrolidin-3-yl]propanamide 38  2,2-difluoro-N-[rac-(2R,3S)-1-[1-[(1-methyl-2-oxo-4-pyridyl)methyl]indazol-5-yl]-5-oxo-2-phenyl-pyrrolidin-3-yl]propanamide 39  N-[(2R,3S)-2-(2-fluorophenyl)-1-[1-(1-methyl-6-oxo-3-pyridyl)indazol-5-yl]-5-oxo-pyrrolidin-3-yl]cyclopropanecarboxamide 40  N-[rac-(2R,3S)-1-[1-[(2-methoxy-4-pyridyl)methyl]indazol-5-yl]-5-oxo-2-phenyl-pyrrolidin-3-yl]cyclopropanecarboxamide 41  N-[(2R,3S)-1-[1-(1-methyl-6-oxo-3-pyridyl)indazol-5-yl]-2-(o-tolyl)-5-oxo-pyrrolidin-3-yl]cyclopropanecarboxamide 42  2,2-difluoro-N-[(2R,3S)-2-(2-methoxy-4-pyridyl)-1-[1-(1-methyl-6-oxo-3-pyridyl)indazol-5-yl]-5-oxo-pyrrolidin-3-yl]propanamide 43  2,2-difluoro-N-[(2R,3S)-1-[1-(1-methyl-6-oxo-3-pyridyl)indazol-5-yl]-2-(o-tolyl)-5-oxo-pyrrolidin-3-yl]propanamide 44  N-[(2R,3S)-1-[1-(1-methyl-6-oxo-3-pyridyl)indazol-5-yl]-5-oxo-2-phenyl-pyrrolidin-3-yl]thiazole-4-carboxamide 45  1-methyl-N-[(2R,3S)-1-[1-(1-methyl-6-oxo-3-pyridyl)indazol-5-yl]-5-oxo-2-phenyl-pyrrolidin-3-yl]pyrazole-3-carboxamide 46  2,2-difluoro-N-[rac-(2R,3S)-1-[1-(1-methylpyrazol-4-yl)indazol-5-yl]-5-oxo-2-phenyl-pyrrolidin-3-yl]propanamide 47  2,2-difluoro-N-[rac-(2R,3S)-1-[1-(5-fluoropyrimidin-2-yl)indazol-5-yl]-5-oxo-2-phenyl-pyrrolidin-3-yl]propanamide 48  (R)—N-[(2R,3S)-1-[1-(1-methyl-6-oxo-3-pyridyl)indazol-5-yl]-5-oxo-2-phenyl-pyrrolidin-3-yl]tetrahydrofuran-2-carboxamide 49  N-[(2R,3S)-1-[1-(1-methyl-6-oxo-3-pyridyl)indazol-5-yl]-5-oxo-2-phenyl-pyrrolidin-3-yl]oxazole-2-carboxamide 50  N-[(2R,3S)-1-[1-(1-methyl-6-oxo-3-pyridyl)indazol-5-yl]-5-oxo-2-phenyl-pyrrolidin-3-yl]oxazole-4-carboxamide 51  5-methyl-N-[(2R,3S)-1-[1-(1-methyl-6-oxo-3-pyridyl)indazol-5-yl]-5-oxo-2-phenyl-pyrrolidin-3-yl]-1,2,4-oxadiazole-3-carboxamide in each case in the form of the free compound or a physiologically acceptable salt thereof.

The compounds according to the invention can be synthesized by standard reactions in the field of organic chemistry known to the person skilled in the art or in a manner as described herein (cf. Reaction Schemes below) or analogously. The reaction conditions in the synthesis routes described herein are known to the skilled person and are for some cases also exemplified in the Examples described herein.

Reaction scheme 1:

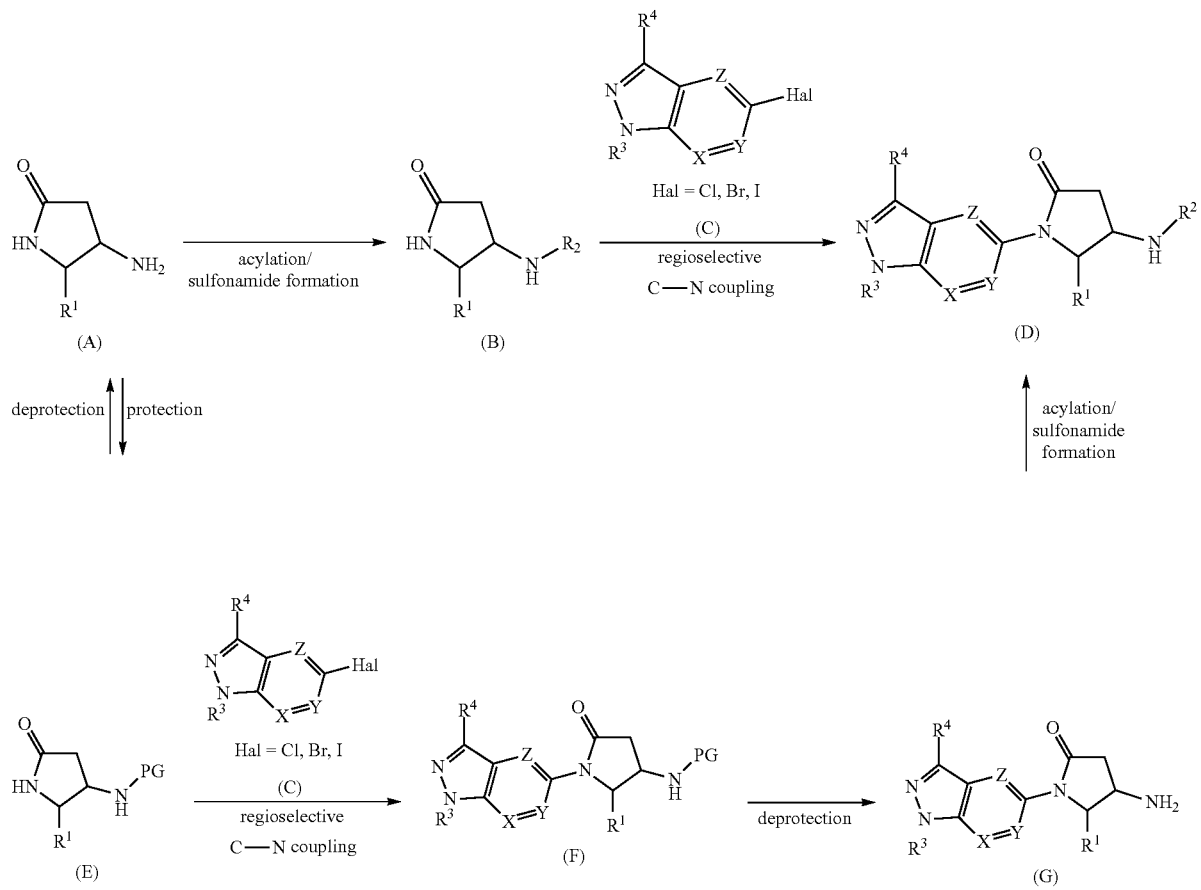

Substituted indazole moieties in compounds of formula (D) and formula (F) are introduced by subjecting lactam (B) or lactam (E) in a regioselective metal catalyzed C—N coupling reaction with corresponding indazole halides (C), preferred with corresponding indazole iodides. Metal catalyzed C—N coupling reactions are generally known in the art (*Current Organic Synthesis*, 2011, 8, 53). Favorable C—N coupling reactions are palladium and copper catalyzed cross-coupling reactions (*Chem. Rev.*, 2016, 116, 12564; *Chem. Soc. Rev.*, 2014, 43, 3525; *Chem. Sci.*, 2010, 1, 13). Regioselective C—N couplings with arylhalides are known in the art (*Chem. Sci.*, 2011, 2, 27; *J. Am. Chem. Soc.*, 2001, 123, 7727).

Primary amines (A) and (G) are converted to corresponding amides and sulfonamides (acylation and sulfonamide formation) (B) and (D) using commercially available acids (activation of acids using e.g. HATU) or acid chlorides under standard amide coupling reaction conditions (*March's Advanced Organic Chemistry*, 2007, 6th Edition, page 1427-1474).

Introduction of different orthogonal protecting groups PG (e.g. Boc, Cbz) to convert (A) to (E) as well as deprotection of compounds of formula (E) to (A) is well described in the literature (T. W. Green, P. G. M. Wuts, *Protective Groups in Organic Synthesis*, Wiley-Interscience, New York, 1999).

Reaction scheme 1.1: Compounds (A) and (E) can be synthesized according to procedures which are described in the literature.

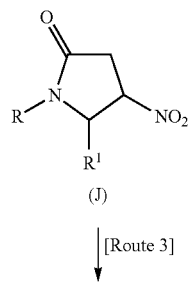

(J)

↓ [Route 3]

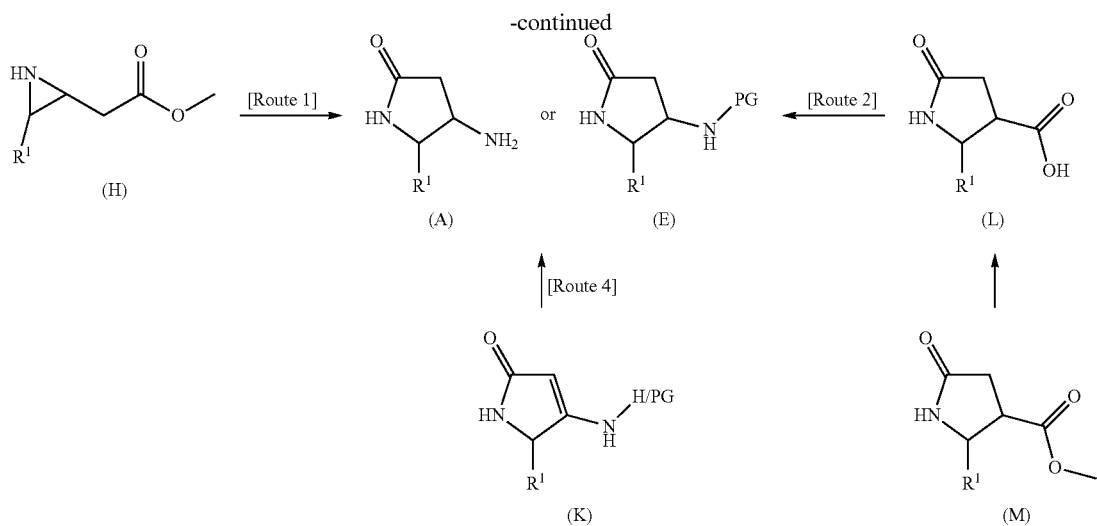

Route 1: Compounds of formula (A) and (E) can be synthesized starting from compounds of formula (H) (*J. Org. Chem.*, 2010, 76, 948).

Route 2: Synthesis of compounds of formula (m) and (l) is described in the literature (*J. Org. Chem.*, 2007, 72, 5016; *Org. Lett.*, 2007, 9, 4077; *J. Org. Chem.*, 2012, 77, 160). Compounds of formula (A) and (E) can be synthesized using Curtius rearrangement as key step to convert carboxylic acid (L) to corresponding primary amine (A) or (E). Curtius rearrangement is well known in the art (*Tetrahedron Letters*, 2010, 385).

Route 3: Synthesis of compounds of formula (J) is described in the literature (*Org. Lett.*, 2009, 11, 4512; *ACS Sustainable Chem. Eng.*, 2015, 3, 1873). Reduction of highly functionalized lactams (J) gives an alternate route for synthesis of compounds of formula (A) and (E). Reduction of nitro groups is well known in the art (*March's Advanced Organic Chemistry*, 2007, 6th Edition, page 1815f).

Route 4: Synthesis of compounds of formula (K) is described in the literature (*J. Heterocyclic Chem.*, 2014, 51, E25). Reduction of highly functionalized lactams (K) gives an alternate route for synthesis of compounds of formula (A) and (E). Reduction of enamides/imines is well known in the art (*March's Advanced Organic Chemistry*, 2007, 6th Edition, page 1053f and page 1811f).

Reaction scheme 2:

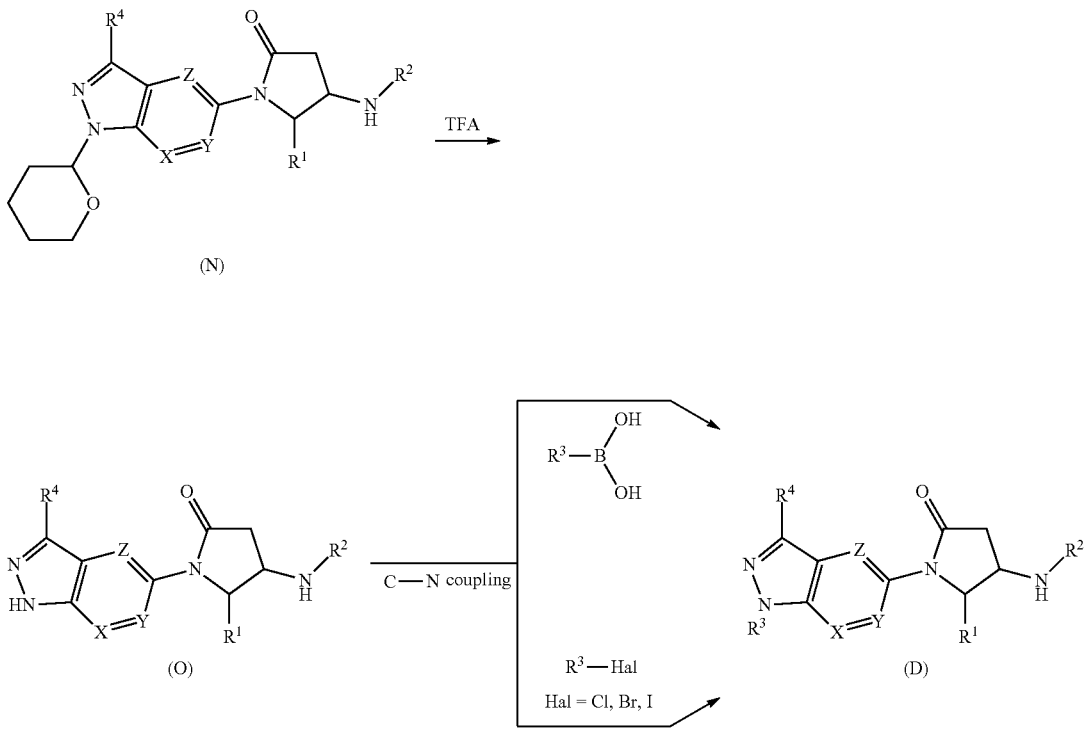

Compounds of formula (D) can be synthesized via regioselective C—N coupling of compound (O). Suitable C—N coupling reactions for N—H containing heterocycles are known in the art (Synthesis, 2011, 829; *Chem. Sci.*, 2011, 2, 27; Beilstein *J. Org. Chem.*, 2011, 7, 59; *J. Org. Chem.*, 2004, 69, 5578). Compound of formula (O) is synthesized via deprotection of compound (N) under acidic conditions.

The compounds according to the invention can be produced in the manner described here or in an analogous manner.

In a preferred embodiment, the compounds according to the invention are modulators of the glucocorticoid receptor. In the sense of the invention, the term "selective modulator of the glucocorticoid receptor (glucocorticoid receptor modulator)" preferably means that the respective compound exhibits in a cellular target engagement assay for agonistic or antagonistic potency on the glucocorticoid receptor an EC50 or IC50 value on the glucocorticoid receptor of at most 15 μM ($10 \cdot 10^{-6}$ mol/L) or at most 10 μM; more preferably at most 1 μM; still more preferably at most 500 nM ($10^{-9}$ mol/L); yet more preferably at most 300 nM; even more preferably at most 100 nM; most preferably at most 10 nM; and in particular at most 1 nM. In a preferred embodiment, the compound according to the invention exhibits in a cellular target engagement assay for agonistic or antagonistic potency on the glucocorticoid receptor an EC50 or IC50 value on the glucocorticoid receptor in the range of from 1 μM to 15 μM, more preferably from 100 nM to 1 μM, most preferably below 100 nM.

The person skilled in the art knows how to test compounds for modulation (agonistic or antagonistic) of the activity of the glucocorticoid receptor. Preferred target engagement assays for testing compounds for their agonistic or antagonistic potency (EC50, IC50) on the glucocorticoid receptor are described herein below:

Human Glucocorticoid Receptor (hGR) Ligand-Binding Assay

Potential selective glucocorticoid receptor modulators of this intervention can be tested for their binding affinity at the glucocorticoid receptor using the binding assay described below.

Preferably, the glucocortitcoid receptor extracted from cytosol of IM9 cells is used for competitive radioligand binding assays to calculate the IC50 values and binding affinity (Ki value) of the compounds according to the present invention. Preferably, a fixed concentration of the radioligand 3H-dexamethasone and a range of concentrations of compounds according to the present invention (as unlabeled competitors of dexamethasone) are mixed with the extracted glucocorticoid receptor in order to measure the potency/affinity with which they compete for the binding of the radioligand. Preferably, by using competition curves the $IC_{50}$ which is the concentration of competing ligand that displaces 50% of the specific binding of the radioligand is determined. Finally this $IC_{50}$ value is converted to a Ki value.

In a preferred embodiment, the compound according to the invention exhibits in a cellular target engagement assay for agonistic or antagonistic potency on the glucocorticoid receptor an EC50 or IC50 value on the glucocorticoid receptor of at most 1 μM ($10^{-6}$ mol/L); still more preferably at most 500 nM ($10^{-9}$ mol/L); yet more preferably at most 300 nM; even more preferably at most 100 nM; most preferably at most 50 nM; and in particular at most 10 nM or at most 1 nM.

In a preferred embodiment, the compound according to the invention exhibits in a cellular target engagement assay for agonistic or antagonistic potency on the glucocorticoid receptor an EC50 or IC50 value on the glucocorticoid receptor in the range of from 1 μM to 15 μM, more preferably from 100 nM to 1 μM, most preferably below 100 nM.

In a preferred embodiment, the compound according to the invention exhibits in a cellular target engagement assay for agonistic or antagonistic potency on the glucocorticoid receptor an EC50 or IC50 value on the glucocorticoid receptor in the range of from 0.1 nM ($10^{-9}$ mol/L) to 1000 nM; still more preferably 1 nM to 800 nM; yet more preferably 1 nM to 500 nM; even more preferably 1 nM to 300 nM; most preferably 1 nM to 100 nM; and in particular 1 nM to 80 nM.

In a preferred embodiment, the compound according to the invention exhibits in a cellular target engagement assay for agonistic or antagonistic potency on the glucocorticoid receptor an inhibition at 1 μM of at least 40%, more preferably at least 60%, most preferably at least 85%. In a preferred embodiment, the compound according to the invention exhibits in a cellular target engagement assay for agonistic or antagonistic potency on the glucocorticoid receptor an inhibition at 1 μM in the range from 40% to 60%, more preferably from greater than 60% to 85%, most preferably greater than 85%.

Preferably, the compounds according to the invention are useful as selective modulators of the glucocorticoid receptor.

Therefore, the compounds according to the invention are preferably useful for the in vivo treatment or prevention of diseases in which participation of the glucocorticoid receptor is implicated.

The invention therefore further relates to a compound according to the invention for use in the modulation of glucocorticoid receptor activity.

Therefore, another aspect of the invention relates to a compound according to the invention for use in the treatment and/or prophylaxis of a disorder which is mediated at least in part by the glucocorticoid receptor. Still another aspect of the invention relates to a method of treatment of a disorder which is mediated at least in part by the glucocorticoid receptor comprising the administration of a therapeutically effective amount of a compound according to the invention to a subject in need thereof, preferably a human.

A further aspect of the invention relates to the use of a compound according to the invention as medicament.

Another aspect of the invention relates to a pharmaceutical dosage form comprising a compound according to the invention. Preferably, the pharmaceutical dosage form comprises a compound according to the invention and one or more pharmaceutical excipients such as physiologically acceptable carriers, additives and/or auxiliary substances; and optionally one or more further pharmacologically active ingredient. Examples of suitable physiologically acceptable carriers, additives and/or auxiliary substances are fillers, solvents, diluents, colorings and/or binders. These substances are known to the person skilled in the art (see H. P. Fiedler, Lexikon der Hilfsstoffe fur Pharmazie, Kosmetik und angrenzende Gebiete, Editio Cantor Aulendoff).

The pharmaceutical dosage form according to the invention is preferably for systemic, topical or local administration, preferably for oral administration. Therefore, the pharmaceutical dosage form can be in form of a liquid, semisolid or solid, e.g. in the form of injection solutions, drops, juices, syrups, sprays, suspensions, tablets, patches, films, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and can also be administered as such.

The pharmaceutical dosage form according to the invention is preferably prepared with the aid of conventional means, devices, methods and processes known in the art. The amount of the compound according to the invention to be administered to the patient may vary and is e.g. dependent on the patient's weight or age and also on the type of administration, the indication and the severity of the disorder. Preferably 0.001 to 100 mg/kg, more preferably 0.05 to 75 mg/kg, most preferably 0.05 to 50 mg of a compound according to the invention are administered per kg of the patient's body weight.

The glucocorticoid receptor is believed to have potential to modify a variety of diseases or disorders in mammals such as humans. These include in particular inflammatory diseases, asthma, rheumatoid arthritis, inflammatory bowel disease, chronic obstructive pulmonary disease, acute respiratory distress syndrome, cystic fibrosis, osteoarthritis, polymyalgia rheumatica, giant cell arteritis, Sjögren syndrome, Duchenne muscular dystrophy, vasculitis, Behçet's disease, ulcerative colitis and Crohn's disease.

Further diseases and disorders that are believed to be modulated by the glucocorticoid receptor include endocrine disorders, preferably selected from primary or secondary adrenocortical insufficiency, congenital adrenal hyperplasia, hypercalcemia associated with cancer, and nonsuppurative thyroiditis; rheumatic disorders; preferably selected from psoriatic arthritis, rheumatoid arthritis, juvenile rheumatoid arthritis, ankylosing spondilitis, acute and subacute bursistis, acute nonspecific tenosynovitis, acute gouty arthritis, post-traumatic osteoarthritis, synovitis of osteoarthritis and epicondylitis; collagen diseases, preferably selected from systemic lupus erythematosus, systemic dermatomyositis (polymyositis) and acute rheumatic carditis; dermatologic diseases, preferably selected from pemphigus, bullous dermatitis herpetiformis, severe erythema multiforme (Stevens-Johnson syndrome), exfoliative dermatitis, mycosis fungoides, psoriasis and seborrheic dermatitis; allergic states, preferably selected from seasonal or perennial allergic rhinitis, bronchial asthma, contact dermatitis, atopic dermatitis, serum sickness and drug hypersensitivity reactions; ophthalmis diseases, preferably selected from allergic corneal marginal ulcers, herpes zoster ophthalmicus, anterior segment inflammation, diffuse posterior uveitis and choroiditis, sympathetic ophthalmia, allergic conjunctivitis, keratitis, chorioretinitis, optic neuritis, iritis and iridocyclitis; respiratory diseases, preferably selected from symptomatic sarcoidosis, Loeffler's syndrome, berylliosis, fulminating or disseminated pulmonary tubercolosis when used concurrently with antituberculous chemotherapy, aspiration pneumonitis; hematologic disorders, preferably selected from idiopathic thrombocytopenic purpura, secondary thrombocytopenia, acquired (autoimmune) hemolytic anemia, erythroblastopenia (RBC anemia), congenital (erythroid) hypoplastic anemia; neoplastic diseases, preferably selected from leukemias and lymphomas, acute leukemia of childhood; gastrointestinal diseases, preferably selected from ulcerative colitis and regional enteritis.

Another aspect of the invention relates to a compound according to the invention for use in the treatment and/or prophylaxis of pain and/or inflammation; more preferably inflammatory pain.

Another aspect of the invention relates to a compound according to the invention for use in the treatment and/or prophylaxis of asthma, rheumatoid arthritis, inflammatory bowel disease, chronic obstructive pulmonary disease, acute respiratory distress syndrome, cystic fibrosis, osteoarthritis, polymyalgia rheumatica, giant cell arteritis, Sjögren syndrome, Duchenne muscular dystrophy, vasculitis, Behçet's disease, ulcerative colitis and/or Crohn's disease.

Still another aspect of the invention relates to a compound according to the invention for use in the treatment and/or prophylaxis of endocrine disorders, preferably selected from primary or secondary adrenocortical insufficiency, congenital adrenal hyperplasia, hypercalcemia associated with cancer, and nonsuppurative thyroiditis; rheumatic disorders; preferably selected from psoriatic arthritis, rheumatoid arthritis, juvenile rheumatoid arthritis, ankylosing spondilitis, acute and subacute bursistis, acute nonspecific tenosynovitis, acute gouty arthritis, post-traumatic osteoarthritis, synovitis of osteoarthritis and epicondylitis; collagen diseases, preferably selected from systemic lupus erythematosus, systemic dermatomyositis (polymyositis) and acute rheumatic carditis; dermatologic diseases, preferably selected from pemphigus, bullous dermatitis herpetiformis, severe erythema multiforme (Stevens-Johnson syndrome), exfoliative dermatitis, mycosis fungoides, psoriasis and seborrheic dermatitis; allergic states, preferably selected from seasonal or perennial allergic rhinitis, bronchial asthma, contact dermatitis, atopic dermatitis, serum sickness and drug hypersensitivity reactions; ophthalmis diseases, preferably selected from allergic corneal marginal ulcers, herpes zoster ophthalmicus, anterior segment inflammation, diffuse posterior uveitis and choroiditis, sympathetic ophthalmia, allergic conjunctivitis, keratitis, chorioretinitis, optic neuritis, iritis and iridocyclitis; respiratory diseases, preferably selected from symptomatic sarcoidosis, Loeffler's syndrome, berylliosis, fulminating or disseminated pulmonary tubercolosis when used concurrently with antituberculous chemotherapy, aspiration pneumonitis; hematologic disorders, preferably selected from idiopathic thrombocytopenic purpura, secondary thrombocytopenia, acquired (autoimmune) hemolytic anemia, erythroblastopenia (RBC anemia), congenital (erythroid) hypoplastic anemia; neoplastic diseases, preferably selected from leukemias and lymphomas, acute leukemia of childhood; gastrointestinal diseases, preferably selected from ulcerative colitis and regional enteritis.

A further aspect of the invention relates to a method of treatment of pain and/or inflammation; more preferably inflammatory pain. Still a further aspect of the invention relates to a method of treatment of asthma, rheumatoid arthritis, inflammatory bowel disease, chronic obstructive pulmonary disease, acute respiratory distress syndrome, cystic fibrosis, osteoarthritis, polymyalgia rheumatica, giant cell arteritis, Sjögren syndrome, Duchenne muscular dystrophy, vasculitis, Behçet's disease, ulcerative colitis and/or Crohn's disease.

The following examples further illustrate the invention but are not to be construed as limiting its scope.

The following abbreviations are used in the descriptions of the experiments: AcOH=acetic acid; Attaphos=bis(di-tert-butyl(4 dimethylaminophenyl)phosphine)dichloropalladium(II); Cbz=carboxybenzyl; DCM=dichloromethane; DEA=diethylamine; DIPEA=N,N-diisopropylethylamine; DMAP=4-(dimethylamino)-pyridine; DMF=N,N-dimethylformamid; DMSO=dimethylsulfoxid; DPPA=diphenyl phosphoryl azide; dppf=1,1'; bis(diphenylphosphanyl)ferrocene; EA=ethyl acetate; EtOAc=ethyl acetate; EtOH=ethanol; HATU=1-[bis(dimethylamino)methylene]-1H-1,2,3-triazolo[4,5-b]pyridinium 3-oxid hexafluorophosphate; h=hour; LDA=lithiumdiisopropylamide; LiHMDS=lithium bis(trimethylsilyl)amide; MeOH=methanol; min=minute; n-BuLi=n-butyllithium;

sat.=saturated; RT=room temperature; Rt=retention time; tert=tertiary; TEA=triethylamine; TFA=trifluoro acetic acid; THF=tetrahydrofuran; p-TSA=para-toluene sulfonic acid; TMSCl=trimethylsilyl chloride.

Synthesis of trans-4-amino-5-(3-chlorophenyl)pyrrolidin-2-one (Intermediate A1)

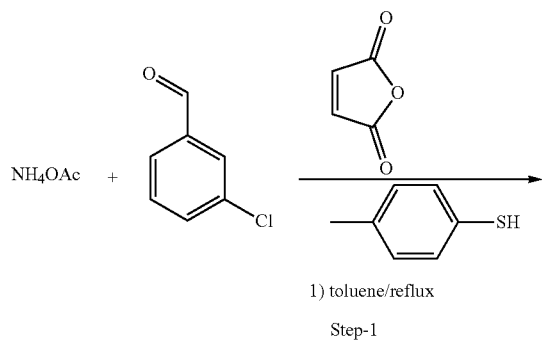

1) toluene/reflux

Step-1

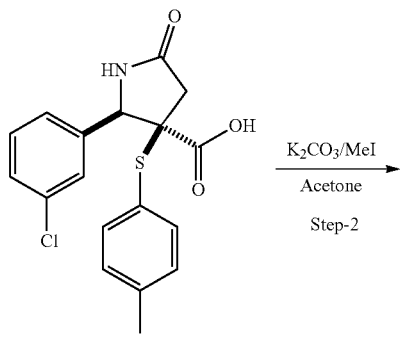

K₂CO₃/MeI
Acetone
Step-2

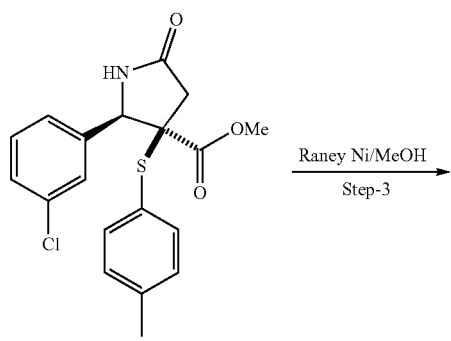

Raney Ni/MeOH
Step-3

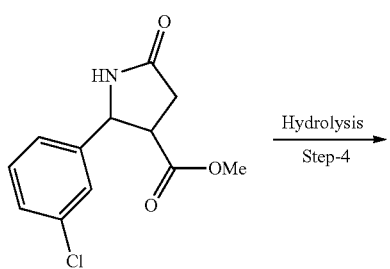

Hydrolysis
Step-4

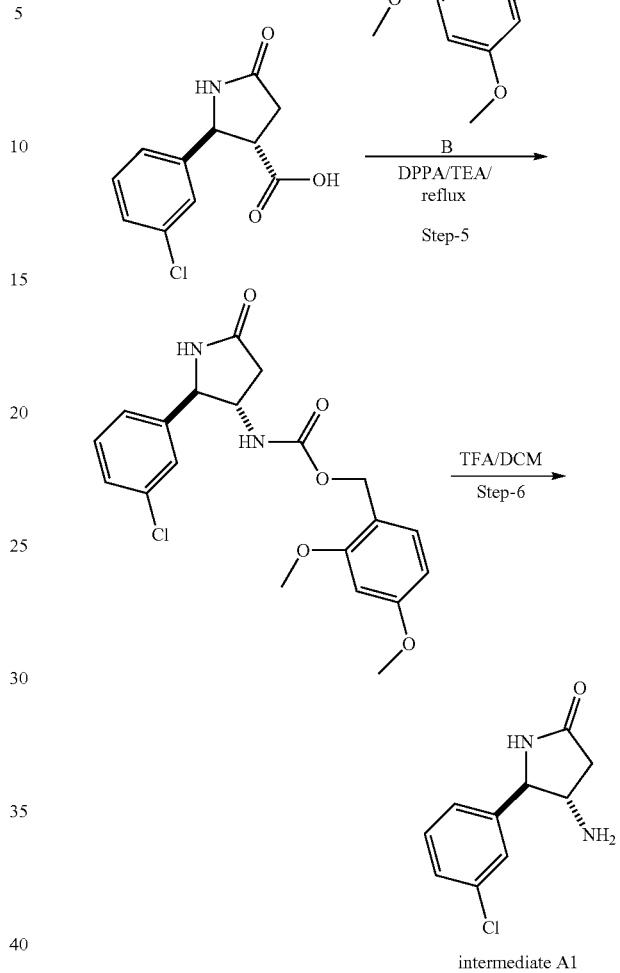

intermediate A1

Step 1: Maleic anhydride (9.8 g, 100 mmol, 1.0 eq), p-thiocresol (12.4 g, 100 mmol, 1.0 eq), ammonium acetate (7.8 g, 100 mmol, 1.0 eq), 3-chlorobenzaldehyde (11.5 mL, 100 mmol, 1.0 eq) and toluene (100 mL) were put in a sealed tube. The reaction mixture was stirred at RT for 1 h and then stirred at 150° C. for 16 h. After cooling to RT, the solvent was evaporated under reduced pressure, and the residue was basified with sat. NaHCO₃ solution and was extracted with DCM. The aqueous layer was acidified with 2N HCl under ice cooling and the crude product was extracted twice with EtOAc. The combined organic layers were washed with brine, dried over Na₂SO₄, filtered and concentrated to get the crude 2-(3-chlorophenyl)-5-oxo-3-(p-tolylthio)pyrrolidine-3-carboxylic acid (10.0 g).

Step 2: To a stirred solution of crude 2-(3-chlorophenyl)-5-oxo-3-(p-tolylthio)pyrrolidine-3-carboxylic acid (10.0 g, 27.7 mmol, 1.0 eq) in acetone (100 mL), potassium carbonate (15.3 g, 110.8 mmol, 4.0 eq) and methyl iodide (7.0 mL, 110.8 mmol, 4.0 eq) were added at 0° C. and the reaction mixture was stirred for 16 h at RT. The solvent was removed under reduced pressure, and the residue was partitioned between DCM and water. The aqueous layer was extracted twice with DCM. The combined organic layers were washed with brine, dried over Na₂SO₄, filtered and concentrated.

The crude product was purified by column chromatography (100-200 silica gel, 50% EtOAc:hexanes) to give methyl 2-(3-chlorophenyl)-5-oxo-3-(p-tolylthio)pyrrolidine-3-carboxylate as an off white solid (4.0 g, 38%).

Step 3: To a stirred solution of methyl 2-(3-chlorophenyl)-5-oxo-3-(p-tolylthio)pyrrolidine-3-carboxylate (10.0 g, 26.66 mmol, 1.0 eq) in EtOH:THF (100 mL, 2:1), Raney Nickel (2.5 g) was added and the reaction mixture was stirred for 2 h at RT After completion, the reaction mixture was filtered through a celite bed and the celite bed was then washed 2-3 times with EtOAc. The combined organic layers were concentrated and the crude product was purified by column chromatography (100-200 silica gel, 50% EtOAc: hexanes) to give methyl 2-(3-chlorophenyl)-5-oxopyrrolidine-3-carboxylate as an off white solid (6.0 g, 89%) (syn: anti, 1:1 mixture).

Step 4: To a stirred solution of methyl 2-(3-chlorophenyl)-5-oxopyrrolidine-3-carboxylate (3.0 g, 11.85 mmol, 1.0 eq) in MeOH (50 mL) was added 2 N NaOH solution (10 mL) and the reaction mixture was stirred at 80° C. for 2 h. After completion of the reaction (monitored by LCMS), the reaction mixture was concentrated and acidified with 2N HCl solution and the crude product was then extracted with 30% isopropanol-DCM. The combined organic layers were dried over Na$_2$SO$_4$ and concentrated under reduced pressure to get trans-2-(3-chlorophenyl)-5-oxopyrrolidine-3-carboxylic acid (2.5 g, 88%).

Step 5: To a stirred solution of trans-2-(3-chlorophenyl)-5-oxopyrrolidine-3-carboxylic acid (2.0 g, 8.36 mmol, 1.0 eq) in benzene:THF (100 mL, 4:1) were added TEA (2.35 mL, 16.73 mmol, 2.0 eq) and DPPA (2.35 ml, 10.8 mmol, 1.3 eq) and the reaction mixture was stirred at RT for 2 h. Then 2,4-dimethoxy benzyl alcohol (1.8 g, 10.87 mmol, 1.3 eq) was added to the reaction mixture and the reaction mixture was heated to reflux for 16 h. After completion, the reaction mixture was concentrated under reduced pressure to get the crude which was extracted with water and EtOAc. The combined organic layers were dried over Na$_2$SO$_4$ and concentrated under reduced pressure to get the crude product which was purified by column chromatography (100-200 mesh silica gel; 2% MeOH-DCM; R$_f$-value-0.5) to afford trans-2,4-dimethoxybenzyl (2-(3-chlorophenyl)-5-oxopyrrolidin-3-yl)carbamate (1.5 g, 44%).

Step 6: To a stirred solution of trans-2,4-dimethoxybenzyl (2-(3-chlorophenyl)-5-oxopyrrolidin-3-yl)carbamate (0.5 g, 1.23 mmol, 1.0 eq) in DCM (10 mL) was added TFA (2 mL) at 0° C., and the reaction was stirred for 3 h at RT After completion, the reaction mixture was diluted with EtOAc and washed with sat.NaHCO$_3$ solution. The combined organic layers were dried over Na$_2$SO$_4$ and concentrated to get the desired trans-4-amino-5-(3-chlorophenyl)pyrrolidin-2-one as a white solid (0.25 g, 96%).

Synthesis of
trans-4-amino-5-phenylpyrrolidin-2-one
(Intermediate A2)

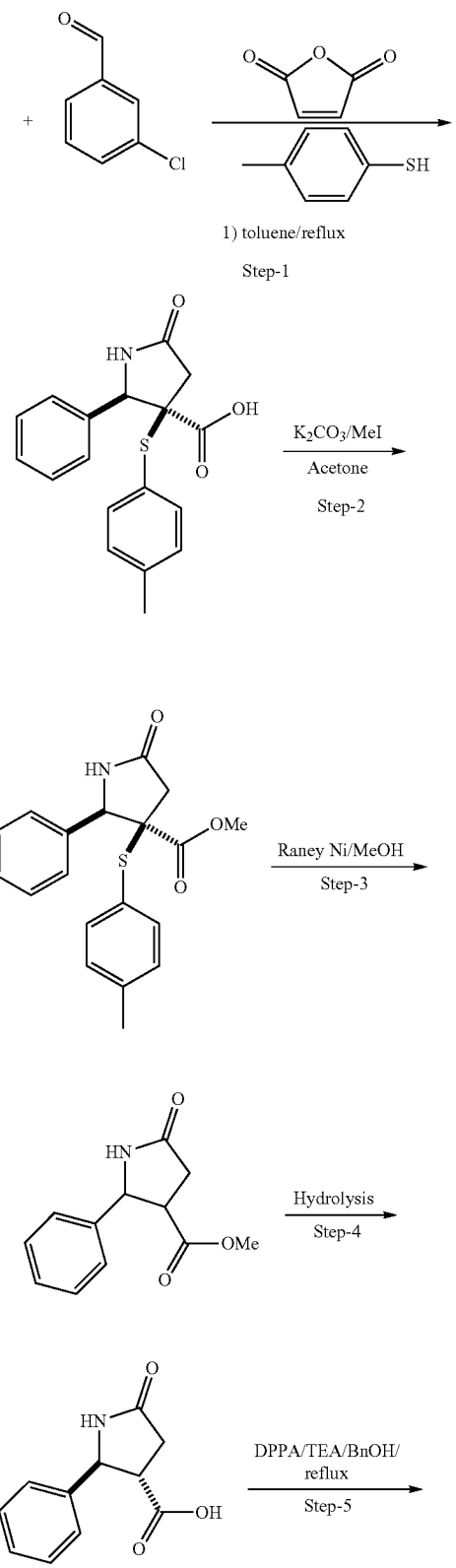

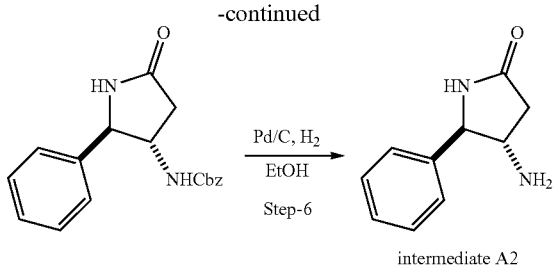

intermediate A2

Step 1: Maleic anhydride (9.8 g, 100 mmol, 1.0 eq), p-thiocresol (12.4 g, 100 mmol, 1.0 eq), ammonium acetate (7.8 g, 100 mmol, 1.0 eq) and benzaldehyde (10 mL, 100 mmol, 1.0 eq) were put in a sealed tube and 100 ml toluene was added. The reaction mixture was stirred at RT for 1 h and then stirred at 150° C. for 16 h. After cooling to RT, the solvent was evaporated under reduced pressure, and the residue was basified with sat.NaHCO₃ solution and was extracted with DCM. The aqueous layer was acidified with 2N HCl under ice cooling and the crude product was extracted twice with EtOAc. The combined organic layers were washed with brine, dried over Na₂SO₄, filtered and concentrated to get the crude 5-oxo-2-phenyl-3-(p-tolylthio) pyrrolidine-3-carboxylic acid (10.0 g, crude).

Step 2: To a stirred solution of crude 5-oxo-2-phenyl-3-(p-tolylthio)pyrrolidine-3-carboxylic acid (10.0 g, 30.58 mmol, 1.0 eq) in acetone (100 mL), potassium carbonate (16.8 g, 122.32 mmol, 4.0 eq) and methyl iodide (7.6 ml, 122.32 mmol, 4.0 eq) were added at 0° C., and the reaction was stirred for 16 h at RT. The solvent was removed under reduced pressure, and the residue was partitioned between DCM and water. The aqueous layer was extracted twice with DCM. The combined organic layers were washed with brine, dried over Na₂SO4, filtered, and concentrated. The crude product was purified by column chromatography (100-200 silica gel, 50% EtOAc:hexanes) to give methyl 5-oxo-2-phenyl-3-(p-tolylthio)pyrrolidine-3-carboxylate (4.0 g, 38%) as an off-white solid.

Step 3: To a stirred solution of methyl 5-oxo-2-phenyl-3-(p-tolylthio)pyrrolidine-3-carboxylate (4.0 g, 11.73 mmol, 1.0 eq) in EtOH:THF (100 mL, 2:1), Raney Nickel (1 g) was added and the reaction mixture was stirred for 2 h at RT After completion, the reaction mixture was filtered through a celite bed and the celite bed was washed 2-3 times with EtOAc. The combined organic layers were concentrated and the crude was purified by column chromatography (100-200 silica gel, 50% EtOAc:hexanes) to afford methyl 5-oxo-2-phenylpyrrolidine-3-carboxylate (2.2 g, 88%, syn:anti, 1:1 mixture) as an off-white solid.

Step 4: To a stirred solution of methyl 5-oxo-2-phenylpyrrolidine-3-carboxylate (1.0 g, 4.56 mmol, 1.0 eq) in MeOH (25 mL) was added 2 N NaOH solution (5 mL) and the reaction mixture was stirred at 80° C. for 2 h. After completion of the reaction (monitored by LCMS), the reaction mixture was concentrated and acidified with 2N HCl solution and was extracted with 30% isopropanol-DCM. The combined organic layers were dried over Na₂SO₄ and were concentrated under reduced pressure to get the desired trans-5-oxo-2-phenylpyrrolidine-3-carboxylic acid (0.8 g, 85%).

Step 5: To a stirred solution of trans-5-oxo-2-phenylpyrrolidine-3-carboxylic acid (0.5 g, 2.43 mmol, 1.0 eq) in benzene:THF (25 mL, 4:1) was added TEA (0.68 ml, 4.87 mmol, 2.0 eq) and DPPA (0.68 ml, 3.17 mmol, 1.3 eq) and the reaction mixture was stirred at RT for 2 h. Then benzyl alcohol (0.33 mL, 3.17 mmol, 1.3 eq) was added and the reaction mixture was heated to reflux for 16 h. After completion, the reaction mixture was concentrated under reduced pressure to get the crude compound which was extracted with water and EtOAc. The combined organic layers were dried over Na₂SO₄ and concentrated under reduced pressure to get the crude product which was purified by column chromatography (100-200 mesh silica gel; 2% MeOH-DCM; $R_f$-value-0.5) to afford trans-benzyl (5-oxo-2-phenylpyrrolidin-3-yl)carbamate (0.38 g, 50%).

Step 6: To a stirred solution of trans-benzyl (5-oxo-2-phenylpyrrolidin-3-yl)carbamate (1.7 g, 5.48 mmol, 1.0 eq) in MeOH (20 mL, 2:1), Pd/C (0.058 g, 0.548 mmol, 0.1 eq) was added, and the reaction was stirred with a hydrogen balloon for 2 h at RT. After completion, the reaction mixture was filtered through a celite bed and the celite bed was washed 2-3 times with EtOAc. The combined organic layers were concentrated to get the desired trans-4-amino-5-phenylpyrrolidin-2-one as brown gum (0.9 g, 93%).

Synthesis of (4S,5R)-4-amino-5-phenylpyrrolidin-2-one (Intermediate A2-ent2)

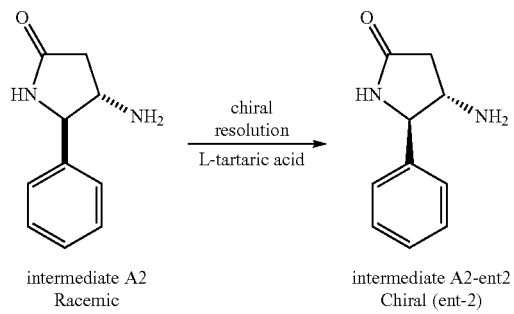

intermediate A2
Racemic intermediate A2-ent2
Chiral (ent-2)

To a stirred solution of trans-4-amino-5-phenyl-pyrrolidin-2-one (Intermediate A2) (10.0 g, 0.056 mol) in EtOH (180 mL) and acetonitrile (200 mL) was added L-tartaric acid (8.5 g, 0.056 mol) at RT. The resulting suspension was stirred at 90° C. for 1 h. To this refluxing suspension was slowly added water (110 mL). The resulting reaction mixture was maintained at 90° C. and was stirred for 4 h. The resulting clear solution was slowly cooled to RT and was allowed to stand at RT for 24 h. The solid thus precipitated was collected by filtration and washed with EtOH (100 mL) to afford 7.5 g of chiral (ent-2) as the corresponding L-tartrate salt. This solid material was treated with 1N aq. NaOH solution at RT. The resulting basic aqueous solution was then extracted with 10% MeOH in DCM (100 mL×5-6 times) to afford (4S,5R)-4-amino-5-phenyl-pyrrolidin-2-one (3 g, 60%) as a white solid (Intermediate A2-ent2).

Enantiomeric excess (ee) determined by chiral HPLC (Column Name: Chiralpak IA (4.6×250 mm), 5 μm; Mobile-Phase:Hexane/EtOH/IP amine: 80/20/0.1; Flow Rate: 1.0 ml/min; RT=25.0 min): ee=99.7%

Specific Rotation: [+29.9°] at 25° C., C=1% in EtOH.

Synthesis of (4R,5S)-4-amino-5-phenylpyrrolidin-2-one (Intermediate A2-ent1)

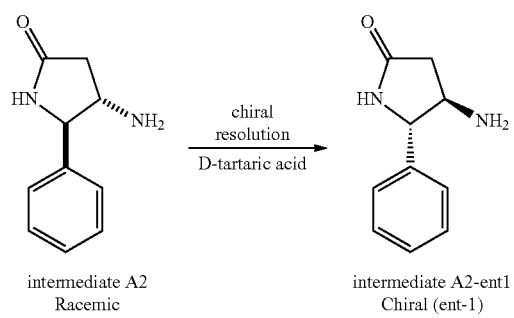

| intermediate A2 | intermediate A2-ent1 |
| --- | --- |
| Racemic | Chiral (ent-1) |

To a stirred solution of trans-4-amino-5-phenyl-pyrrolidin-2-one (Intermediate A2) (7.0 g, 39.77 mmol) in EtOH (126 mL) and acetonitrile (140 mL) was added D-tartaric acid (5.96 g, 39.77 mmol) at RT. The resulting suspension was stirred at 90° C. for 1 h. To this refluxing suspension was slowly added water (77 mL). The resulting reaction mixture was maintained at 90° C. for 4 h. The resulting clear solution was slowly cooled to RT and was allowed to stand at RT for 24 h. The solid thus precipitated was collected by filtration and washed with EtOH (70 mL) to afford 5.2 g of chiral (ent-1) as the corresponding D-tartrate salt as an off-white solid. (4R,5S)-4-amino-5-phenylpyrrolidin-2-one (2R,3R)-2,3-dihydroxysuccinate (5.2 g) was treated with 1N NaOH solution at RT. The resulting basic aqueous solution was then extracted with 10% MeOH in DCM (4×50 mL) to afford (4R,5S)-4-amino-5-phenylpyrrolidin-2-one (2.4 g, 34%) as a white solid.

Enantiomeric excess (ee) determined by chiral HPLC (Column Name: Chiralpak IA (4.6×250 mm), 5 µm; Mobile-Phase:Hexane/EtOH/IP amine: 80/20/0.1; Flow Rate: 1.0 ml/min; RT=17.65 min): ee=99.1%

Specific Rotation: [−34.5°] at 25° C., C=1.0% in EtOH.

Synthesis of trans-4-amino-5-(2,4-difluorophenyl)pyrrolidin-2-one (Intermediate A3)

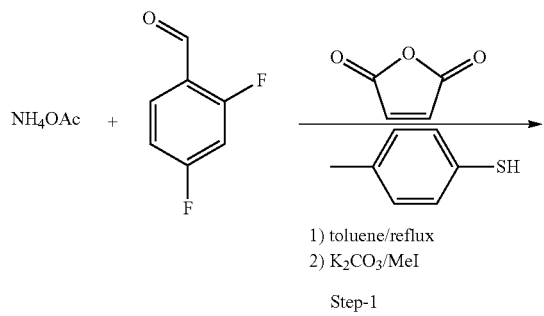

1) toluene/reflux
2) $K_2CO_3$/MeI

Step-1

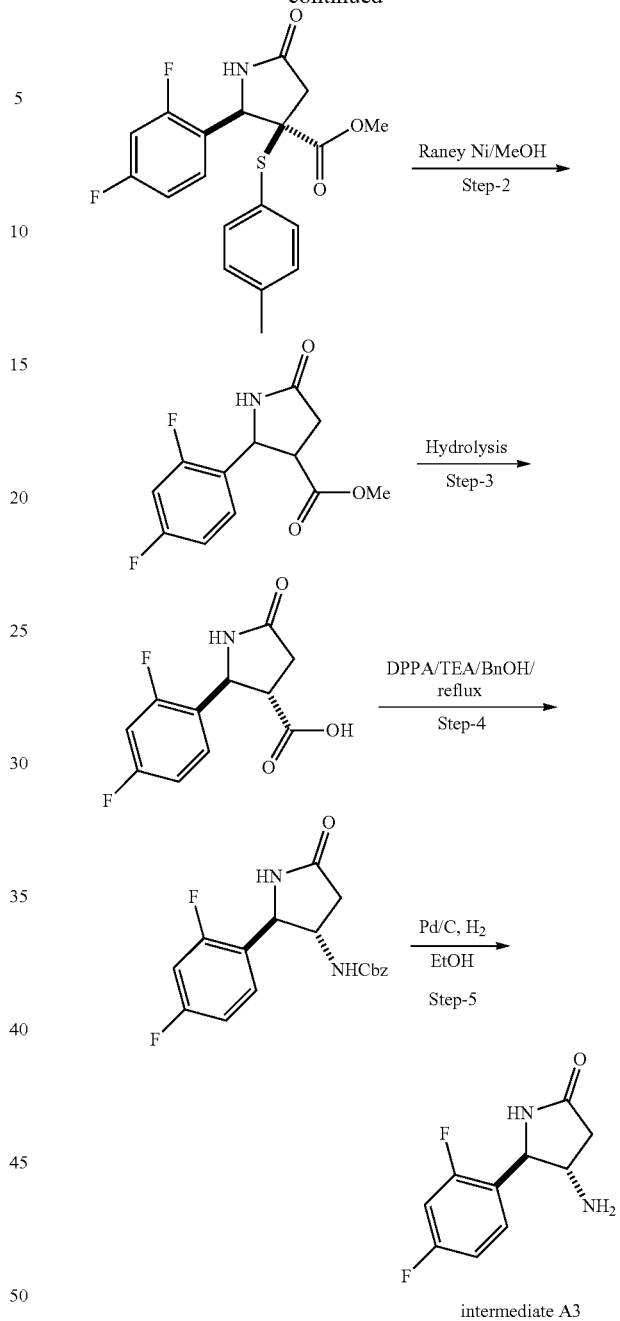

intermediate A3

Step 1: Maleic anhydride (28.9 g, 295.7 mmol, 1.0 eq), p-thiocresol (36.6 g, 295.7 mmol, 1.0 eq), ammonium acetate (22.7 g, 295.7 mmol, 1.0 eq), and 2,4-difluorobenzaldehyde (42.0 g, 295.7 mmol, 1.0 eq) were put in a sealed tube and 100 mL toluene was added. The reaction mixture was stirred at RT for 1 h and was then stirred at 150° C. for 16 h. After cooling to RT, the solvent was evaporated under reduced pressure, and the residue was basified with sat. $NaHCO_3$ solution and was extracted with DCM. The aqueous layer was acidified with 2N HCl under ice cooling and was then extracted twice with EtOAc. The combined organic layers were washed with brine, dried over $Na_2SO_4$, filtered, and concentrated to get the crude 3-((2,4-difluorophenyl)thio)-5-oxo-2-phenylpyrrolidine-3-carboxylic acid (120.0 g).

Step 2: To a stirred solution of crude 3-((2,4-difluorophenyl)thio)-5-oxo-2-phenylpyrrolidine-3-carboxylic acid (107.0 g, crude) in acetone (600 mL), potassium carbonate (162.7 g, 1170 mmol, 4.0 eq) and methyl iodide (73.3 mL, 1170 mmol, 4.0 eq) were added at 0° C., and the reaction mixture was stirred for 16 h at RT. The solvent was removed under reduced pressure, and the residue was partitioned between DCM and water. The aqueous layer was extracted twice with DCM. The combined organic layers were washed with brine, dried over Na$_2$SO$_4$, filtered and concentrated. The crude product was purified by column chromatography (100-200 silica gel, 50% EtOAc:hexanes) which gave methyl 3-((2,4-difluorophenyl)thio)-5-oxo-2-phenylpyrrolidine-3-carboxylate as an off white solid (6.0 g, 5%).

Step 3: To a stirred solution of methyl 3-((2,4-difluorophenyl)thio)-5-oxo-2-phenylpyrrolidine-3-carboxylate (6.0 g, 15.9 mmol, 1.0 eq) in EtOH:THF (225 mL, 2:1), Raney Nickel (60.0 g) was added and the reaction was stirred for 2 h at RT. After completion, the reaction mixture was filtered through a celite bed and the celite bed was washed 2-3 times with EtOAc. The combined organic layers were concentrated and the crude product was purified by column chromatography (100-200 silica gel, 50% EtOAc:hexanes) which gave methyl 2-(2,4-difluorophenyl)-5-oxopyrrolidine-3-carboxylate (2.8 g, 69%, syn:anti 1:1) as an off white solid.

Step 4: To a stirred solution of methyl 2-(2,4-difluorophenyl)-5-oxopyrrolidine-3-carboxylate (2.0 g, 7.84 mmol, 1.0 eq) in MeOH (47 mL) was added 2 N NaOH solution (12 mL) and the reaction mixture was stirred at 70° C. for 3 h. After completion of the reaction (monitored by LCMS), the reaction mixture was concentrated and acidified with 2N HCl solution and was then extracted with 30% isopropanol-DCM. The combined organic layers were dried over Na$_2$SO$_4$ and were concentrated under reduced pressure to get the desired trans-2-(2,4-difluorophenyl)-5-oxopyrrolidine-3-carboxylic acid (1.8 g, 95%).

Step 5: To a stirred solution of trans-2-(2,4-difluorophenyl)-5-oxopyrrolidine-3-carboxylic acid (1.8 g, 7.46 mmol, 1.0 eq) in benzene:THF (60 mL, 4:1) was added TEA (2.07 mL, 14.93 mmol, 2.0 eq) and DPPA (2.1 mL, 9.7 mmol, 1.3 eq) and the reaction mixture was stirred at ambient temperature for 2 h. Then benzyl alcohol (1.0 ml, 9.7 mmol, 1.3 eq) was added and the reaction mixture was heated to reflux for 16 h. After completion, the reaction mixture was concentrated under reduced pressure to get the crude which was extracted with water and EtOAc. The combined organic layers were dried over Na$_2$SO$_4$ and were concentrated under reduced pressure to get the crude product which was purified by flash column chromatography (100-200 mesh silica gel; 2% MeOH-DCM; R$_f$-value-0.5) to afford trans-benzyl (2-(2,4-difluorophenyl)-5-oxopyrrolidin-3-yl)carbamate (1.2 g, 46%) as an off-white solid.

Step 6: To a stirred solution of trans-benzyl (2-(2,4-difluorophenyl)-5-oxopyrrolidin-3-yl)carbamate (1.2 g, 3.46 mmol, 1.0 eq) in MeOH (15 mL), Pd/C (0.12 g, 10% w/w) was added, and the reaction was stirred with a hydrogen balloon for 2 h at RT. After completion, the reaction mixture was filtered through a celite bed and the celite bed was washed 2-3 times with EtOAc. The combined organic layers were concentrated to get the desired trans-4-amino-5-(2,4-difluorophenyl)pyrrolidin-2-one (0.85 g) as an off-white solid.

Synthesis of trans-4-amino-5-(2,3-dihydrobenzo[b][1,4]dioxin-6-yl)pyrrolidin-2-one (Intermediate A4)

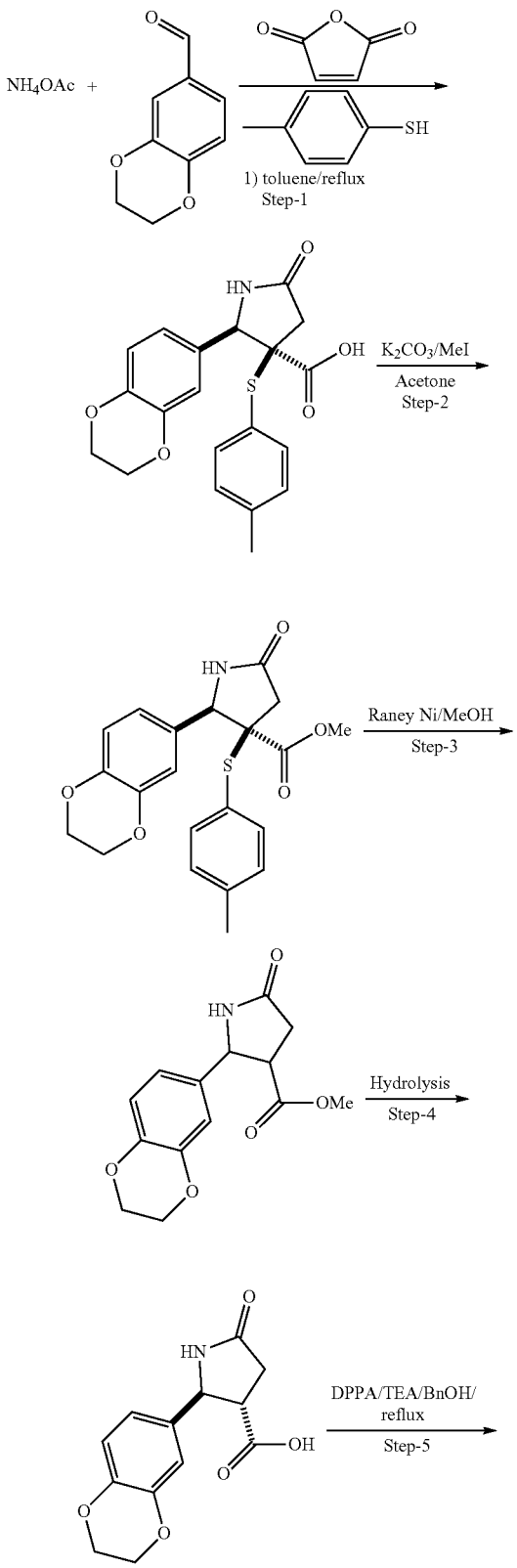

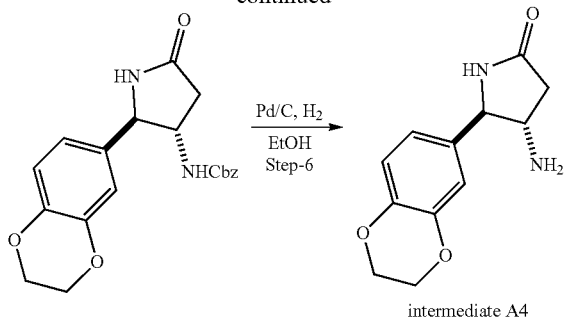

intermediate A4

Step 1: Maleic anhydride (5.97 g, 60.9 mmol, 1.0 eq), p-thiocresol (7.55 g, 60.9 mmol, 1.0 eq), ammonium acetate (4.68 g, 60.9 mmol, 1.0 eq), and 2,3-dihydro-1,4-benzodioxine-6-carbaldehyde (10.0 g, 60.9 mmol, 1.0 eq) were put in a sealed tube, followed by the addition of 80 mL of toluene. The reaction mixture was stirred at RT for 1 h and was then heated to 150° C. for 16 h. After cooling to RT, the solvent was evaporated under reduced pressure, and the residue was basified with sat. NaHCO$_3$ solution and was extracted with DCM. The aqueous layer was acidified with 2N HCl under ice cooling and was extracted twice with EtOAc. The combined organic layers were washed with brine, dried over Na$_2$SO$_4$, filtered and concentrated to get the crude 2-(2,3-dihydrobenzo[b][1,4]dioxin-6-yl)-5-oxo-3-(p-tolylthio)pyrrolidine-3-carboxylic acid (2.20 g).

Step 2: To a stirred solution of crude 2-(2,3-dihydrobenzo[b][1,4]dioxin-6-yl)-5-oxo-3-(p-tolylthio)pyrrolidine-3-carboxylic acid (2.2 g, 5.707 mmol, 1.0 eq) in acetone (100 mL), potassium carbonate (3.2 g, 22.831 mmol, 4.0 eq) and methyl iodide (1.42 mL, 22.831 mmol, 4.0 eq) were added at 0° C., and the reaction was stirred for 16 h at RT. The solvent was removed under reduced pressure, and the residue was partitioned between DCM and water. The aqueous layer was extracted twice with DCM. The combined organic layers were washed with brine, dried over Na$_2$SO$_4$, filtered and concentrated. The crude product was purified by column chromatography (100-200 silica gel, 50% EtOAc:hexanes) which gave methyl 2-(2,3-dihydrobenzo[b][1,4]dioxin-6-yl)-5-oxo-3-(p-tolylthio)pyrrolidine-3-carboxylate as an off white solid (0.9 g, 41%).

Step 3: To a stirred solution of methyl 2-(2,3-dihydrobenzo[b][1,4]dioxin-6-yl)-5-oxo-3-(p-tolylthio)pyrrolidine-3-carboxylate (0.9 g, 2.253 mmol, 1.0 eq) in EtOH:THF (60 mL, 2:1), Raney Nickel (1.0 g) was added, and the reaction was stirred for 2 h at RT. After completion, the reaction mixture was filtered through a celite bed and the celite bed was washed 2-3 times with EtOAc. The combined organic layers were concentrated and the crude remains were purified by column chromatography (100-200 silica gel, 50% EtOAc:hexanes) which gave methyl 2-(2,3-dihydrobenzo[b][1,4]dioxin-6-yl)-5-oxopyrrolidine-3-carboxylate (0.6 g, 96%, syn:anti: 1:1) as an off white solid.

Step 4: To a stirred solution of methyl 2-(2,3-dihydrobenzo[b][1,4]dioxin-6-yl)-5-oxopyrrolidine-3-carboxylate (0.7 g, 2.524 mmol, 1.0 eq) in MeOH (15 mL) was added a 2 N NaOH solution (3.7 mL) and the reaction mixture was stirred at 80° C. for 2 h. After completion of the reaction (monitored by LCMS), the reaction mixture was concentrated and acidified with 2N HCl solution and was then extracted with 30% isopropanol-DCM. The organic layer was dried over anhydrous Na$_2$SO$_4$ and concentrated under reduced pressure to get the desired trans-2-(2,3-dihydrobenzo[b][1,4]dioxin-6-yl)-5-oxopyrrolidine-3-carboxylic acid (0.5 g, 75%).

Step 5: To a stirred solution of trans-2-(2,3-dihydrobenzo[b][1,4]dioxin-6-yl)-5-oxopyrrolidine-3-carboxylic acid (0.3 g, 1.139 mmol, 1.0 eq) in benzene:THF (15 mL, 4:1) were added TEA (0.31 mL, 4.87 mmol, 2.0 eq) and DPPA (0.32 mL, 1.48 mmol, 1.3 eq) and the reaction mixture was stirred at RT for 2 h. Then benzyl alcohol (3 mL) was added and the reaction mixture was heated to reflux for 16 h. After completion, the reaction mixture was concentrated under reduced pressure to give the crude which was extracted with water and EtOAc. The organic layer was dried over anhydrous Na$_2$SO$_4$ and concentrated under reduced pressure to get the crude product which was purified by column chromatography (100-200 mesh silica gel; 2% MeOH-DCM; R$_f$-value-0.5) to afford trans-benzyl (-2-(2,3-dihydrobenzo[b][1,4]dioxin-6-yl)-5-oxopyrrolidin-3-yl)carbamate (0.2 g, 47%).

Step 6: To a stirred solution of trans-benzyl (-2-(2,3-dihydrobenzo[b][1,4]dioxin-6-yl)-5-oxopyrrolidin-3-yl)carbamate (0.32 g, 0.869 mmol, 1.0 eq) in MeOH:THF (20 mL, 2:1), Pd/C (50.0 mg) was added and the reaction was stirred with a hydrogen balloon for 2 h at RT. After completion, the reaction mixture was filtered through a celite bed and the celite bed was washed 2-3 times with EtOAc. The combined organic layer was concentrated to get the desired trans-4-amino-5-(2,3-dihydrobenzo[b][1,4]dioxin-6-yl)pyrrolidin-2-one (0.2 g, 98%) as brown gum.

Synthesis of trans-4-amino-5-(3-fluorophenyl)pyrrolidin-2-one (Intermediate A5)

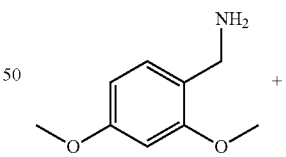

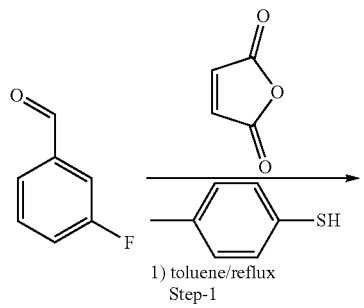

1) toluene/reflux
Step-1

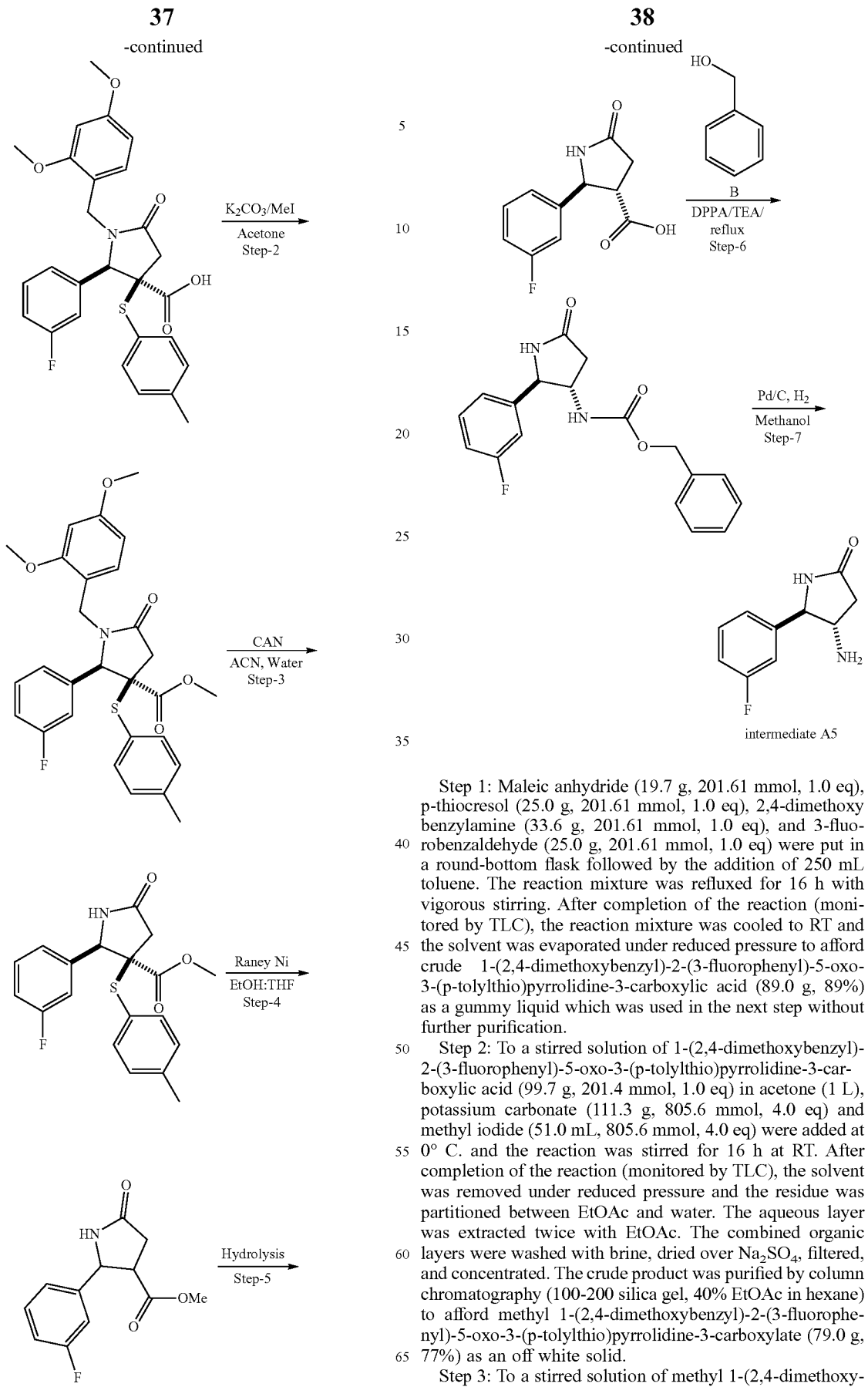

Step 1: Maleic anhydride (19.7 g, 201.61 mmol, 1.0 eq), p-thiocresol (25.0 g, 201.61 mmol, 1.0 eq), 2,4-dimethoxy benzylamine (33.6 g, 201.61 mmol, 1.0 eq), and 3-fluorobenzaldehyde (25.0 g, 201.61 mmol, 1.0 eq) were put in a round-bottom flask followed by the addition of 250 mL toluene. The reaction mixture was refluxed for 16 h with vigorous stirring. After completion of the reaction (monitored by TLC), the reaction mixture was cooled to RT and the solvent was evaporated under reduced pressure to afford crude 1-(2,4-dimethoxybenzyl)-2-(3-fluorophenyl)-5-oxo-3-(p-tolylthio)pyrrolidine-3-carboxylic acid (89.0 g, 89%) as a gummy liquid which was used in the next step without further purification.

Step 2: To a stirred solution of 1-(2,4-dimethoxybenzyl)-2-(3-fluorophenyl)-5-oxo-3-(p-tolylthio)pyrrolidine-3-carboxylic acid (99.7 g, 201.4 mmol, 1.0 eq) in acetone (1 L), potassium carbonate (111.3 g, 805.6 mmol, 4.0 eq) and methyl iodide (51.0 mL, 805.6 mmol, 4.0 eq) were added at 0° C. and the reaction was stirred for 16 h at RT. After completion of the reaction (monitored by TLC), the solvent was removed under reduced pressure and the residue was partitioned between EtOAc and water. The aqueous layer was extracted twice with EtOAc. The combined organic layers were washed with brine, dried over $Na_2SO_4$, filtered, and concentrated. The crude product was purified by column chromatography (100-200 silica gel, 40% EtOAc in hexane) to afford methyl 1-(2,4-dimethoxybenzyl)-2-(3-fluorophenyl)-5-oxo-3-(p-tolylthio)pyrrolidine-3-carboxylate (79.0 g, 77%) as an off white solid.

Step 3: To a stirred solution of methyl 1-(2,4-dimethoxybenzyl)-2-(3-fluorophenyl)-5-oxo-3-(p-tolylthio)pyrrolidine-3-carboxylate (78.0 g, 153.2 mmol, 1.0 eq) in acetonitrile (500 mL), was added CAN (251.9 g, 459.6 mmol, 3.0 eq) dissolved in water dropwise at 0° C. through an addition funnel. The reaction mixture was then stirred at RT for 16 h. After completion of the reaction (monitored by TLC), the reaction mixture was diluted with water and extracted twice with EtOAc. The combined organic layers were washed with brine, dried over $Na_2SO_4$, filtered and concentrated. The crude product was purified by column chromatography (230-400 silica gel, 40-50% EtOAc: hexane) to afford methyl 2-(3-fluorophenyl)-5-oxo-3-(p-tolylthio)pyrrolidine-3-carboxylate (47.0 g, 85%) as an off white solid.

Step 4: To a stirred solution of methyl 2-(3-fluorophenyl)-5-oxo-3-(p-tolylthio)pyrrolidine-3-carboxylate (30.0 g, 83.5 mmol, 1.0 eq) in EtOH:THF (500 mL:500 mL, 1:1), RaneyNickel (20.0 g) was added and the reaction was stirred under a hydrogen atmosphere for 16 h at RT. After completion (monitored by TLC) the reaction mixture was filtered through a celite bed and the celite bed was and washed 4-5 times with THF. The filtrate was concentrated to afford methyl 2-(3-fluorophenyl)-5-oxopyrrolidine-3-carboxylate (15.2 g, 77%, syn:anti mixture) as a white solid.

Step 5: To a stirred solution of methyl 2-(3-fluorophenyl)-5-oxopyrrolidine-3-carboxylate (16.0 g, 67.4 mmol, 1.0 eq) in MeOH (320 mL) was added 2 N NaOH solution (75 mL) and the reaction mixture was stirred at 80° C. for 16 h. After completion of the reaction (monitored by TLC) the reaction mixture was concentrated and acidified with 2N HCl solution to get a solid which was filtered off and was washed with diethyl ether, and was then dried under vacuum to afford trans-2-(3-fluorophenyl)-5-oxopyrrolidine-3-carboxylic acid (9.3 g, 62%).

Step 6: To a stirred solution of trans-2-(3-fluorophenyl)-5-oxopyrrolidine-3-carboxylic acid (13.0 g, 58.3 mmol, 1.0 eq) in toluene (130 mL) was added TEA (8.5 mL, 61.2 mmol, 1.05 eq) and DPPA (19.3 g, 70.0 mmol, 1.2 eq) and the reaction mixture was stirred at 90° C. for 30 min. Then benzyl alcohol (12.6 g, 116.6 mmol, 2.0 eq) was added and the reaction mixture was heated to reflux for 16 h. After completion (monitored by TLC), the reaction mixture was concentrated under reduced pressure. The residue was then diluted with EtOAc (100 mL), washed with water (2×100 mL), dried over anhydrous $Na_2SO_4$ and concentrated under reduced pressure to get the crude product which was purified by column chromatography (230-400 mesh silica gel; 0-2% MeOH in DCM) to afford trans-benzyl (2-(3-fluorophenyl)-5-oxopyrrolidin-3-yl)carbamate (7.0 g, 37%).

Step 7: To a stirred solution of trans-benzyl (2-(3-fluorophenyl)-5-oxopyrrolidin-3-yl)carbamate (7.0 g, 21.3 mmol, 1.0 eq) in MeOH (50 mL) and THF (20 mL), Pd—C (1.5 g, 14.9 mmol, 0.7 eq) was added and the reaction mixture was stirred with a hydrogen balloon for 2 h at RT. After completion (monitored by TLC), the reaction mixture was filtered through a celite bed and the celite bed was washed 2-3 times with THF. The filtrate was concentrated to get the desired trans-4-amino-5-(3-fluorophenyl)pyrrolidin-2-one (3.8 g, 92%) as a brown gum.

Synthesis of trans-4-amino-5-(2-fluorophenyl)pyrrolidin-2-one (Intermediate A6)

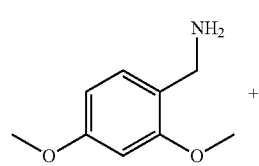
+

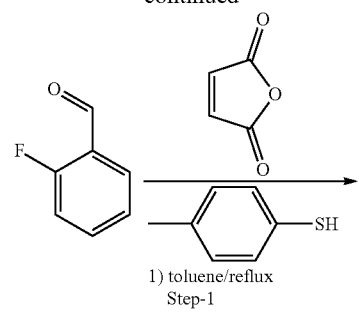
1) toluene/reflux
Step-1

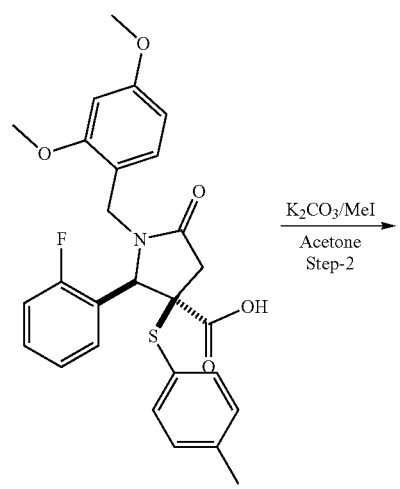
K₂CO₃/MeI
Acetone
Step-2

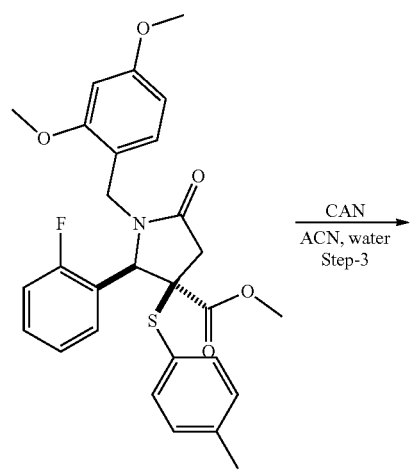
CAN
ACN, water
Step-3

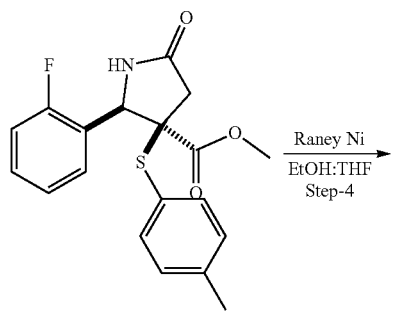
Raney Ni
EtOH:THF
Step-4

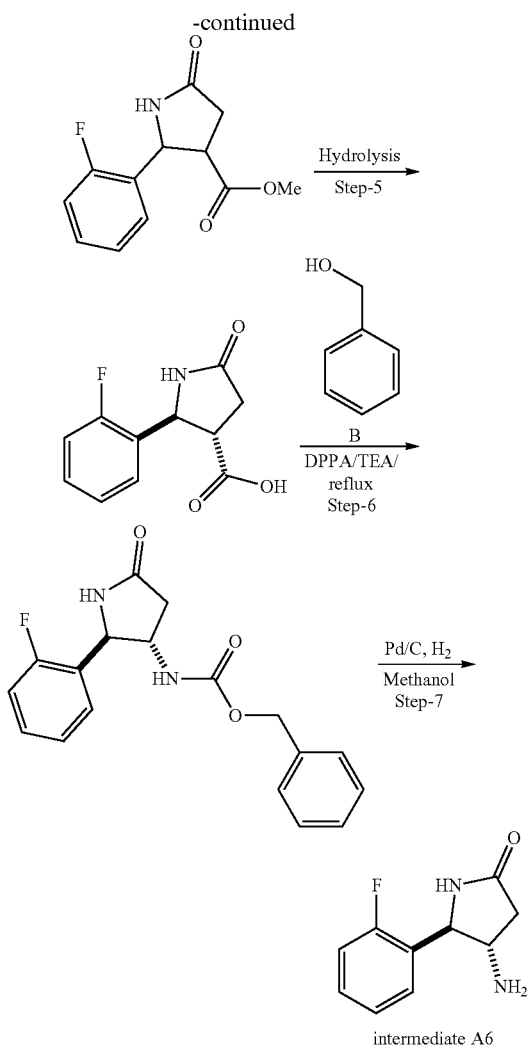

intermediate A6

Step 1: Maleic anhydride (19.7 g, 201.4 mmol, 1.0 eq), p-thiocresol (25.0 g, 201.4 mmol, 1.0 eq), 2,4 dimethoxy benzylamine (33.6 g, 201.4 mmol, 1.0 eq), and 2-fluorobenzaldehyde (25.0 g, 201.4 mmol, 1.0 eq) were taken up in 300 mL of toluene. The reaction mixture was refluxed for 16 h with vigorous stirring. After completion of the reaction (monitored by TLC, TLC system 5% MeOH in DCM, $R_f$-0.1), the reaction mixture was cooled to RT and the solvent was evaporated under reduced pressure to afford the crude 1-(2,4-dimethoxybenzyl)-2-(2-fluorophenyl)-5-oxo-3-(p-tolylthio)pyrrolidine-3-carboxylic acid as a gummy liquid (95.0 g, 95%) which was used in the next step without further purification.

Step 2: To a stirred solution of crude 1-(2,4-dimethoxy-benzyl)-2-(2-fluorophenyl)-5-oxo-3-(p-tolylthio)pyrrolidine-3-carboxylic acid (95.0 g, 191.7 mmol, 1.0 eq) in acetone (1 L), potassium carbonate (111.3 g, 805.0 mmol, 4.2 eq) and methyl iodide (50.0 mL, 805.0 mmol, 4.2 eq) were added at 0° C., and the reaction mixture was stirred at RT for 16 h. After completion of the reaction (monitored by TLC; TLC system 30% EtOAc in hexane, $R_f$-0.3), the solvent was removed under reduced pressure and the residue was partitioned between EtOAc and water. The aqueous layer was extracted twice with EtOAc. The combined organic layers were washed with brine, dried over $Na_2SO_4$, filtered and concentrated. The crude product was purified by column chromatography (100-200 silica gel, 40% EtOAc in hexane) to afford the desired methyl 1-(2,4-dimethoxybenzyl)-2-(2-fluorophenyl)-5-oxo-3-(p-tolylthio)pyrrolidine-3-carboxylate as an off white solid (55.0 g, 56%).

Step 3: To a stirred solution of methyl 1-(2,4-dimethoxybenzyl)-2-(2-fluorophenyl)-5-oxo-3-(p-tolylthio)pyrrolidine-3-carboxylate (55.0 g, 108.0 mmol, 1.0 eq) in acetonitrile (300 mL), CAN (178.0 g, 324.0 mmol, 3.0 eq) in water (300 mL) was added dropwise at 0° C. through an addition funnel. The reaction mixture was then stirred at RT for 16 h. After completion of the reaction (monitored by TLC, TLC system 50% EtOAc in hexane, $R_f$-0.3), the reaction mixture was diluted with water and extracted twice with EtOAc. The combined organic layers were washed with brine, dried over $Na_2SO_4$, filtered and concentrated. The crude product was purified by column chromatography (230-400 silica gel, 40-50% EtOAc: hexane) which gave methyl 2-(2-fluorophenyl)-5-oxo-3-(p-tolylthio)pyrrolidine-3-carboxylate as an off white solid (15.0 g, 39%).

Step 4: To a stirred solution of methyl 2-(2-fluorophenyl)-5-oxo-3-(p-tolylthio)pyrrolidine-3-carboxylate (15.0 g, 41.7 mmol, 1.0 eq) in EtOH:THF (300:300 mL, 1:1), Raney Nickel (15 g) was added, and the reaction was stirred under a hydrogen atmosphere for 16 h at RT. After completion, (monitored by TLC, TLC system 70% EtOAc in hexane, $R_f$-0.4) the reaction mixture was filtered through a celite bed and the celite bed was washed 4-5 times with THF. The filtrate was concentrated to afford methyl 2-(2-fluorophenyl)-5-oxopyrrolidine-3-carboxylate as a white solid (9.0 g, 91%; syn:anti mixture).

Step 5: To a stirred solution of methyl 2-(2-fluorophenyl)-5-oxopyrrolidine-3-carboxylate (9.0 g, 37.9 mmol, 1.0 eq) in MeOH (180 mL) was added 2 N NaOH solution (40 mL) and the reaction mixture was stirred at 80° C. for 16 h. After completion of the reaction (monitored by TLC, TLC system 5% MeOH in DCM, $R_f$-0.1), the reaction mixture was concentrated and acidified with 2N HCl solution to get a solid which was filtered off and was then washed with diethyl ether and dried under vacuum to afford trans-2-(2-fluorophenyl)-5-oxopyrrolidine-3-carboxylic acid (7.0 g, 83%).

Step 6: To a stirred solution of trans-2-(2-fluorophenyl)-5-oxopyrrolidine-3-carboxylic acid (7.0 g, 31.4 mmol, 1.00 eq) in Toluene (80 mL) was added TEA (4.6 mL, 33.0 mmol, 1.05 eq) and DPPA (10.4 g, 37.7 mmol, 1.2 eq) and the reaction mixture was stirred at 90° C. for 30 min. Then benzyl alcohol (6.8 g, 62.8 mmol, 2.0 eq) was added and the reaction mixture was heated to reflux for 16 h. After completion (monitored by TLC, TLC system 5% MeOH in DCM, Rf-0.3), the reaction mixture was concentrated under reduced pressure and was then diluted with EtOAc (100 mL), washed with water (2×100 mL), dried over $Na_2SO_4$ and concentrated under reduced pressure to get the crude product which was purified by column chromatography (230-400 mesh silica gel; 0-2% MeOH in DCM) to afford trans-benzyl (2-(2-fluorophenyl)-5-oxopyrrolidin-3-yl)carbamate (4.7 g, 46%).

Step 7: To a stirred solution of trans-benzyl (2-(2-fluorophenyl)-5-oxopyrrolidin-3-yl)carbamate (4.7 g, 14.3 mmol, 1.0 eq) in MeOH:THF (20 mL, 2:1), Pd/C (2.0 g, 10% moist) was added, and the reaction was stirred with a hydrogen balloon for 2 h at RT. After completion, (monitored by TLC, TLC system 5% MeOH in DCM, Rf-0.2), the reaction mixture was filtered through a celite bed and the celite bed was washed 2-3 times with THF. The filtrate was concentrated to get the desired trans-4-amino-5-(2-fluorophenyl) pyrrolidin-2-one as a brown gum (2.5 g, 90%).

Synthesis of trans-4-amino-5-(4-fluoro-3-methoxy-phenyl)pyrrolidin-2-one (Intermediate A7)

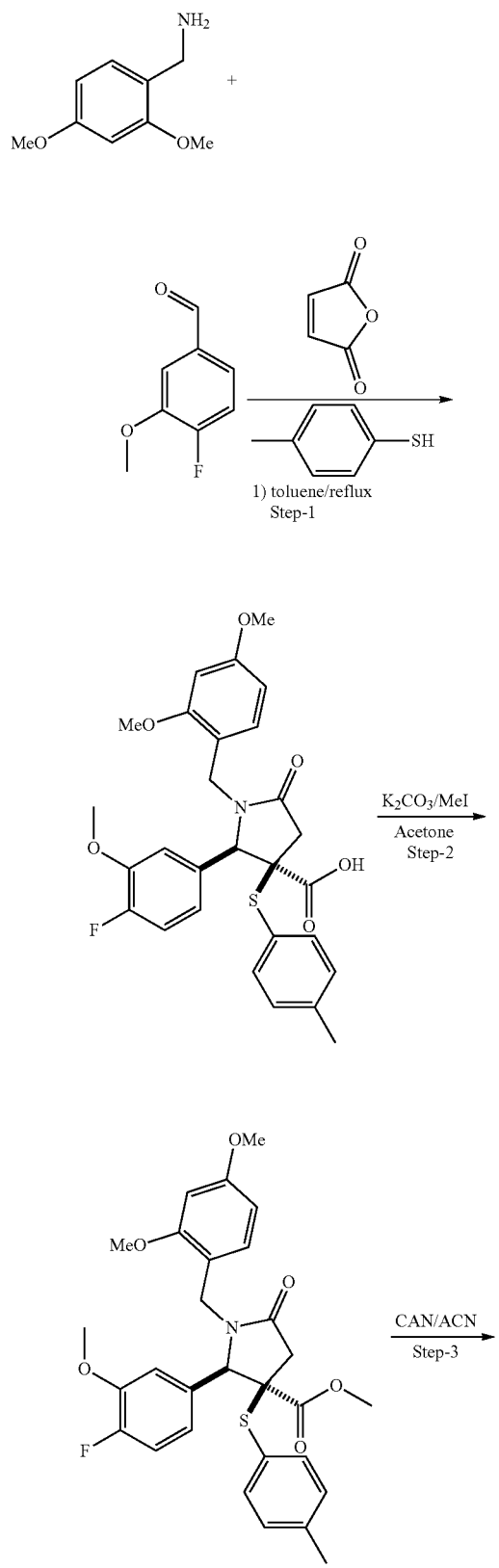

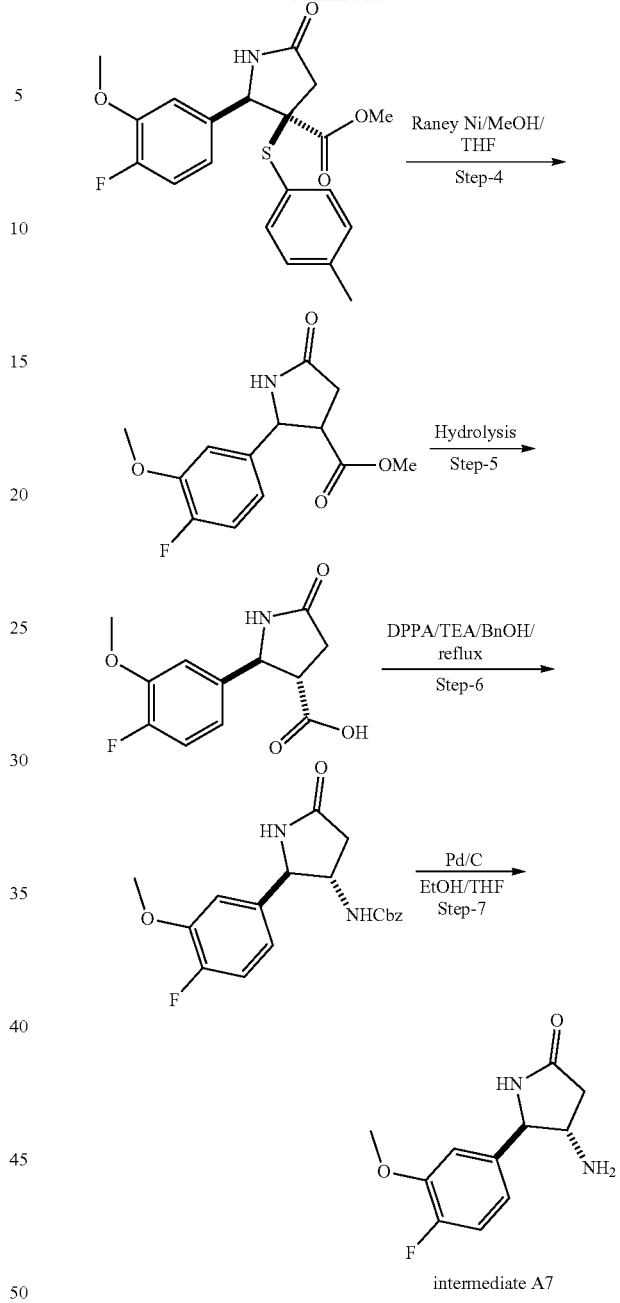

intermediate A7

Step 1: Maleic anhydride (14.6 g, 149.7 mmol, 1.0 eq), p-thiocresol (18.5 g, 149.7 mmol, 1.0 eq), 2,4-di-methoxy benzyl amine (25.0 g, 149.7 mmol, 1.0 eq), and 4-fluoro-3-methoxy benzaldehyde (23.0 g, 149.7 mmol, 1.0 eq) were dissolved in 500 mL toluene in a two neck round bottom flask fitted with a dean stark trap and a condenser. The reaction mixture was then heated to 150° C. for 16 h. After cooling to RT, the solvent was evaporated under reduced pressure to get the crude 1-(2,4-dimethoxybenzyl)-2-(4-fluoro-3-methoxyphenyl)-5-oxo-3-(p-tolylthio)pyrrolidine-3-carboxylic acid which was taken to the next step without further purification.

Step 2: To a stirred solution of crude 1-(2,4-dimethoxy-benzyl)-2-(4-fluoro-3-methoxyphenyl)-5-oxo-3-(p-tolyl-thio)pyrrolidine-3-carboxylic acid (max. 149.7 mmol, 1.0 eq) in acetone (500 mL), potassium carbonate (82.0 g, 598.0 mmol, 4.0 eq) and methyl iodide (37.5 mL, 598.0 mmol, 4.0 eq) were added at 0° C., and the reaction was stirred for 16 h at RT. The solvent was removed under reduced pressure, and the residue was partitioned between DCM and water. The aqueous layer was extracted twice with DCM. The combined organic layers were washed with brine, dried over Na$_2$SO$_4$, filtered and concentrated. The crude product was purified by column chromatography (100-200 silica gel, 50% EtOAc:hexanes) which gave methyl 1-(2,4-dimethoxybenzyl)-2-(4-fluoro-3-methoxyphenyl)-5-oxo-3-(p-tolylthio)pyrrolidine-3-carboxylate (72.0 g, 88%) as an off white solid.

Step 3: To a stirred solution of methyl 1-(2,4-dimethoxybenzyl)-2-(4-fluoro-3-methoxyphenyl)-5-oxo-3-(p-tolylthio)pyrrolidine-3-carboxylate (70.0 g, 129.0 mmol, 1.0 eq) in acetonitrile: water (500 mL 1:1), CAN was added at 0° C. and the reaction was stirred for 16 h at RT. The solvent was removed under reduced pressure, and the residue was partitioned between EtOAc and water. The aqueous layer was extracted twice with EtOAc. The combined organic layers were washed with brine, dried over Na$_2$SO$_4$, filtered and concentrated. The crude product was purified by column chromatography (100-200 silica gel, 50% EtOAc:hexanes) which gave methyl 2-(4-fluoro-3-methoxyphenyl)-5-oxo-3-(p-tolylthio)pyrrolidine-3-carboxylate (25.0 g, 50%) as an off white solid.

Step 4: To a stirred solution of methyl 2-(4-fluoro-3-methoxyphenyl)-5-oxo-3-(p-tolylthio)pyrrolidine-3-carboxylate (15.0 g, 64.3 mmol, 1.0 eq) in EtOH:THF (300 mL, 2:1), Raney Nickel (5.0 g) was added, and the reaction was stirred for 2 h at RT. After completion, the reaction mixture was filtered through a celite bed and washed 2-3 times with EtOAc. The combined organic layers were concentrated and the crude product was purified by column chromatography (100-200 silica gel, 50% EtOAc:hexanes) which gave methyl 2-(4-fluoro-3-methoxyphenyl)-5-oxopyrrolidine-3-carboxylate (10.0 g, 98%, syn:anti, 1:1 mixture) as an off white solid.

Step 5: To a stirred solution of methyl 2-(4-fluoro-3-methoxyphenyl)-5-oxopyrrolidine-3-carboxylate (10.0 g, 37.5 mmol, 1.0 eq) in MeOH (250 mL) was added 2 N NaOH solution (50 mL) and the reaction mixture was stirred at 80° C. for 2 h. After completion of the reaction (monitored by LCMS), the reaction mixture was concentrated, acidified with 2N HCl solution and then extracted with 30% isopropanol-DCM. The combined organic layers were dried over anhydrous Na$_2$SO$_4$ and concentrated under reduced pressure to get the desired trans-2-(4-fluoro-3-methoxyphenyl)-5-oxopyrrolidine-3-carboxylic acid (8.0 g, 84%).

Step 6: To a stirred solution of trans-2-(4-fluoro-3-methoxyphenyl)-5-oxopyrrolidine-3-carboxylic acid (2.0 g, 7.90 mmol, 1.0 eq) in benzene:THF (100 mL, 4:1) was added TEA (2.2 mL, 15.81 mmol, 2.0 eq) and DPPA (2.2 mL, 10.27 mmol, 1.3 eq) and the reaction mixture was stirred at RT for 2 h. Then benzyl alcohol (1.0 mL, 10.27 mmol, 1.3 eq) was added to the reaction mixture and heated to reflux for 16 h. After completion, reaction mixture was concentrated under reduced pressure to get the crude which was extracted with water and EtOAc. Organic layer was dried over anhydrous Na$_2$SO$_4$ and concentrated under reduced pressure to get the crude product which was purified by column chromatography (100-200 mesh silica gel; 2% MeOH-DCM; R$_f$-value-0.5) to afford trans-benzyl (2-(4-fluoro-3-methoxyphenyl)-5-oxopyrrolidin-3-yl)carbamate (1.4 g, 50%).

Step 7: To a stirred solution of trans-benzyl (2-(4-fluoro-3-methoxyphenyl)-5-oxopyrrolidin-3-yl)carbamate (7 g, 19.55 mmol, 1 eq) in MeOH:THF (20 mL, 2:1), Pd—C(0.7 g) was added, and the reaction was stirred for 2 h at RT. After completion, the reaction mixture was filtered through celite bed and washed 2-3 times with EtOAc. The combined organic layer was concentrated to get trans-4-amino-5-(4-fluoro-3-methoxyphenyl)pyrrolidin-2-one (4 g, 91%) as brown gum.

Synthesis of trans-4-amino-5-(4-fluorophenyl)pyrrolidin-2-one (Intermediate A8)

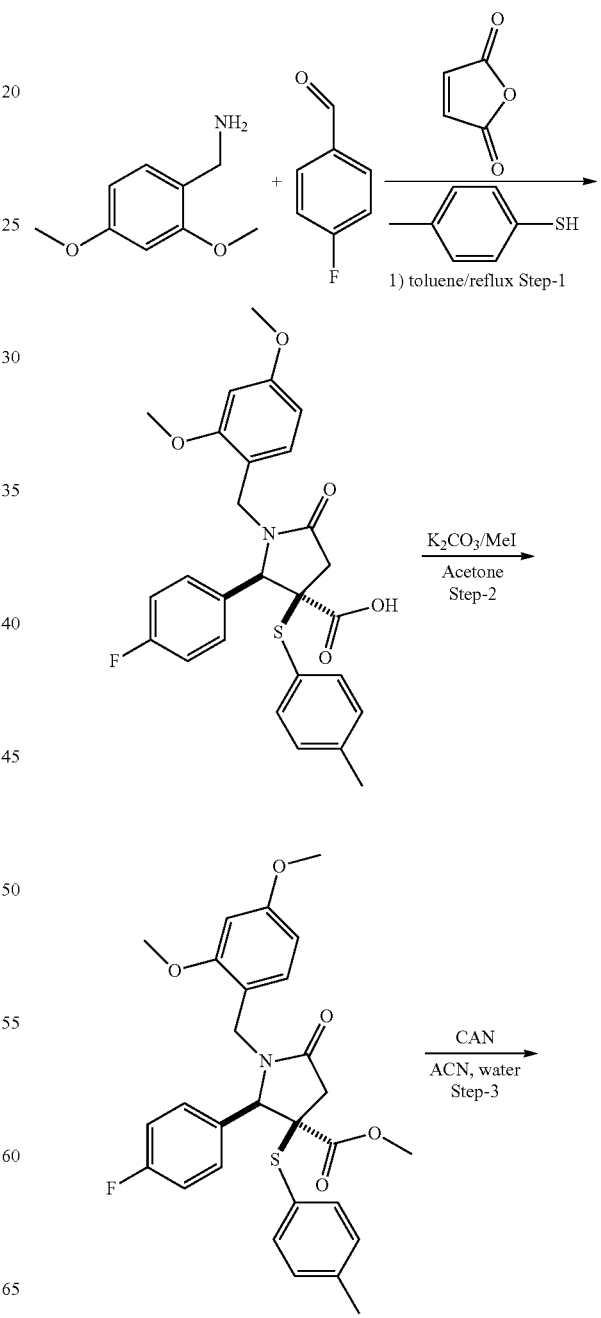

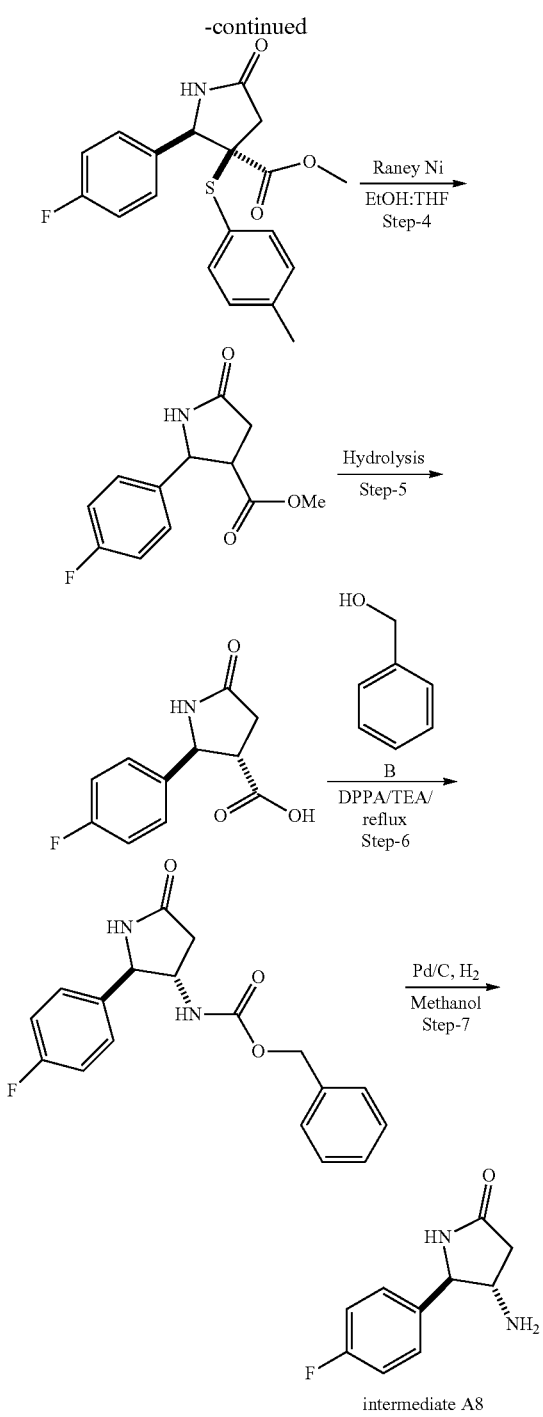

Step 1: Maleic anhydride (19.7 g, 201.6 mmol, 1.0 eq), p-thiocresol (25.0 g, 201.6 mmol, 1.0 eq), 2,4 dimethoxy benzylamine (33.6 g, 201.6 mmol, 1.0 eq), and 4-fluorobenzaldehyde (25.0 g, 201.6 mmol, 1.0 eq) were taken up in 250 mL toluene. The reaction mixture was refluxed for 16 h with vigorous stirring. After completion of the reaction (monitored by TLC, TLC system 5% MeOH in DCM, $R_f$-0.1), the reaction mixture was cooled to RT and the solvent was evaporated under reduced pressure to give crude 1-(2,4-dimethoxybenzyl)-2-(4-fluorophenyl)-5-oxo-3-(p-tolylthio)pyrrolidine-3-carboxylic acid (92.0 g, 92%) as a gummy liquid, which was used in the next step without further purification.

Step 2: To a stirred solution of crude 1-(2,4-dimethoxybenzyl)-2-(4-fluorophenyl)-5-oxo-3-(p-tolylthio)pyrrolidine-3-carboxylic acid (92.0 g, 201.4 mmol, 1.0 eq) in acetone (1 L), potassium carbonate (111.3 g, 805.6 mmol, 4.0 eq) and methyl iodide (50.0 mL, 805.6 mmol, 4.0 eq) were added at 0° C. and the reaction was stirred for 16 h at RT. After completion of the reaction (monitored by TLC), the solvent was removed under reduced pressure and the residue was partitioned between EtOAc and water. The aqueous layer was extracted twice with EtOAc. The combined organic layers were washed with brine, dried over Na$_2$SO$_4$, filtered and concentrated. The crude product was purified by column chromatography (100-200 silica gel, 40% EtOAc in hexane) to afford methyl 1-(2,4-dimethoxybenzyl)-2-(4-fluorophenyl)-5-oxo-3-(p-tolylthio)pyrrolidine-3-carboxylate (79.0 g, 84%) as an off white solid.

Step 3: To a stirred solution of methyl 1-(2,4-dimethoxybenzyl)-2-(4-fluorophenyl)-5-oxo-3-(p-tolylthio)pyrrolidine-3-carboxylate (92.0 g, 180.7 mmol, 1.0 eq) in acetonitrile, CAN (297.0 g, 542.1 mmol, 3.0 eq) in water was added dropwise to the reaction mixture at 0° C. through an addition funnel. The reaction was then stirred at RT for 16 h. After completion of the reaction (monitored by TLC, TLC system 50% EtOAc in hexane, Rf-0.3), the reaction mixture was diluted with water and extracted twice with EtOAc. The combined organic layers were washed with brine, dried over Na$_2$SO$_4$, filtered and concentrated. The crude product was purified by column chromatography (230-400 silica gel, 40-50% EtOAc: hexane) which gave methyl 2-(4-fluorophenyl)-5-oxo-3-(p-tolylthio)pyrrolidine-3-carboxylate (41.0 g, 63%) as an off white solid.

Step 4: To a stirred solution of methyl 2-(4-fluorophenyl)-5-oxo-3-(p-tolylthio)pyrrolidine-3-carboxylate (13.0 g, 36.2 mmol, 1.0 eq) in EtOH:THF (260:130 mL, 2:1), Raney Nickel (13.0 g) was added and the reaction mixture was stirred under a hydrogen atmosphere for 16 h at RT. After completion of the reaction (monitored by TLC), the reaction mixture was filtered through a celite bed and the celite bed was washed 4-5 times with THF. The filtrate was concentrated to give methyl 2-(4-fluorophenyl)-5-oxopyrrolidine-3-carboxylate (6.7 g, 78%, syn:anti mixture) as a white solid.

Step 5: To a stirred solution of methyl 2-(4-fluorophenyl)-5-oxopyrrolidine-3-carboxylate (10.0 g, 42.2 mmol, 1.0 eq) in MeOH (200 mL) was added 2N NaOH solution (48 mL) and the reaction mixture was stirred at 80° C. for 16 h. After completion of the reaction (monitored by TLC, TLC system 5% MeOH in DCM, $R_f$-0.1), the reaction mixture was concentrated and acidified with 2N HCl solution to obtain a solid which was filtered and washed with diethyl ether, followed by drying under vacuum to afford trans 2-(4-fluorophenyl)-5-oxopyrrolidine-3-carboxylic acid (6.4 g, 68%).

Step 6: To a stirred solution of trans 2-(4-fluorophenyl)-5-oxopyrrolidine-3-carboxylic acid (5.0 g, 22.4 mmol, 1.00 eq) in toluene (50 mL) was added TEA (3.3 mL, 23.5 mmol, 1.05 eq) and DPPA (7.4 g, 26.9 mmol, 1.20 eq) and the reaction mixture was heated to 90° C. for 30 min. Then benzyl alcohol (4.8 g, 44.8 mmol, 2.00 eq) was added and the reaction mixture was heated to reflux for 16 h. After completion (monitored by TLC), the reaction mixture was concentrated under reduced pressure. The residue was then diluted with EtOAc (100 mL), washed with water (2×100 mL), dried over Na$_2$SO$_4$ and finally concentrated under reduced pressure to get the crude product which was purified by column chromatography (230-400 mesh silica gel; 0-2%

MeOH in DCM) to afford trans-benzyl (2-(4-fluorophenyl)-5-oxopyrrolidin-3-yl)carbamate (4.1 g, 56%).

Step 7: To a stirred solution of trans-benzyl (2-(4-fluorophenyl)-5-oxopyrrolidin-3-yl)carbamate (2.0 g, 6.1 mmol, 1.0 eq) in MeOH (50 mL) and THF (20 mL), Pd/C (0.3 g, 3.0 mmol, 0.5 eq) was added and the reaction was stirred with a hydrogen balloon for 2 h at RT. After completion (monitored by TLC), the reaction mixture was filtered through a celite bed and the celite bed was washed 2-3 times with THF. The filtrate was concentrated to get the desired trans4-amino-5-(4-fluorophenyl)pyrrolidin-2-one (1.1 g, 93%) as a brown gum.

Synthesis of trans-4-amino-5-(2-methoxypyridin-4-yl)pyrrolidin-2-one (Intermediate A9)

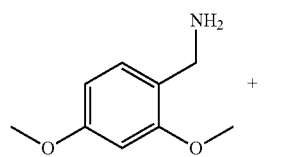

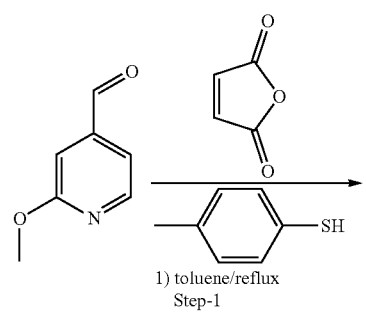

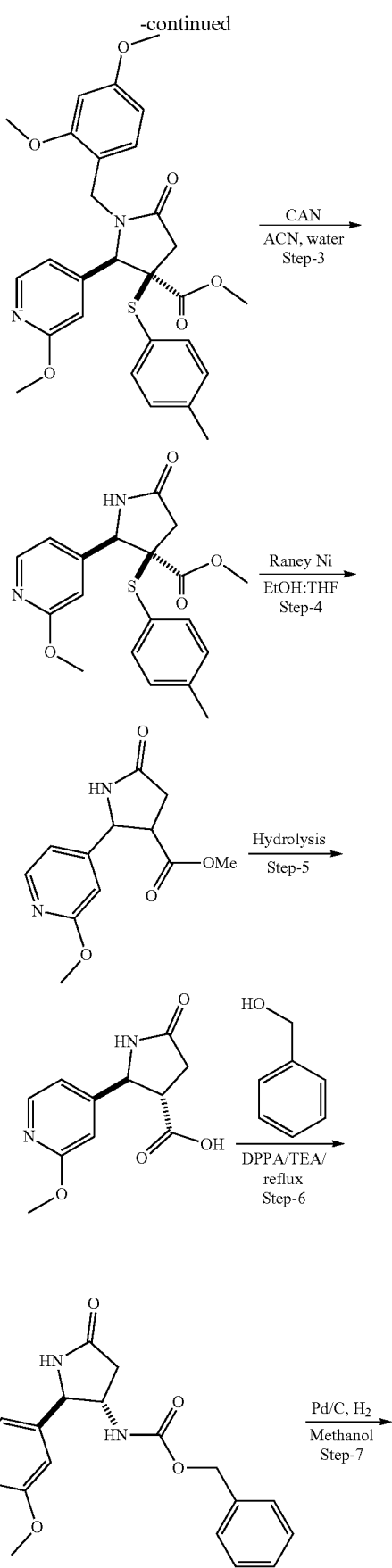

-continued

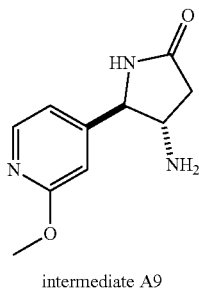

intermediate A9

Step 1: Maleic anhydride (17.2 g, 175.0 mmol, 1.0 eq), p-thiocresol (21.7 g, 175.0 mmol, 1.0 eq), 2,4-dimethoxy benzylamine (29.2 g, 175.0 mmol, 1.0 eq), and 2-methoxy-pyridine-4-carbaldehyde (24.0 g, 175.0 mmol, 1.0 eq) were taken up in 300 mL of toluene. The reaction mixture was refluxed for 16 h with vigorous stirring. After completion of the reaction (monitored by TLC, TLC system 5% MeOH in DCM, $R_f$-0.1), the reaction mixture was cooled to RT and the solvent was evaporated under reduced pressure to afford the crude 1-(2,4-dimethoxybenzyl)-2-(2-methoxypyridin-4-yl)-5-oxo-3-(p-tolylthio)pyrrolidine-3-carboxylic acid as a gummy liquid (80.0 g) which was used in the next step without further purification.

Step 2: To a stirred solution of 1-(2,4-dimethoxybenzyl)-2-(2-methoxypyridin-4-yl)-5-oxo-3-(p-tolylthio)pyrrolidine-3-carboxylic acid (57.0 g, 112.1 mmol, 1.0 eq) in acetone (300 mL), potassium carbonate (61.9 g, 448.3 mmol, 4.0 eq) and methyl iodide (28.0 mL, 448.3 mmol, 4.0 eq) were added at 0° C., and the reaction was stirred at RT for 16 h. After completion of the reaction (monitored by TLC, TLC system 30% EtOAc in hexane, $R_f$-0.3), the solvent was removed under reduced pressure and the residue was partitioned between EtOAc and water. The aqueous layer was extracted twice with EtOAc. The combined organic layers were washed with brine, dried over $Na_2SO_4$, filtered and concentrated. The crude product was purified by column chromatography (100-200 silica gel, 40% EtOAc in hexane) to afford methyl 1-(2,4-dimethoxybenzyl)-2-(2-methoxypyridin-4-yl)-5-oxo-3-(p-tolylthio)pyrrolidine-3-carboxylate as an off white solid (35.0 g, 60%).

Step 3: To a stirred solution of methyl 1-(2,4-dimethoxy-benzyl)-2-(2-methoxypyridin-4-yl)-5-oxo-3-(p-tolylthio) pyrrolidine-3-carboxylate (60.0 g, 114.8 mmol, 1.0 eq) in acetonitrile (300 mL), CAN (188.8 g, 344.4 mmol, 3.0 eq) in water (300 mL) was added dropwise at 0° C. through an addition funnel and the reaction mixture was then stirred at RT for 16 h. After completion of the reaction (monitored by TLC, TLC system 70% EtOAc in hexane, Rf-0.3), the reaction mixture was diluted with water and extracted twice with EtOAc. The combined organic layers were washed with brine, dried over $Na_2SO_4$, filtered and concentrated. The crude product was purified by column chromatography (230-400 silica gel, 40-50% EtOAc:hexane) to give methyl 2-(2-methoxypyridin-4-yl)-5-oxo-3-(p-tolylthio)pyrrolidine-3-carboxylate as an off white solid (12.0 g, 28%).

Step 4: To a stirred solution of methyl 2-(2-methoxypyridin-4-yl)-5-oxo-3-(p-tolylthio)pyrrolidine-3-carboxylate (11.4 g, 30.6 mmol, 1.0 eq) in EtOH:THF (50:100 mL, 1:2), Raney Nickel (18 g) was added, and the reaction was stirred under a hydrogen atmosphere for 16 h at RT. After completion, (monitored by TLC, TLC system 70% EtOAc in hexane, Rf-0.4) the reaction mixture was filtered through a celite bed and the celite bed was washed 4-5 times with THF.

The filtrate was concentrated to afford methyl 2-(2-methoxy-pyridin-4-yl)-5-oxopyrrolidine-3-carboxylate as a white solid (7.1 g, 93%, syn:anti mixture).

Step 5: To a stirred solution of methyl 2-(2-methoxypyridin-4-yl)-5-oxopyrrolidine-3-carboxylate (0.7 g, 2.8 mmol, 1 eq) in MeOH (10 mL) was added 2N NaOH solution (6 mL) and the reaction mixture was stirred at 80° C. for 16 h. After completion of the reaction (monitored by TLC, TLC system 5% MeOH in DCM, Rf-0.1), the reaction mixture was concentrated and acidified with 2N HCl solution to get a solid which was filtered off and was washed with diethyl ether. After drying under vacuum trans-2-(2-methoxypyridin-4-yl)-5-oxopyrrolidine-3-carboxylic acid was obtained (0.4 g, 61%).

Step 6: To a stirred solution of trans-2-(2-methoxypyridin-4-yl)-5-oxopyrrolidine-3-carboxylic acid (0.37 g, 1.58 mmol, 1.00 eq) in toluene (20 mL) was added TEA (0.30 mL, 1.66 mmol, 1.05 eq) and DPPA (0.40 mL, 1.89 mmol, 1.20 eq) and the reaction mixture was stirred at 90° C. for 30 min. Then benzyl alcohol (0.40 mL, 3.16 mmol, 2.00 eq) was added to the reaction mixture and heated to reflux for 16 h. After completion, (monitored by TLC, TLC system 5% MeOH in DCM, Rf-0.3), the reaction mixture was concentrated under reduced pressure. The residue was then diluted with EtOAc (100 mL), washed with water (2×100 mL), dried over $Na_2SO_4$ and concentrated under reduced pressure to get the crude product which was purified by column chromatography (230-400 mesh silica gel; 0-2% MeOH in DCM) to afford trans-benzyl (2-(2-methoxypyridin-4-yl)-5-oxopyrrolidin-3-yl)carbamate (0.20 g, 37%).

Step 7: To a stirred solution of trans-benzyl (2-(2-methoxypyridin-4-yl)-5-oxopyrrolidin-3-yl)carbamate (0.2 g, 24.0 mmol, 1.0 eq) in MeOH:THF (20 mL, 2:1), Pd/C (0.2 g, 10%, moist) was added and the reaction was stirred with a hydrogen balloon for 2 h at RT. After completion, (monitored by TLC, TLC system 5% MeOH in DCM, Rf-0.2), the reaction mixture was filtered through a celite bed and the celite bed was washed 2-3 times with THF. The filtrate was concentrated to get trans-4-amino-5-(2-methoxypyridin-4-yl)pyrrolidin-2-one as a brown gum (0.1 g, 82%).

Synthesis of trans-4-amino-5-(o-tolyl)pyrrolidin-2-one (Intermediate A10)

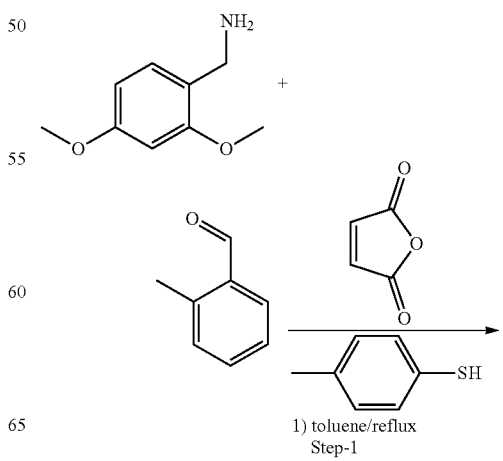

1) toluene/reflux
Step-1

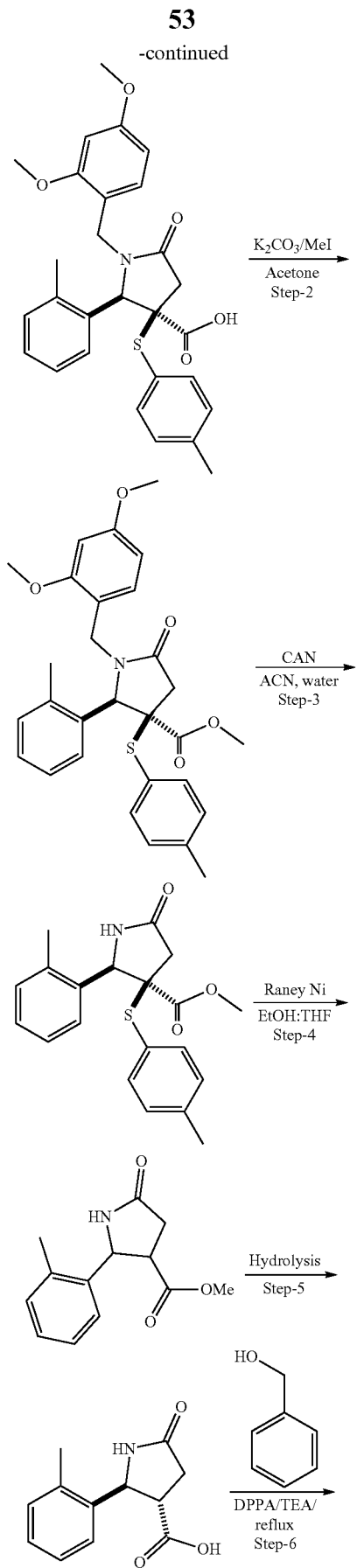

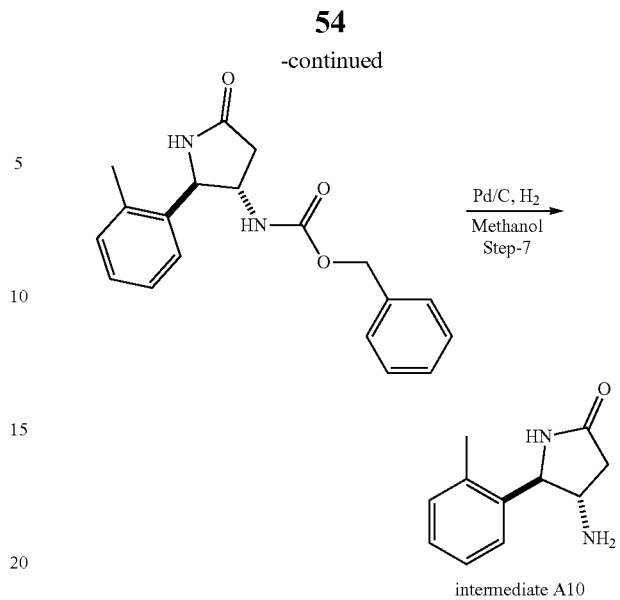

intermediate A10

Step 1: Maleic anhydride (20.3 g, 208.2 mmol, 1.0 eq), p-thiocresol (25.8 g, 208.2 mmol, 1.0 eq), 2,4-dimethoxy benzylamine (34.7 g, 208.2 mmol, 1.0 eq), and 2-fluorobenzaldehyde (25.0 g, 208.2 mmol, 1.0 eq) were taken up in 300 mL of toluene. The reaction mixture was refluxed for 16 h with vigorous stirring. After completion of the reaction (monitored by TLC, TLC system 5% MeOH in DCM, $R_f$-0.1), the reaction mixture was cooled to RT and the solvent was evaporated under reduced pressure to afford the crude 1-(2,4-dimethoxybenzyl)-5-oxo-2-(o-tolyl)-3-(p-tolylthio)pyrrolidine-3-carboxylic acid as a gummy liquid (101.0 g) which was used in the next step without further purification.

Step 2: To a stirred solution of crude 1-(2,4-dimethoxybenzyl)-5-oxo-2-(o-tolyl)-3-(p-tolylthio)pyrrolidine-3-carboxylic acid (101.0 g, 208.2 mmol, 1.0 eq) in acetone (1 L), potassium carbonate (115.0 g, 832.8 mmol, 4.0 eq) and methyl iodide (52.0 mL, 832.8 mmol, 4.0 eq) were added at 0° C. and the reaction was stirred at RT for 16 h. After completion of the reaction (monitored by TLC, TLC system 30% EtOAc in hexane, $R_f$-0.3) the solvent was removed under reduced pressure and the residue was partitioned between EtOAc and water. The aqueous layer was extracted twice with EtOAc. The combined organic layers were washed with brine, dried over $Na_2SO_4$, filtered and concentrated. The crude product was purified by column chromatography (100-200 silica gel, 40% EtOAc in hexane) to afford methyl 1-(2,4-dimethoxybenzyl)-5-oxo-2-(o-tolyl)-3-(p-tolylthio)pyrrolidine-3-carboxylate as an off white solid (80.0 g, 76%).

Step 3: To a stirred solution of methyl 1-(2,4-dimethoxybenzyl)-5-oxo-2-(o-tolyl)-3-(p-tolylthio)pyrrolidine-3-carboxylate (80.0 g, 158.0 mmol, 1.0 eq) in acetonitrile (300 mL), CAN (260.0 g, 475.0 mmol, 3.0 eq) in water (300 mL) was added dropwise to the reaction mixture at 0° C. through an addition funnel and the reaction mixture was stirred at RT for 16 h. After completion of the reaction (monitored by TLC, TLC system 50% EtOAc in hexane, Rf-0.3), the reaction mixture was diluted with water and extracted twice with EtOAc. The combined organic layers were washed with brine, dried over $Na_2SO_4$, filtered and concentrated. The crude product was purified by column chromatography (230-400 silica gel, 40-50% EtOAc: hexane) which gave methyl 5-oxo-2-(o-tolyl)-3-(p-tolylthio)pyrrolidine-3-carboxylate as an off white solid (21.5 g, 38%).

Step 4: To a stirred solution of methyl 5-oxo-2-(o-tolyl)-3-(p-tolylthio)pyrrolidine-3-carboxylate (21.5 g, 60.5 mmol, 1.0 eq) in EtOH:THF (300:300 mL, 1:1), Raney Nickel (~18 g) was added, and the reaction was stirred under a hydrogen atmosphere for 16 h at RT. After completion, (monitored by TLC, TLC system 70% EtOAc in hexane, Rf-0.4) the reaction mixture was filtered through a celite bed and the celite bed was washed 4-5 times with THF. The filtrate was concentrated to afford methyl 5-oxo-2-(o-tolyl)pyrrolidine-3-carboxylate as a white solid (11.5 g, 82%, syn:anti mixture).

Step 5: To a stirred solution of methyl 5-oxo-2-(o-tolyl) pyrrolidine-3-carboxylate (11.5 g, 49.3 mmol, 1.0 eq) in MeOH (400 mL) was added 2N NaOH solution (80 mL) and the reaction mixture was stirred at 80° C. for 16 h. After completion of the reaction (monitored by TLC, TLC system 5% MeOH in DCM, Rf-0.1), the reaction mixture was concentrated and acidified with 2N HCl solution to get a solid which was filtered off and was washed with diethyl ether. Drying under vacuum then afforded trans-5-oxo-2-(o-tolyl)pyrrolidine-3-carboxylic acid (8.5 g, 79%).

Step 6: To a stirred solution of trans-5-oxo-2-(o-tolyl) pyrrolidine-3-carboxylic acid (8.5 g, 38.0 mmol, 1.00 eq) in toluene (110 mL) were added TEA (5.5 mL, 39.9 mmol, 1.05 eq) and DPPA (10.5 g, 45.0 mmol, 1.20 eq) and the reaction mixture was stirred at 90° C. for 30 min. After 30 min, benzyl alcohol (8.4 g, 77.0 mmol, 2.00 eq) was added and the reaction mixture was heated to reflux for 16 h. After completion (monitored by TLC, TLC system 5% MeOH in DCM, Rf-0.3), the reaction mixture was concentrated under reduced pressure. The residue was then diluted with EtOAc (100 mL), washed with water (2×100 mL), dried over anhydrous Na$_2$SO$_4$ and was then concentrated under reduced pressure to get the crude product which was purified by column chromatography (230-400 mesh silica gel; 0-2% MeOH in DCM) to afford trans-benzyl (5-oxo-2-(o-tolyl) pyrrolidin-3-yl)carbamate (8.0 g, 65%).

Step 7: To a stirred solution of trans-benzyl (5-oxo-2-(o-tolyl)pyrrolidin-3-yl)carbamate (8.0 g, 24.0 mmol, 1.0 eq) in MeOH:THF (20 mL, 2:1), Pd/C (2.0 g, 10%, moist) was added, and the reaction mixture was stirred with a hydrogen balloon for 2 h at RT. After completion, (monitored by TLC, TLC system 5% MeOH in DCM, Rf-0.2), the reaction mixture was filtered through a celite bed and the celite bed was washed 2-3 times with THF. The filtrate was concentrated to get the desired trans-4-amino-5-(o-tolyl)pyrrolidin-2-one as brown gum (4.5 g, 99%).

Synthesis of trans-4-amino-5-(2-fluoro-5-methoxyphenyl)pyrrolidin-2-one (Intermediate A11)

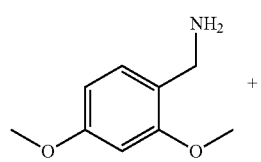
+
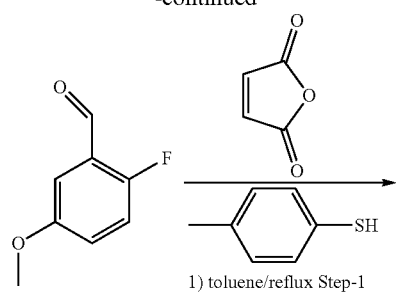

1) toluene/reflux Step-1

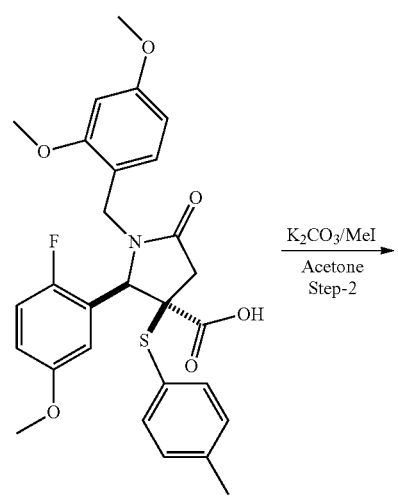

K$_2$CO$_3$/MeI
Acetone
Step-2

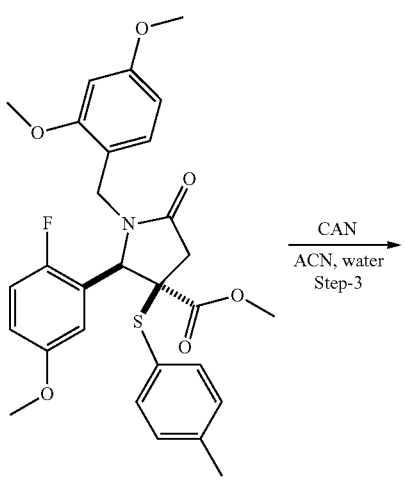

CAN
ACN, water
Step-3

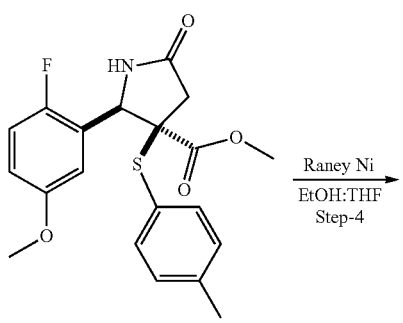

Raney Ni
EtOH:THF
Step-4

-continued

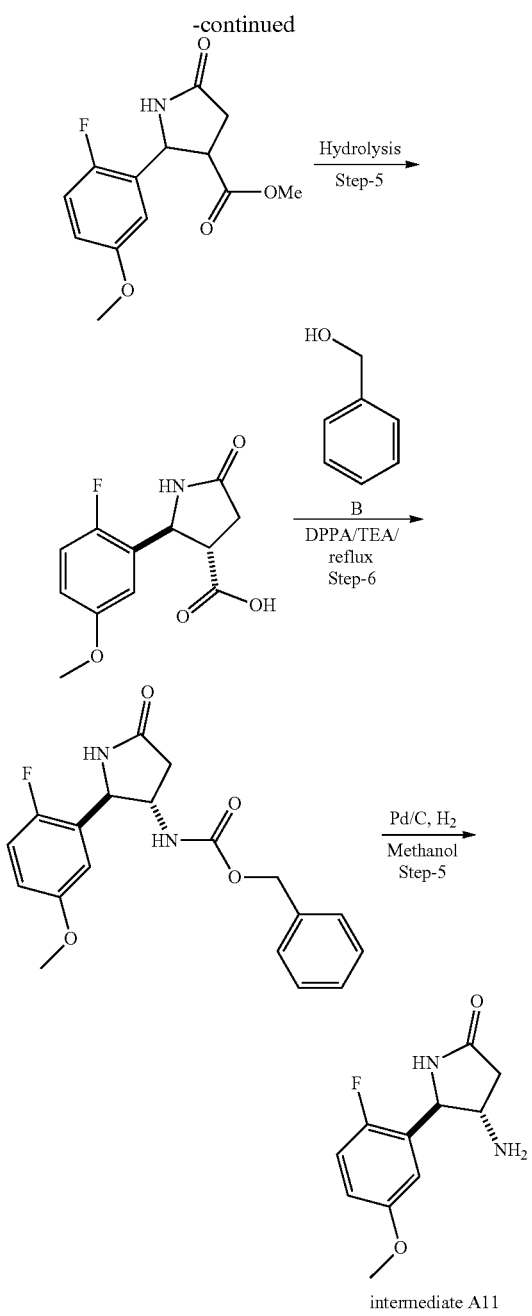

intermediate A11

Step 1: Maleic anhydride (14.6 g, 149.7 mmol, 1.0 eq), p-thiocresol (18.5 g, 149.7 mmol, 1.0 eq), 2,4-dimethoxy benzylamine (25.0 g, 149.7 mmol, 1.0 eq), and 2-fluoro-5-methoxybenzaldehyde (23.0 g, 149.7 mmol, 1.0 eq) were taken up in 300 mL of toluene. The reaction mixture was refluxed for 16 h with vigorous stirring. After completion of the reaction (monitored by TLC, TLC system 5% MeOH in DCM, $R_f$-0.1), the reaction mixture was cooled to RT and the solvent was then evaporated under reduced pressure to afford the crude product as a gummy liquid (75.0 g, 96%) which was used in the next step without further purification.

Step 2: To a stirred solution of crude 1-(2,4-dimethoxy-benzyl)-2-(2-fluoro-5-methoxyphenyl)-5-oxo-3-(p-tolyl-thio)pyrrolidine-3-carboxylic acid (75.0 g, 142.9 mmol, 1.0 eq) in acetone (1 L), potassium carbonate (78.9 g, 571.4 mmol, 4.0 eq) and methyl iodide (35.0 mL, 571.4 mmol, 4.0 eq) were added at 0° C., and the reaction mixture was stirred at RT for 16 h. After completion of the reaction (monitored by TLC, TLC system 30% EtOAc in hexane, $R_f$-0.3), the solvent was removed under reduced pressure and the residue was partitioned between EtOAc and water. The aqueous layer was extracted twice with EtOAc. The combined organic layers were washed with brine, dried over $Na_2SO_4$, filtered and concentrated. The crude product was purified by column chromatography (100-200 silica gel, 40% EtOAc in hexane) to afford the desired methyl 1-(2,4-dimethoxyben-zyl)-2-(2-fluoro-5-methoxyphenyl)-5-oxo-3-(p-tolylthio) pyrrolidine-3-carboxylate (45.0 g, 58%) as an off white solid.

Step 3: To a stirred solution of methyl 1-(2,4-dimethoxy-benzyl)-2-(2-fluoro-5-methoxyphenyl)-5-oxo-3-(p-tolyl-thio)pyrrolidine-3-carboxylate (45.0 g, 83.5 mmol, 1.0 eq) in acetonitrile, CAN (137.3 g, 250.4 mmol, 3.0 eq) in water was added dropwise through an addition funnel to the reaction mixture at 0° C. and the reaction mixture was stirred at RT for 16 h. After completion of the reaction (monitored by TLC, TLC system 50% EtOAc in hexane, Rf-0.3), the reaction mixture was diluted with water and extracted twice with EtOAc. The combined organic layers were washed with brine, dried over $Na_2SO_4$, filtered and concentrated. The crude product was purified by column chromatography (230-400 silica gel, 40-50% EtOAc: hexane) to give methyl 2-(2-fluoro-5-methoxyphenyl)-5-oxo-3-(p-tolylthio)pyrroli-dine-3-carboxylate (17.0 g, 52%) as an off white solid.

Step 4: To a stirred solution of methyl 2-(2-fluoro-5-methoxyphenyl)-5-oxo-3-(p-tolylthio)pyrrolidine-3-car-boxylate (17.0 g, 43.7 mmol, 1.0 eq) in EtOH: THF (300:300 mL, 1:1), Raney Nickel (17 g) was added and the reaction mixture was stirred under a hydrogen hydrogen atmosphere for 16 h at RT. After completion, (monitored by TLC, TLC system 70% EtOAc in hexane, Rf-0.4) the reaction mixture was filtered through a celite bed and the celite bed was washed 4-5 times with THF. The filtrate was concentrated to afford the desired methyl 2-(2-fluoro-5-methoxyphenyl)-5-oxopyrrolidine-3-carboxylate (9.0 g, 77%, syn:anti mixture) as a white solid.

Step 5: To a stirred solution of methyl 2-(2-fluoro-5-methoxyphenyl)-5-oxopyrrolidine-3-carboxylate (9.0 g, 33.7 mmol, 1 eq) in MeOH (180 mL) was added 2 N NaOH solution (36 mL) and the reaction mixture was stirred at 80° C. for 16 h. After completion of the reaction (monitored by TLC, TLC system 5% MeOH in DCM, Rf-0.1), the reaction mixture was concentrated and acidified with 2N HCl solution to obtain a solid which was filtered off and then washed with diethyl ether. Drying under vacuum afforded trans-2-(2-fluoro-5-methoxyphenyl)-5-oxopyrrolidine-3-carboxylic acid (7.9 g, 93%).

Step 6: To a stirred solution of trans-2-(2-fluoro-5-methoxyphenyl)-5-oxopyrrolidine-3-carboxylic acid (7.9 g, 31.2 mmol, 1.00 eq) in toluene (80 mL) were added TEA (4.6 mL, 32.8 mmol, 1.05 eq) and DPPA (10.3 g, 37.46 mmol, 1.20 eq) and the reaction mixture was stirred at 90° C. for 30 min. After 30 min, benzyl alcohol (6.7 g, 62.4 mmol, 2.00 eq) was added and the reaction mixture was heated to reflux for 16 h. After completion, (monitored by TLC, TLC system 5% MeOH in DCM, Rf-0.3), the reaction mixture was concentrated under reduced pressure. The residue was then diluted with EtOAc (100 mL), washed with water (2×100 mL), dried over $Na_2SO_4$ and concentrated under reduced pressure to get the crude product which was purified by column chromatography (230-400 mesh silica gel; 0-2% MeOH in DCM) to afford benzyl (trans-2-(2-fluoro-5-methoxyphenyl)-5-oxopyrrolidin-3-yl)carbamate (1.5 g, 13%).

Step 7: To a stirred solution of benzyl (trans-2-(2-fluoro-5-methoxyphenyl)-5-oxopyrrolidin-3-yl)carbamate (1.5 g, 4.2 mmol, 1.0 eq) in MeOH: THF (20 mL, 2:1), Pd/C (0.3 g, 0.548 mmol, 0.1 eq) was added, and the reaction mixture was stirred with a hydrogen balloon for 2 h at RT. After completion, (monitored by TLC, TLC system 5% MeOH in DCM, Rf-0.2), the reaction mixture was filtered through a celite bed and the celite bed was washed 2-3 times with THF. The filtrate was concentrated to get the desired trans-4-amino-5-(2-fluoro-5-methoxyphenyl)pyrrolidin-2-one (0.9 g, 96%) as a brown gum.

Synthesis of trans-N-(1-(1H-indazol-5-yl)-5-oxo-2-phenylpyrrolidin-3-yl)-2,2-difluoropropanamide (Intermediate B1)

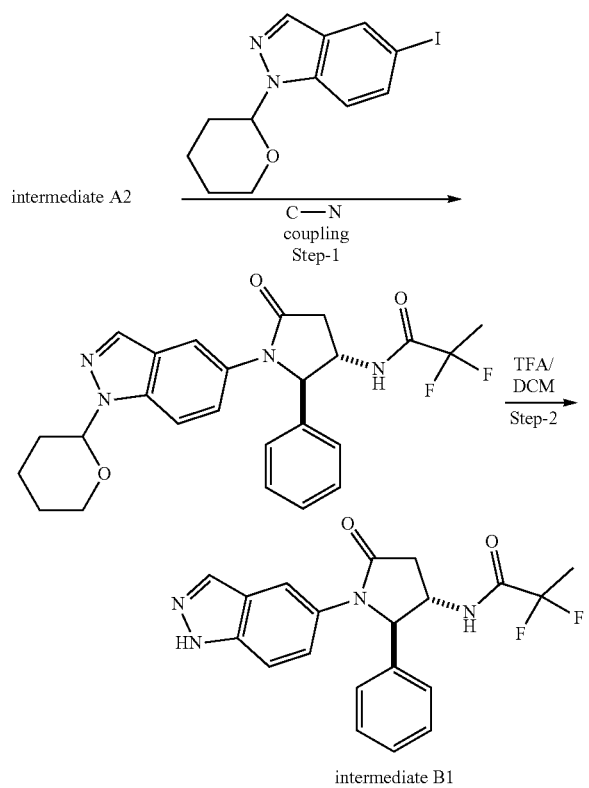

intermediate B1

Step 1: A stirred solution of intermediate A2 (1.2 g, 4.477 mmol, 1.0 eq), 5-iodo-1-(tetrahydro-2H-pyran-2-yl)-1H-indazole (1.8 g, 5.373 mmol, 1.2 eq) and K$_3$PO$_4$ (1.9 g, 8.955 mmol, 2.0 eq) in 1,4-dioxane (20 mL) was degassed with argon for 30 min. Then trans-N,N'-dimethylcyclohexane-1,2-diamine (0.3 g, 1.791 mmol, 0.4 eq) and CuI (0.2 g, 0.985 mmol, 0.2 eq) were added and the reaction mixture was stirred for 16 h at 90° C. in a sealed tube. After completion of the reaction (monitored by TLC, TLC system 5% MeOH in DCM, Rf-0.5), the reaction mixture was filtered through a celite bed and the celite bed was washed 2-3 times with 1,4-dioxane. The combined organic layers were concentrated to get the crude product which was purified by column chromatography (230-400 mesh silica gel; 0 to 2% MeOH in DCM) to afford the desired trans-2,2-difluoro-N-(5-oxo-2-phenyl-1-(1-(tetrahydro-2H-pyran-2-yl)-1H-indazol-5-yl)pyrrolidin-3-yl)propanamide (1.5 g, 72%).

Step 2: To a stirred solution of trans-2,2-difluoro-N-(5-oxo-2-phenyl-1-(1-(tetrahydro-2H-pyran-2-yl)-1H-indazol-5-yl)pyrrolidin-3-yl)propanamide (1.5 g, 3.20 mmol, 1.0 eq) in DCM (20 mL), TFA (15 mL) was added at 0° C. and the reaction was stirred for 16 h at RT. After completion of the reaction, (monitored by TLC, TLC system 5% MeOH in DCM, Rf-0.3), the reaction mixture was concentrated and basified with NaHCO$_3$ solution. The aqueous phase was extracted with DCM (3×100 mL). The combined organic layers were dried over Na$_2$SO$_4$, filtered and concentrated to afford trans-N-(1-(1H-indazol-5-yl)-5-oxo-2-phenylpyrrolidin-3-yl)-2,2-difluoropropanamide (1.1 g, 89%) as a solid.

Synthesis of 5-iodo-1-((2-methoxypyridin-4-yl)methyl)-1H-indazole (Intermediate C1)

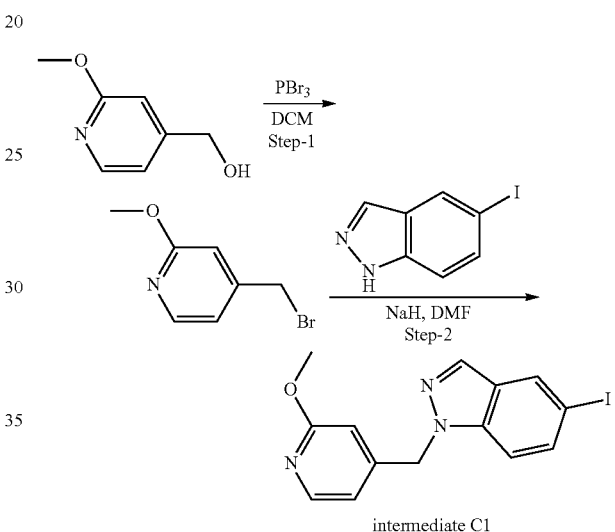

intermediate C1

Step 1: To a stirred solution of 2-methoxypyridin-4-yl)methanol (2.0 g, 14.372 mmol, 1.0 eq) in DCM (20 mL), PBr$_3$ (1.63 mL, 17.247 mmol, 1.2 eq) was added at 0° C. and the reaction was stirred at RT for 2 h. After completion of the reaction (monitored by TLC, TLC system 5% MeOH in DCM, Rf-0.3), the reaction was quenched with NaHCO$_3$ solution (150 mL) and the product was extracted with DCM (3×150 mL), dried over Na$_2$SO$_4$ and concentrated to get 4-(bromomethyl)-2-methoxypyridine (2.8 g, 96%).

Step 2: To a stirred solution of 5-iodo-1H-indazole (2.2 g, 9.018 mmol, 1.0 eq) in DMF (20 mL), NaH (50%) (0.432 g, 9.018 mmol, 1.0 eq) was added at 0° C., followed by the addition of 4-(bromomethyl)-2-methoxypyridine (2.7 g, 13.527 mmol, 1.5 eq) and the reaction mixture was then allowed to warm to RT over 16 hours. After completion of the reaction (monitored by TLC, TLC system 5% MeOH/DCM, Rf-0.4), the reaction mixture was quenched with ice cold water (100 mL) and extract with EtOAc (3×100 mL), washed with brine (50 mL) dried over Na$_2$SO$_4$ and concentrated to get the crude product which was purified by column chromatography (230-400 mesh silica gel; 0 to 4% MeOH-DCM) to afford 5-iodo-1-((2-methoxypyridin-4-yl)methyl)-1H-indazole (0.7 g, 21%) as a pure regioisomer.

$^1$H NMR (DMSO-d$_6$) δ: 8.21 (s, 1H), 8.11 (s, 1H), 8.05 (d, 1H), 7.62-7.67 (m, 1H), 7.55-7.57 (m, 1H), 6.67 (d, 1H), 6.45 (s, 1H), 5.67 (s, 2H), 3.78 (s, 3H).

Synthesis of 5-iodo-1-((1-methyl-1H-pyrazol-3-yl)methyl)-1H-indazole (Intermediate C2)

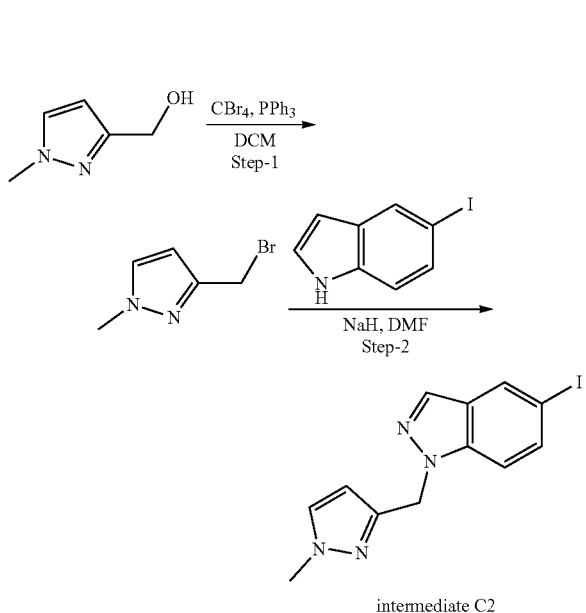

Step 1: To a stirred solution of (1-methyl-1H-pyrazol-3-yl)methanol (1.2 g, 10.708 mmol, 1.0 eq) in DCM (15 mL), CBr$_4$ (7.2 g, 21.417 mmol, 2.0 eq) and triphenylphosphine (5.7 g, 21.417 mmol, 2.0 eq) were added at RT and the reaction was then stirred for 16 h. After completion of the reaction (monitored by TLC, TLC system 5% MeOH in DCM, Rf-0.3), the reaction mixture was diluted with water (150 mL), extracted with DCM (3×150 mL), washed with brine (50 mL), dried over Na$_2$SO$_4$ and concentrated to get the crude product which was purified by column chromatography (230-400 mesh silica gel; 0 to 2% MeOH-DCM) to afford 3-(bromomethyl)-1-methyl-1H-pyrazole (1.25 g, 67%).

Step 2: To a stirred solution of 5-iodo-H-indazole (1.34 g, 5.517 mmol, 0.8 eq) in DMF (20 mL) NaH (50%) (0.40 g, 8.276 mmol, 1.2 eq) was added at 0° C., followed by the addition of 3-(bromomethyl)-1-methyl-1H-pyrazole (1.20 g, 6.897 mmol, 1.0 eq). The reaction mixture was stirred at RT for 16 h. After completion of the reaction (monitored by TLC, TLC system 5% MeOH/DCM, Rf-0.4), the reaction mixture was quenched with ice cold water (100 mL), extracted with EtOAc (3×100 mL), washed with brine (50 mL), dried over Na$_2$SO$_4$ and concentrated to get the crude product which was purified by column chromatography (230-400 mesh silica gel; 0 to 4% MeOH-DCM) to afford 5-iodo-1-((1-methyl-1H-pyrazol-3-yl)methyl)-1H-indazole (0.7 g, 30%).

Synthesis of 5-iodo-1-((6-methoxypyridin-3-yl)methyl)-1H-indazole (Intermediate C3)

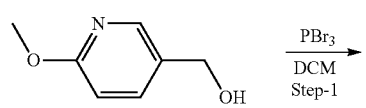

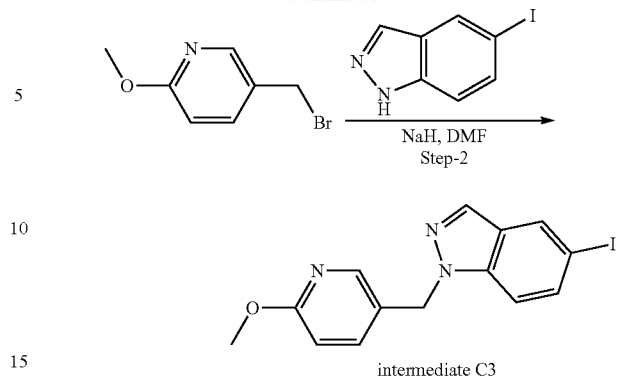

Step 1: To a stirred solution of (6-methoxypyridin-3-yl)methanol (0.60 g, 4.316 mmol, 1.0 eq) in DCM (20 mL), was added PBr$_3$ (0.50 mL, 5.179 mmol, 1.2 eq) was added at 0° C. and the reaction was then stirred at RT for 2 h. After completion of the reaction (monitored by TLC, TLC system 5% MeOH in DCM, Rf-0.3), the reaction was quenched with sat. NaHCO$_3$ solution (50 mL), extracted with DCM (3×50 mL), dried over Na$_2$SO$_4$ and concentrated to get 5-(bromomethyl)-2-methoxypyridine (0.55 g, 63%).

Step 2: To a stirred solution of 5-iodo-1H-indazole (0.49 g, 1.990 mmol, 0.8 eq) in DMF (20 mL), was added NaH (50%, 0.14 g, 2.985 mmol, 1.2 eq) at 0° C., followed by the addition of 5-(bromomethyl)-2-methoxypyridine (0.50 g, 2.488 mmol, 1.0 eq). The reaction mixture was stirred at RT for 16 h. After completion of the reaction (monitored by TLC, TLC system 5% MeOH/DCM, Rf-0.4), the reaction mixture was quenched with ice cold water (100 mL), extracted with EtOAc (3×100 mL), washed with brine (50 mL), dried over Na$_2$SO$_4$ and concentrated to get the crude product which was purified by column chromatography (230-400 mesh silica gel; 0 to 4% MeOH-DCM) to afford 5-iodo-1-((6-methoxypyridin-3-yl)methyl)-1H-indazole (0.40 g, 44%).

$^1$H NMR (DMSO-d$_6$) δ: 8.14 (s, 1H), 8.08 (m, 1H), 7.99 (s, 1H), 7.62 (m$_e$, 1H), 7.52 (m$_e$, 1H), 7.43 (m$_e$, 1H), 6.70 (d, 1H), 5.54 (s, 2H), 3.85 (s, 3H).

Synthesis of 5-((5-iodo-1H-indazol-1-yl)methyl)-1-methylpyridin-2(1H)-one (Intermediate C4)

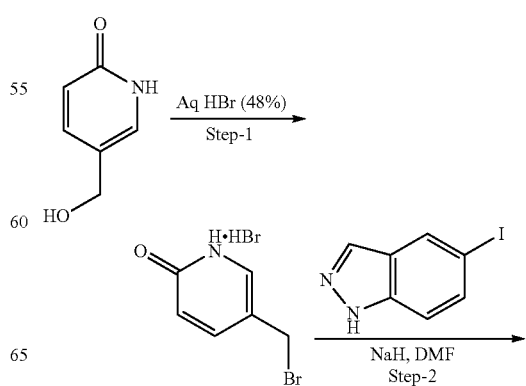

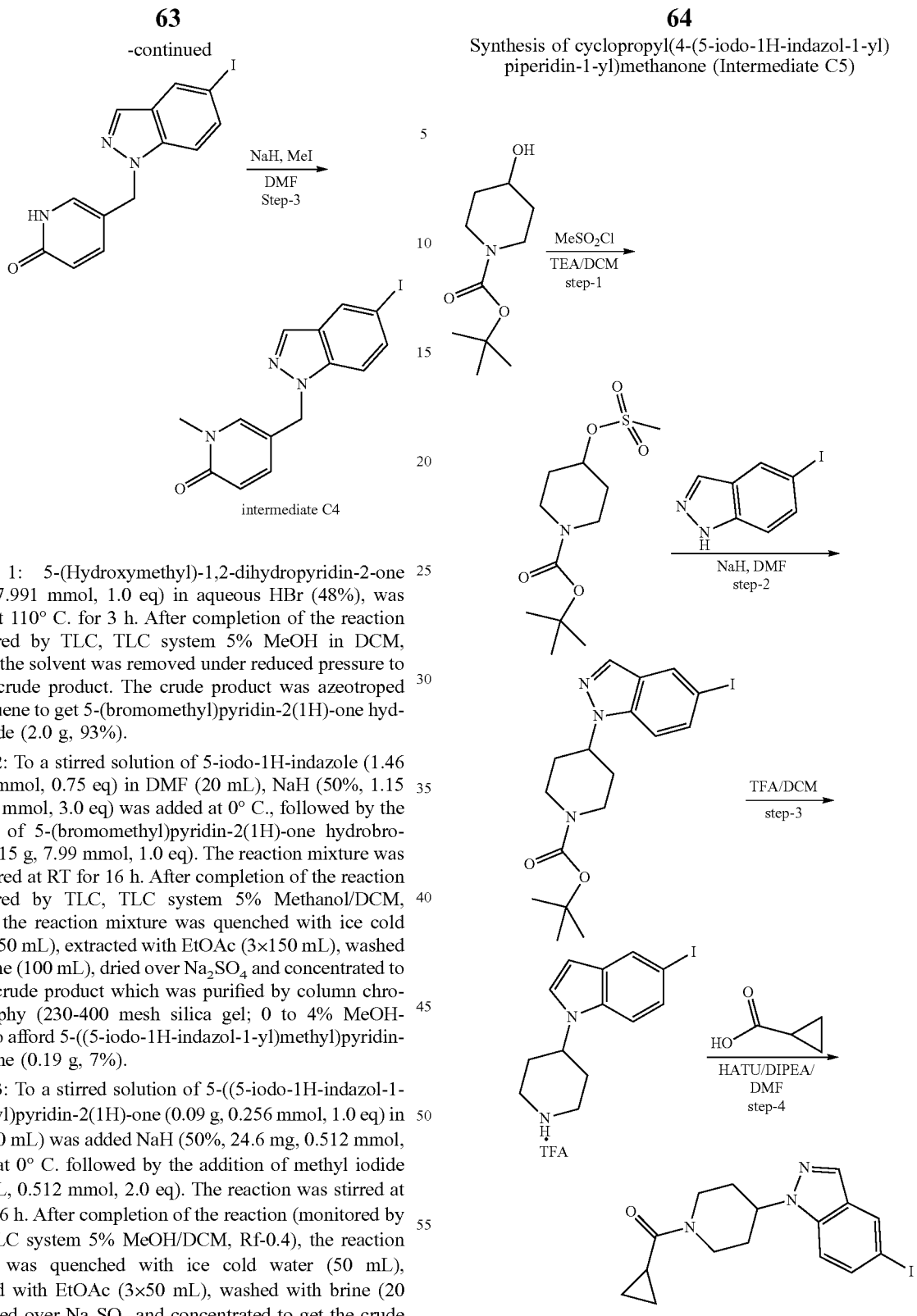

intermediate C4

Step 1: 5-(Hydroxymethyl)-1,2-dihydropyridin-2-one (1.0 g, 7.991 mmol, 1.0 eq) in aqueous HBr (48%), was stirred at 110° C. for 3 h. After completion of the reaction (monitored by TLC, TLC system 5% MeOH in DCM, Rf-0.1), the solvent was removed under reduced pressure to get the crude product. The crude product was azeotroped with toluene to get 5-(bromomethyl)pyridin-2(1H)-one hydrobromide (2.0 g, 93%).

Step 2: To a stirred solution of 5-iodo-1H-indazole (1.46 g, 5.99 mmol, 0.75 eq) in DMF (20 mL), NaH (50%, 1.15 g, 23.97 mmol, 3.0 eq) was added at 0° C., followed by the addition of 5-(bromomethyl)pyridin-2(1H)-one hydrobromide (2.15 g, 7.99 mmol, 1.0 eq). The reaction mixture was then stirred at RT for 16 h. After completion of the reaction (monitored by TLC, TLC system 5% Methanol/DCM, Rf-0.3), the reaction mixture was quenched with ice cold water (150 mL), extracted with EtOAc (3×150 mL), washed with brine (100 mL), dried over $Na_2SO_4$ and concentrated to get the crude product which was purified by column chromatography (230-400 mesh silica gel; 0 to 4% MeOH-DCM) to afford 5-((5-iodo-1H-indazol-1-yl)methyl)pyridin-2(1H)-one (0.19 g, 7%).

Step 3: To a stirred solution of 5-((5-iodo-1H-indazol-1-yl)methyl)pyridin-2(1H)-one (0.09 g, 0.256 mmol, 1.0 eq) in DMF (10 mL) was added NaH (50%, 24.6 mg, 0.512 mmol, 2.0 eq) at 0° C. followed by the addition of methyl iodide (0.04 mL, 0.512 mmol, 2.0 eq). The reaction was stirred at RT for 16 h. After completion of the reaction (monitored by TLC, TLC system 5% MeOH/DCM, Rf-0.4), the reaction mixture was quenched with ice cold water (50 mL), extracted with EtOAc (3×50 mL), washed with brine (20 mL), dried over $Na_2SO_4$ and concentrated to get the crude product which was purified by column chromatography (230-400 mesh silica gel; 0 to 3% MeOH-DCM) to afford 5-((5-iodo-1H-indazol-1-yl)methyl)-1-methylpyridin-2(1H)-one (0.09 g, 96%).

$^1$H NMR (DMSO-$d_6$) δ: 8.18 (s, 1H), 8.04 (s, 1H), 7.85 (s, 1H), 7.65 ($m_c$, 2H), 7.29 (dd, 1H), 6.30 (d, 1H), 5.35 (s, 2H), 3.34 (s, 3H).

Synthesis of cyclopropyl(4-(5-iodo-1H-indazol-1-yl)piperidin-1-yl)methanone (Intermediate C5)

intermediate C5

Step 1: To a stirred solution of tert-butyl 4-hydroxypiperidine-1-carboxylate (1.19 g, 4.88 mmol, 1.0 eq) in DCM (20 mL) at 0° C. was added TEA (1.04 ml, 7.45 mmol, 1.5 eq) and the reaction was stirred for 5 minutes. Methane sulfonyl chloride (0.46 ml, 5.96 mmol, 1.2 eq) was added dropwise at 0° C. Then the reaction mixture was stirred at 0°

C. for 1 h. After completion, the reaction mixture was diluted with DCM and washed with water and sat. NH₄Cl solution. The combined organic layer was concentrated to get the crude product which was purified by column chromatography (100-200 mesh silica gel; 50% EtOAc/Hexane; R_f-value-0.5) to afford tert-butyl 4-((methylsulfonyl)oxy) piperidine-1-carboxylate (1.35 g, 98%).

Step 2: To a stirred solution of 5-iodo-1H-indazole (1.19 g, 4.88 mmol, 1.0 eq) in DMF (20 mL) at 0° C. was added NaH (0.26 g, 5.37 mmol, 1.1 eq.) and the reaction mixture was stirred for 15 min. Then tert-butyl 4-((methylsulfonyl) oxy)piperidine-1-carboxylate (1.5 g, 5.37 mmol, 1.1 eq) dissolved in DMF (10 mL) was added dropwise at 0° C. Then the reaction mixture was heated to 100° C. for 16 h. After completion, the reaction mixture was diluted with EtOAc and washed with ice water. The combined organic layers were concentrated to get the crude product which was purified by column chromatography (100-200 mesh silica gel; 50% EtOAc/Hexane; R_f-value-0.5, isomer separation) to afford tert-butyl 4-(5-iodo-1H-indazol-1-yl)piperidine-1-carboxylate (0.82 g, 41%) as a single regioisomer.

Step 3: To a solution of tert-butyl 4-(5-iodo-1H-indazol-1-yl)piperidine-1-carboxylate (0.82 g, 1.92 mmol, 1.0 eq) in DCM (20 mL) at 0° C. TFA (5 mL) was added dropwise, and the reaction mixture was stirred for 1 h at RT. After completion, the reaction mixture was concentrated to get the crude 5-iodo-1-(piperidin-4-yl)-1H-indazole as the TFA salt (0.1 g, crude).

Step 4: To a stirred solution of 5-iodo-1-(piperidin-4-yl)-1H-indazole (TFA salt, 0.6 g, 1.83 mmol, 1.0 eq) in DMF (20 mL), HATU (1.0 g, 2.75 mmol, 1.5 eq), DIPEA (1.6 mL, 9.17 mmol, 5.0 eq) and cyclopropanecarboxylic acid (0.23 g, 2.75 mmol, 1.5 eq) were added, and the reaction mixture was stirred for 16 h at RT. After completion, the reaction mixture was diluted with EtOAc, washed with ice cold water, sat. NaHCO₃ and sat. NH₄Cl solution. The combined organic layers were concentrated to get the crude product which was purified by column chromatography (100-200 mesh silica gel; 2% MeOH-DCM; R_f-value-0.5) to afford cyclopropyl(4-(5-iodo-1H-indazol-1-yl)piperidin-1-yl) methanone (0.3 g).

Synthesis of 4-((5-iodo-1H-indazol-1-yl)methyl)-1-methylpyridin-2(1H)-one (Intermediate C6)

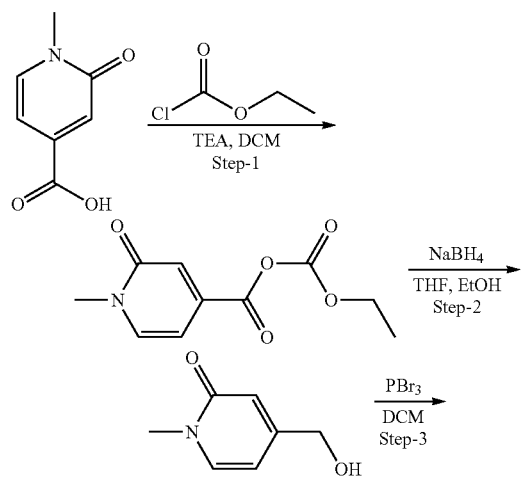

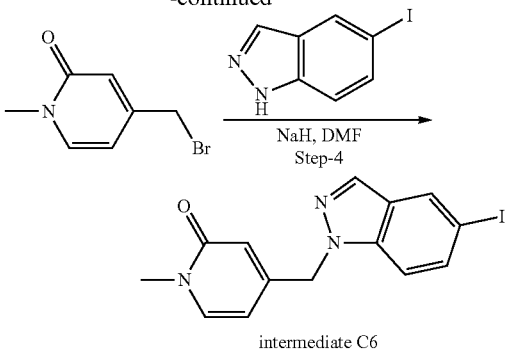

intermediate C6

Step 1: To a stirred solution of 1-methyl-2-oxo-1,2-dihydropyridine-4-carboxylic acid (3.0 g, 19.60 mmol, 1.0 eq) in DCM (30 mL), TEA (4.1 mL, 29.40 mmol, 1.5 eq) and ethyl chloroformate (2.24 mL, 23.52 mmol, 1.2 eq) were added and the reaction mixture was stirred at RT for 2 h. After completion of the reaction (monitored by TLC, TLC system 5% MeOH in DCM, Rf-0.7), the reaction mixture was concentrated to get the crude (ethyl carbonic) 1-methyl-2-oxo-1,2-dihydropyridine-4-carboxylic anhydride which was used in the next step without further purification (3.0 g, 68%).

Step 2: To a stirred solution of crude (ethyl carbonic) 1-methyl-2-oxo-1,2-dihydropyridine-4-carboxylic anhydride (3.0 g, 13.329 mmol, 1.0 eq) in THF:EtOH (80 mL, 3:1), NaBH₄ (2.5 g, 66.648 mmol, 5.0 eq) was added and the reaction mixture was stirred at RT for 2 h. After completion of the reaction (monitored by TLC, TLC system 50% EtOAc in Hexane, Rf-0.1), the reaction mixture was quenched with ice cold water (75 mL), extracted with 5% MeOH in DCM (3×150 mL), dried over Na₂SO₄ and concentrated under reduced pressure to get the crude 4-(hydroxymethyl)-1-methylpyridin-2(1H)-one which was used in next step without further purification (1.7 g, 92%).

Step 3: To a stirred solution of crude 4-(hydroxymethyl)-1-methylpyridin-2(1H)-one (1.2 g, 8.63 mmol, 1.0 eq) in DCM (15 mL), PBr₃ (1.0 mL, 10.36 mmol, 1.2 eq) was added at 0° C. and the reaction mixture was then stirred at RT for 2 h. After completion of the reaction (monitored by TLC, TLC system 50% EtOAc in Hexane, Rf-0.4), the reaction mixture was quenched with NaHCO₃ solution (50 mL), extracted with DCM (3×50 mL), dried over Na₂SO₄ and concentrated under reduced pressure to get 4-(bromomethyl)-1-methylpyridin-2(1H)-one (1.0 g, 57%).

Step 4: To a stirred solution of 5-iodo-1H-indazole (0.970 g, 3.980 mmol, 0.8 eq) in DMF (20 mL) was added NaH (50%, 0.238 g, 4.975 mmol, 1.0 eq) at 0° C., followed by the addition of 4-(bromomethyl)-1-methylpyridin-2(1H)-one (1.0 g, 4.975 mmol, 1.0 eq). The reaction mixture was then stirred at RT for 16 h. After completion of the reaction (monitored by TLC, TLC system 5% MeOH/DCM, R_f-0.4), the reaction mixture was quenched with ice cold water (50 mL), extracted with EtOAc (3×50 mL), washed with brine (50 mL), dried over Na₂SO₄ and concentrated to get the crude product which was purified by column chromatography (230-400 mesh silica gel; 0 to 3% MeOH-DCM) to afford 4-((5-iodo-1H-indazol-1-yl)methyl)-1-methylpyridin-2(1H)-one (0.360 g, 20%) as a single regioisomer.

¹H NMR (DMSO-d₆) δ: 8.22 (s, 1H), 8.10 (s, 1H), 7.54-7.66 (m, 3H), 5.94 (s, 1H), 5.90 (d, 1H), 5.51 (s, 2H), 3.33 (s, 3H).

Synthesis of 5-(5-((2R,3S)-3-amino-5-oxo-2-phenylpyrrolidin-1-yl)-1H-indazol-1-yl)-1-methylpyridin-2(1H)-one (Intermediate D1-ent2)

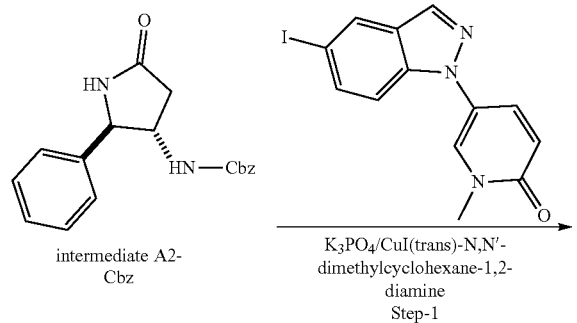

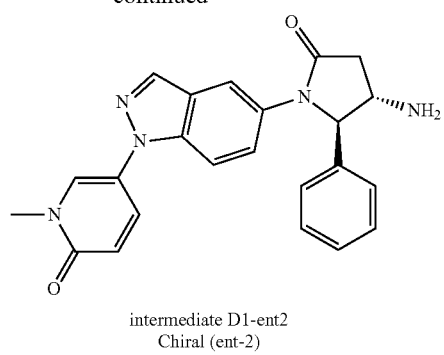

intermediate D1-ent2
Chiral (ent-2)

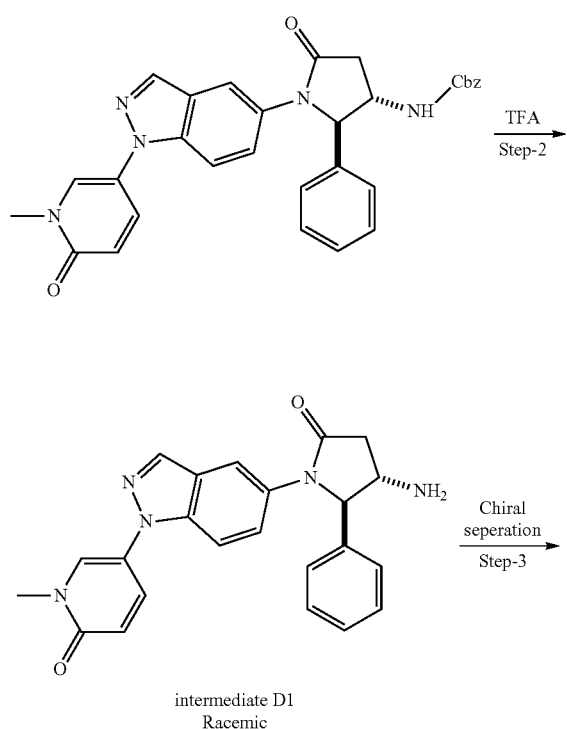

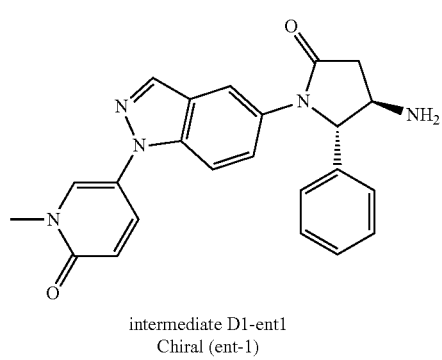

intermediate D1-ent1
Chiral (ent-1)

Step 1: To a stirred solution of benzyl N-[(trans)-2-phenyl-5-oxo-pyrrolidin-3-yl]carbamate (Intermediate A2-Cbz, 1.0 g, 3.22 mmol, 1.0 eq) and 5-(5-iodo-1H-indazol-1-yl)-1-methylpyridin-2(1H)-one (1.1 g, 3.22 mmol, 1.0 eq) in 1,4-dioxane (80 ml) was added potassium phosphate (1.4 g, 6.44 mmol, 2.0 eq), followed by trans-N,N'-dimethylcyclohexane-1,2-diamine (1.02 ml 0.65 mmol, 0.2 eq) and the reaction mixture was degassed under an argon atmosphere for 30 minutes, CuI (61.3 mg, 0.32 mmol, 0.1 eq) was then added and the reaction was heated in a sealed tube at 90° C. for 16 h (monitored by LCMS). The reaction mixture was filtered over a bed of celite and the celite bed was washed with EtOAc (500 ml) and the combined organic layers were concentrated under reduced pressure. The crude residue was purified by column chromatography (100-200 silica gel, 3-5% MeOH-DCM as eluent) to afford benzyl N-[(trans)-1-(1-(1-methyl-6-oxo-1,6-dihydropyridin-3-yl)-1H-indazol-5-yl)-2-phenyl-5-oxo-pyrrolidin-3-yl]-carbamate (750 mg, 44%).

Step 2: A stirred suspension of benzyl N-[(trans)-1-(1-(1-methyl-6-oxo-1,6-dihydropyridin-3-yl)-1H-indazol-5-yl)-2-phenyl-5-oxo-pyrrolidin-3-yl]carbamate (22.0 g, 41.2 mmol) in TFA (80 ml) was heated at 80° C. for 2 h. After completion of the reaction (monitored by LCMS), the reaction mixture was cooled to RT and TFA was removed under reduced pressure as an azeotrope with toluene. The residue was basified (pH~8) with a sat. solution of NaHCO$_3$ and extracted with 10% MeOH/DCM (5×150 ml). The combined organic layers were dried over Na$_2$SO$_4$, filtered and concentrated under reduced pressure. The crude residue was purified by column chromatography (100-200 Silica gel, 5-10% MeOH/DCM as eluent) to afford (trans)-4-amino-5-(phenyl)-1-(1-(1-methyl-6-oxo-1,6-dihydropyridin-3-yl)-1H-indazol-5-yl)pyrrolidin-2-one (11.0 g, 67%) as a grey solid.

Step 3: Chiral separation

The racemic compound was separated by chiral prep HPLC (Column ID: CHIRALPAK IB (4.6×250 nm), 5 μm; Mobile Phase: MeOH/DEA (100/0.1); Flow rate: 1 ml/min; Temp: 25° C.) to afford intermediate D1-ent1 (Peak 1; 4.915 g; 100% ee) and intermediate D1-ent2 (Peak 2; 2.763 g; 99.60% ee).

EXAMPLE 1

N-((2R,3S)-2-(3-chlorophenyl)-1-(1-(1-methyl-6-oxo-1,6-dihydropyridin-3-yl)-1H-indazol-5-yl)-5-oxopyrrolidin-3-yl)-2,2-difluoropropanamide

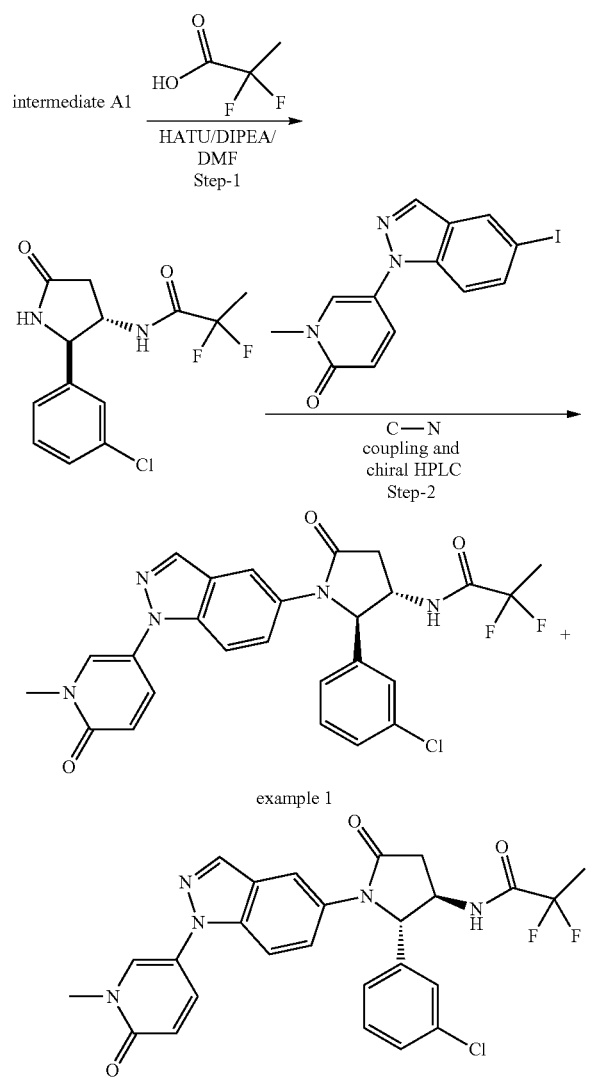

example 1

Step 1: To a stirred solution of intermediate A1 (0.25 g, 1.19 mmol, 1.0 eq) in DMF (10 mL), HATU (0.68 g, 1.78 mmol, 1.5 eq), DIPEA (1.0 ml, 5.95 mmol, 5.0 eq) and 2,2-difluoropropanoic acid (0.17 g, 1.54 mmol, 1.3 eq) were added, and the reaction mixture was stirred for 16 h at RT. After completion, the reaction mixture was diluted with EtOAc and was washed with ice cold water, sat. NaHCO$_3$ and sat. NH$_4$Cl solution. The combined organic layers were concentrated to get the crude product, which was purified by column chromatography (100-200 mesh silica gel; 2% MeOH-DCM; R$_f$-value-0.5) to afford trans-N-(2-(3-chlorophenyl)-5-oxopyrrolidin-3-yl)-2,2-difluoropropanamide (0.19 g, 53%).

Step 2: A stirred solution of trans-N-(2-(3-chlorophenyl)-5-oxopyrrolidin-3-yl)-2,2-difluoropropanamide (0.30 g, 0.99 mmol, 1.0 eq), 5-(5-iodo-1H-indazol-1-yl)-1-methylpyridin-2(1H)-one (0.41 g, 1.19 mmol, 1.2 eq) and K$_3$PO$_4$ (0.42 g, 1.98 mmol, 2.0 eq) in 1,4-dioxane (20 mL) was degassed with argon for 15 min. Then, trans-N,N'-dimethylcyclohexane-1,2-diamine (0.056 g, 0.40 mmol, 0.4 eq) and CuI (0.038 g, 0.20 mmol, 0.2 eq) were added and the reaction mixture was stirred for 16 h at 90° C. After completion, the reaction mixture was filtered through a celite bed and the celite bed was washed 2-3 times with EtOAc. The combined organic layers were concentrated to get the crude product which was purified by column chromatography (100-200 mesh silica gel; 5% MeOH-DCM; R$_f$-value-0.5) to afford the racemic product and further separation of enantiomers was done by chiral preparative HPLC to afford N-((2R,3S)-2-(3-chlorophenyl)-1-(1-(1-methyl-6-oxo-1,6-dihydropyridin-3-yl)-1H-indazol-5-yl)-5-oxopyrrolidin-3-yl)-2,2-difluoropropanamide (0.07 g, RT=15.9 min, Column Name: CHIRALPAK IA (250×4.6 mm) 5 μm, Mobile phase: HEXANE/EtOH/EA/DEA: 70/15/15/0.1, Flow Rate: 1.0 ml/min) [and N-((2S,3R)-2-(3-chlorophenyl)-1-(1-(1-methyl-6-oxo-1,6-dihydropyridin-3-yl)-1H-indazol-5-yl)-5-oxopyrrolidin-3-yl)-2,2-difluoropropanamide (0.06 g; RT=10.6 min, Column Name: CHIRALPAK IA (250×4.6 mm) 5 μm, Mobile phase: HEXANE/EtOH/EA/DEA: 70/15/15/0.1, Flow Rate: 1.0 ml/min)].

$^1$H NMR (DMSO-d$_6$) δ: 9.46 (d, 1H), 8.26 (s, 1H), 8.19 (d, 1H), 7.86 (s, 1H), 7.71 (dd, 1H), 7.62-7.58 (m, 2H), 7.45 (s, 1H), 7.34-7.28 (m, 3H), 6.53 (d, 1H), 5.34 (d, 1H), 4.30 (bs, 1H), 3.49 (s, 3H), 3.14-3.08 (m, 1H) 2.67-2.62 (m, 1H), 1.78 (t, 3H).

EXAMPLE 2 trans-2,2-difluoro-N-(5-oxo-2-(2,4-difluorophenyl)-1-(1-(1-methyl-6-oxo-1,6-dihydropyridin-3-yl)-1H-indazol-5-yl)pyrrolidin-3-yl)propanamide

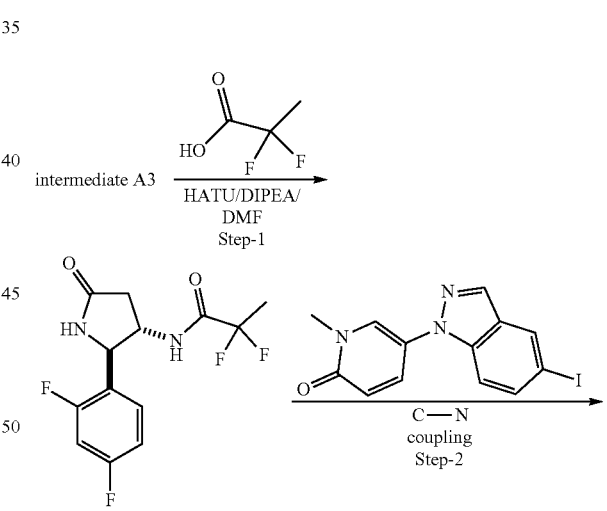

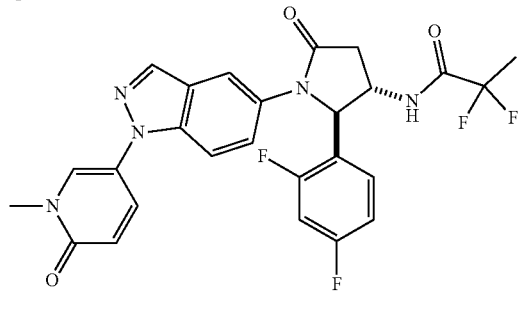

example 2

Step 1: A solution of intermediate A3 (0.85 g, 4.09 mmol, 1.0 eq) in DMF (12 mL) was treated with 2,2-difluoropropanoic acid (0.57 g, 5.21 mmol, 1.3 eq) in presence of HATU (3.04 g, 8.01 mmol, 2.0 eq) and DIPEA (3.5 ml, 20.04 mmol, 2.0 eq) and the mixture was stirred at RT for 16 h. The reaction mixture was then partitioned between EtOAc and water, the organic extracts were washed with brine, dried and concentrated to afford the crude product which was purified by flash column chromatography (230-400 mesh silica gel; 5% MeOH/EtOAc; $R_f$-value-0.4) to afford trans-N-(-2-(2,4-difluorophenyl)-5-oxopyrrolidin-3-yl)-2,2-difluoropropanamide (0.7 g, 58%) as an off white solid.

Step 2: To a stirred solution of trans-N-(-2-(2,4-difluorophenyl)-5-oxopyrrolidin-3-yl)-2,2-difluoropropanamide (0.30 g, 0.98 mmol, 1.0 eq) and 5-(5-iodo-1H-indazol-1-yl)-1-methylpyridin-2(1H)-one (0.35 g, 0.98 mmol, 1.0 eq) in 1,4-dioxane (5 mL) were added $K_3PO_4$ (0.41 g, 1.97 mmol, 2.0 eq), CuI (0.038 g, 0.19 mmol, 0.2 eq) and trans-N,N'-dimethylcyclohexane-1,2-diamine (0.056 g, 0.39 mmol, 0.4 eq) at RT under a nitrogen atmosphere and the mixture was degassed with a stream of nitrogen for 5 min. The resulting mixture was heated to 90° C. for 16 h. The reaction mixture was allowed to cool to RT, was then filtered and concentrated to afford the crude product which was purified by flash column chromatography (230-400 mesh silica gel; 5% MeOH/EtOAc; $R_f$-value-0.4) to afford trans-N-(-2-(2,4-difluorophenyl)-1-(1-(1-methyl-6-oxo-1,6-dihydropyridin-3-yl)-1H-indazol-5-yl)-5-oxopyrrolidin-3-yl)-2,2-difluoropropanamide (0.16 g, 31%) as an off white solid.

$^1$H NMR (DMSO-d$_6$) δ: 9.4 (d, 1H), 8.27 (s, 1H), 8.20 (d, 1H), 7.77 (s, 1H), 7.71 (dd, 1H), 7.61 (d, 1H), 7.52-7.43 (m, 2H), 7.20 (t, 1H), 7.00 (t, 1H), 6.53 (d, 1H), 5.50 (d, 1H), 4.49 (t, 1H), 3.49 (s, 3H), 3.14-3.07 (m, 1H), 2.7 (dd, 1H), 1.75 (t, 3H).

EXAMPLE 3 trans-2,2-difluoro-N-(5-oxo-2-(2,3-dihydrobenzo[b][1,4]dioxin-6-yl)-1-(1-(1-methyl-6-oxo-1,6-dihydropyridin-3-yl)-1H-indazol-5-yl)pyrrolidin-3-yl)propanamide

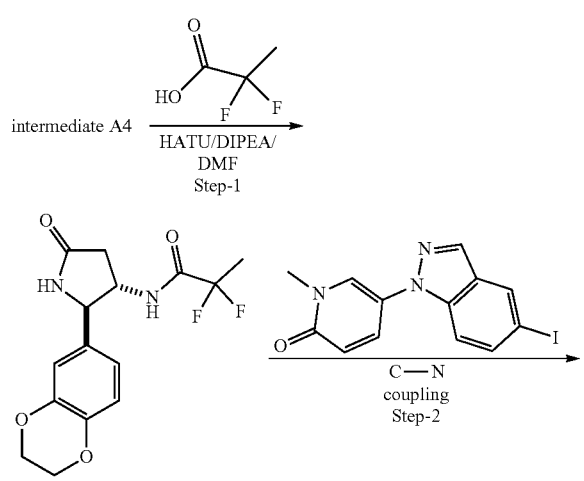

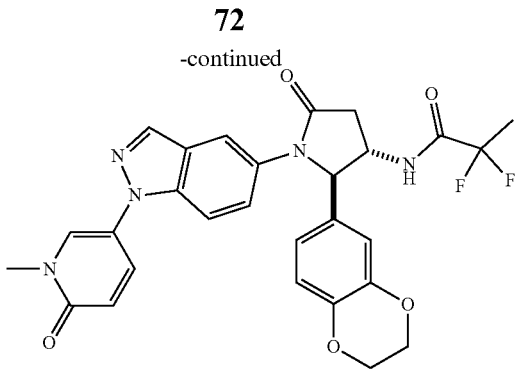

example 3

Step 1: To a stirred solution of intermediate A4 (0.20 g, 0.87 mmol, 1.0 eq) in DMF (10 mL), HATU (0.49 g, 1.30 mmol, 1.5 eq), DIPEA (0.75 mL, 4.30 mmol, 5.0 eq) and 2,2-difluoro-propionic acid (0.12 g, 1.12 mmol, 1.3 eq) were added, and the reaction was stirred for 16 h at RT. After completion, the reaction mixture was diluted with EtOAc, washed with ice cold water, sat. NaHCO$_3$ and sat. NH$_4$Cl solution. The combined organic layers were concentrated to get the crude product which was purified by column chromatography (100-200 mesh silica gel; 2% MeOH-DCM; $R_f$-value-0.5) to afford trans-N-(2-(2,3-dihydrobenzo[b][1,4]dioxin-6-yl)-5-oxopyrrolidin-3-yl)-2,2-difluoropropanamide (0.20 g, 71%).

Step 2: A stirred solution of trans-N-(2-(2,3-dihydrobenzo[b][1,4]dioxin-6-yl)-5-oxopyrrolidin-3-yl)-2,2-difluoropropanamide (0.20 g, 0.613 mmol, 1.0 eq), 5-(5-iodo-1H-indazol-1-yl)-1-methylpyridin-2(1H)-one (0.26 g, 0.736 mmol, 1.2 eq) and K$_3$PO$_4$ (0.26 g, 1.22 mmol, 2.0 eq) in 1,4-dioxane (20 mL) was degassed with argon for 15 min. Then, trans-N,N'-dimethylcyclohexane-1,2-diamine (0.035 g, 0.245 mmol, 0.4 eq) and CuI (0.025 g, 0.122 mmol, 0.2 eq) were added and the reaction was stirred for 16 h at 90° C. After completion, the reaction mixture was filtered through a celite bed and the celite bed was washed 2-3 times with EtOAc. The combined organic layers were concentrated to get the crude product which was purified by column chromatography (100-200 mesh silica gel; 5% MeOH-DCM; $R_f$-value-0.3) to afford trans-N-(2-(2,3-dihydrobenzo[b][1,4]dioxin-6-yl)-1-(1-(1-methyl-6-oxo-1,6-dihydropyridin-3-yl)-1H-indazol-5-yl)-5-oxopyrrolidin-3-yl)-2,2-difluoropropanamide (0.12 g, 36%).

$^1$H NMR (DMSO-d$_6$) δ: 9.42 (d, 1H), 8.26 (s, 1H), 8.19 (d, 1H), 7.85 (s, 1H), 7.72 (dd, 1H), 7.62-7.56 (m, 2H), 6.82 (s, 1H), 6.77 (s, 2H), 6.54 (d, 1H), 5.20 (d, 1H), 4.24-4.20 (m, 1H), 4.16 (s, 4H), 3.50 (s, 3H), 3.10-3.04 (m, 1H) 2.60-2.56 (m, 1H), 1.78 (t, 3H).

EXAMPLE 4

2,2-difluoro-N-((2R,3S)-1-(1-(1-methyl-6-oxo-1,6-dihydropyridin-3-yl)-1H-indazol-5-yl)-5-oxo-2-phenylpyrrolidin-3-yl)propanamide

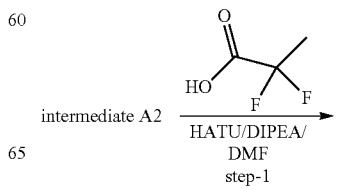

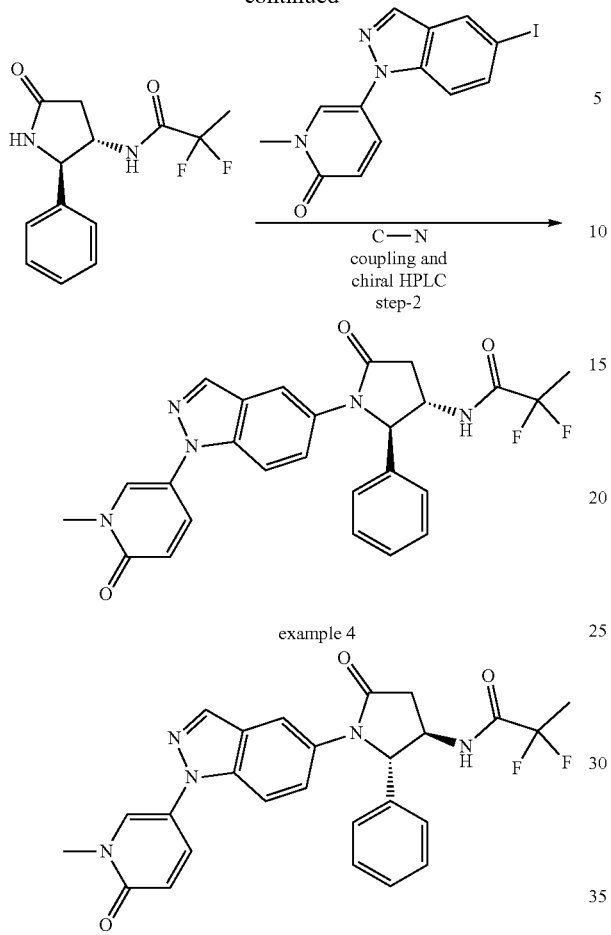

example 4

Step 1: To a stirred solution of intermediate A2 (1.0 g, 5.68 mmol, 1.0 eq) in DMF (20 mL), HATU (3.2 g, 8.52 mmol, 1.5 eq), DIPEA (4.9 mL, 28.40 mmol, 5.0 eq) and 2,2-difluoro-propionic acid (0.8 g, 7.38 mmol, 1.3 eq) were added. The reaction mixture was stirred for 16 h at RT. After completion, the reaction mixture was diluted with EtOAc and was washed with ice cold water, sat. NaHCO$_3$ and sat. NH$_4$Cl solution. The combined organic layers were concentrated to get the crude product which was purified by column chromatography (100-200 mesh silica gel; 2% MeOH-DCM; R$_f$-value-0.5) to afford trans-2,2-difluoro-N-(5-oxo-2-phenylpyrrolidin-3-yl)propanamide (1.4 g, 93%).

Step 2: A stirred solution of trans-2,2-difluoro-N-(5-oxo-2-phenylpyrrolidin-3-yl)propanamide (0.3 g, 1.11 mmol, 1.0 eq), 5-(5-iodo-1H-indazol-1-yl)-1-methylpyridin-2(1H)-one (0.47 g, 1.34 mmol, 1.2 eq) and K$_3$PO$_4$ (0.47 g, 2.23 mmol, 2.0 eq) in 1,4-dioxane (20 mL) was degassed with argon for 15 min. Then, trans-N,N'-dimethylcyclohexane-1,2-diamine (0.06 g, 0.45 mmol, 0.4 eq) and CuI (0.04 g, 0.22 mmol, 0.2 eq) were added and the reaction was stirred for 16 h at 90° C. After completion, the reaction mixture was filtered through a celite bed and the celite bed was washed 2-3 times with EtOAc. The combined organic layers were concentrated to get the crude product which was purified by column chromatography (100-200 mesh silica gel; 5% MeOH-DCM; R$_f$-value-0.5) to afford the racemic product and further enantiomer separation was done by chiral preparative HPLC to afford 2,2-difluoro-N-((2R,3S)-1-(1-(1-methyl-6-oxo-1,6-dihydropyridin-3-yl)-1H-indazol-5-yl)-5-oxo-2-phenylpyrrolidin-3-yl)propanamide (0.10 g; RT=8.06 min; Column Name: Chiralpak IA (250×4.6 mm) 5 μm, Mobile Phase: Hexane/EA/EtOH/DEA: 50/25/25/0.1, Flow Rate: 1.0 ml/min) [and 2,2-difluoro-N-((2S,3R)-1-(1-(1-methyl-6-oxo-1,6-dihydropyridin-3-yl)-1H-indazol-5-yl)-5-oxo-2-phenylpyrrolidin-3-yl)propanamide (0.14 g; RT=5.88 min; Column Name: Chiralpak IA (250×4.6 mm) 5 μm, Mobile Phase: Hexane/EA/EtOH/DEA: 50/25/25/0.1, Flow Rate: 1.0 ml/min)].

$^1$H NMR (DMSO-d$_6$) δ: 9.47 (d, 1H), 8.25 (s, 1H), 8.18 (d, 1H), 7.85 (s, 1H), 7.70 (dd, 1H), 7.58 (s, 2H), 7.35-7.29 (m, 4H), 7.24-7.22 (m, 1H), 6.53 (d, 1H), 5.30 (d, 1H), 4.24 (bs, 1H), 3.49 (s, 3H), 3.08-3.06 (m, 1H) 2.64-2.63 (m, 1H), 1.78 (t, 3H).

EXAMPLE 5

2,2-difluoro-N-((2R,3S)-2-(3-fluorophenyl)-1-(1-(1-methyl-6-oxo-1,6-dihydropyridin-3-yl)-1H-indazol-5-yl)-5-oxopyrrolidin-3-yl)propanamide

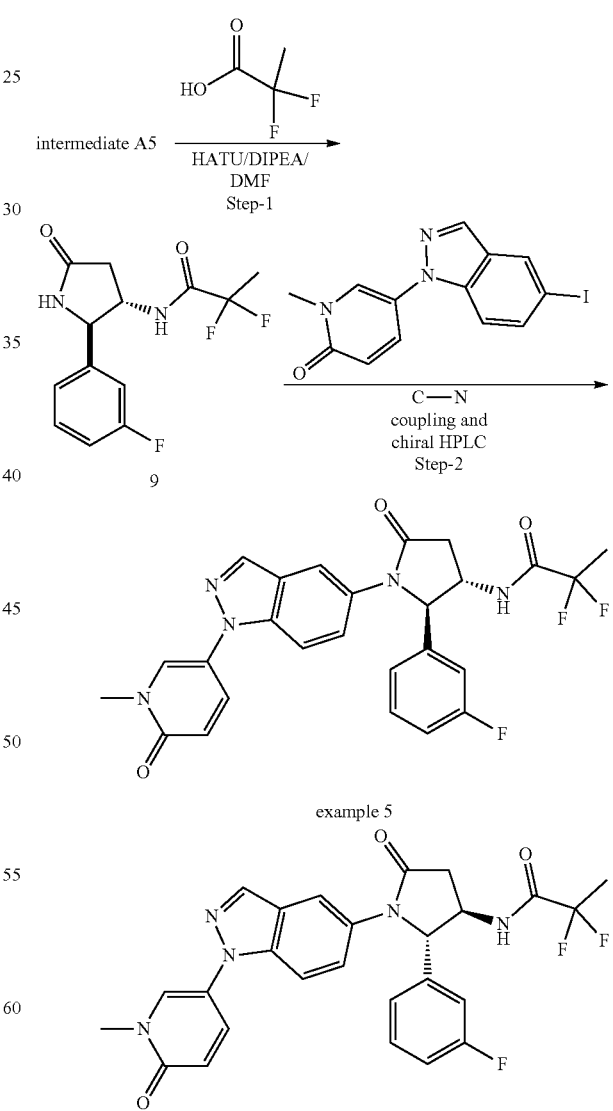

example 5

Step 1: To a stirred solution of 2,2-difluoro-propionic acid (0.68 g, 6.185 mmol, 1.2 eq) in DMF (10 mL), HATU (3.9 g, 10.309 mmol, 2.0 eq), DIPEA (4.5 mL, 25.773 mmol, 5.0 eq) and intermediate A5 (1.00 g, 5.1545 mmol, 1.0 eq) were added at 0° C. and the reaction was then stirred at RT for 16 h. After completion of the reaction (monitored by TLC), the reaction mixture was diluted with EtOAc (25 mL), washed with ice cold water (3×25 mL), dried over Na₂SO₄ and concentrated to get the crude product, which was purified by column chromatography (230-400 mesh silica gel; 0 to 2% MeOH-DCM) to afford trans-2,2-difluoro-N-(2-(3-fluorophenyl)-5-oxopyrrolidin-3-yl)propanamide (0.56 g, 38%).

Step 2: A stirred solution of trans-2,2-difluoro-N-(2-(3-fluorophenyl)-5-oxopyrrolidin-3-yl)propanamide (0.55 g, 1.923 mmol, 1 eq), 5-(5-iodo-1H-indazol-1-yl)-1-methyl-pyridin-2(1H)-one (0.81 g, 2.307 mmol, 1.2 eq) and K₃PO₄ (0.82 g, 3.846 mmol, 2.0 eq) in 1,4-dioxane (25 mL) was degassed with argon for 30 min. Then, trans-N,N'-dimethylcyclohexane-1,2-diamine (0.11 g, 0.769 mmol, 0.4 eq) and CuI (0.07 g, 0.384 mmol, 0.2 eq) were added and the reaction was stirred for 16 h at 90° C. in a sealed tube. After completion of the reaction (monitored by TLC), the reaction mixture was filtered through a celite bed and the celite bed was washed 2-3 times with 1,4-dioxane. The combined organic layers were concentrated to get the crude product which was purified by column chromatography (230-400 mesh silica gel; 0 to 2% MeOH in DCM) to afford trans-2,2-difluoro-N-((2R,3S)-2-(3-fluorophenyl)-1-(1-(1-methyl-6-oxo-1,6-dihydropyridin-3-yl)-1H-indazol-5-yl)-5-oxopyrrolidin-3-yl)propanamide. Further separation of enantiomers was done by preparative chiral HPLC to afford pure 2,2-difluoro-N-((2S,3R)-2-(3-fluorophenyl)-1-(1-(1-methyl-6-oxo-1,6-dihydropyridin-3-yl)-1H-indazol-5-yl)-5-oxopyrrolidin-3-yl)propanamide (0.13 g; RT=5.40 min; Column Name: Chiralpak IA (250×4.6 mm) 5 µm, Mobile Phase: Hexane/EA/EtOH/DEA: 50/25/25/0.1, Flow Rate: 1.0 ml/min) and 2,2-difluoro-N-((2R,3S)-2-(3-fluorophenyl)-1-(1-(1-methyl-6-oxo-1,6-dihydropyridin-3-yl)-1H-indazol-5-yl)-5-oxopyrrolidin-3-yl)propanamide (0.13 g; RT=7.14 min; Column Name: Chiralpak IA (250×4.6 mm) 5 µm, Mobile Phase: Hexane/EA/EtOH/DEA: 50/25/25/0.1, Flow Rate: 1.0 ml/min).

¹H NMR (DMSO-d₆) δ: 9.48-9.46 (m, 1H), 8.26-8.19 (m, 2H), 7.86 (s, 1H), 7.72-7.70 (m, 1H), 7.60-7.59 (m, 2H), 7.35-7.33 (m, 1H), 7.23-7.18 (m, 2H), 7.06 (s, 1H), 6.54 (d, 1H), 5.35-5.33 (m, 1H), 4.27-4.33 (s, 1H), 3.49 (s, 3H), 3.14-3.08 (m, 1H), 2.66-2.61 (m, 1H), 1.83-1.73 (m, 3H).

EXAMPLE 6

2,2-difluoro-N-((2R,3S)-2-(2-fluorophenyl)-1-(1-(1-methyl-6-oxo-1,6-dihydropyridin-3-yl)-1H-indazol-5-yl)-5-oxopyrrolidin-3-yl)propanamide

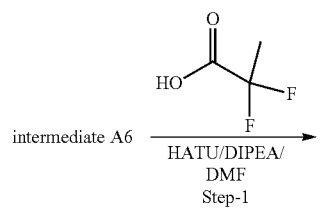

intermediate A6
HATU/DIPEA/
DMF
Step-1

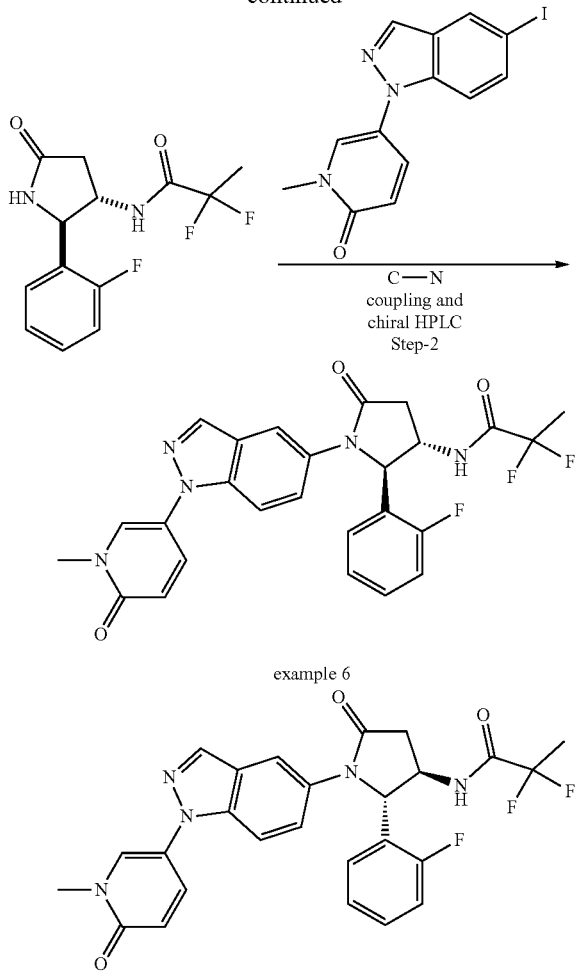

example 6

Step 1: To a stirred solution of 2,2-difluoropropanoic acid (0.68 g, 6.18 mmol, 1.2 eq) in DMF (8 mL), HATU (4.00 g, 10.30 mmol, 2.0 eq), DIPEA (4.5 mL, 25.75 mmol, 5.0 eq) and intermediate A6 (1.00 g, 5.15 mmol, 1.0 eq) were added at 0° C. and the reaction was then stirred at RT for 16 h. After completion of the reaction (monitored by TLC, TLC system 5% MeOH in DCM, Rf-0.3), the reaction mixture was diluted with EtOAc (25 mL) and washed with ice cold water (3×25 mL), dried over Na₂SO₄ and was concentrated to get the crude product which was purified by column chromatography (230-400 mesh silica gel; 0 to 2% MeOH-DCM;) to afford trans-2,2-difluoro-N-(2-(2-fluorophenyl)-5-oxopyrrolidin-3-yl)propanamide (0.51 g, 35%).

Step 2: A stirred solution of trans-2,2-difluoro-N-(2-(2-fluorophenyl)-5-oxopyrrolidin-3-yl)propanamide (0.25 g, 0.873 mmol, 1.0 eq), 5-(5-iodo-1H-indazol-1-yl)-1-methyl-pyridin-2(1H)-one (0.37 g, 1.047 mmol, 1.2 eq) and K₃PO₄ (0.37 g, 1.746 mmol, 2.0 eq) in 1,4-dioxane (10 mL) was degassed with argon for 30 min. Then, trans-N,N'-dimethylcyclohexane-1,2-diamine (0.05 g, 0.349 mmol, 0.4 eq) and CuI (0.03 g, 0.175 mmol, 0.2 eq) were added and the reaction mixture was stirred for 16 h at 90° C. in a sealed tube. After completion of the reaction (monitored by TLC, TLC system 5% MeOH in DCM, Rf-0.4), the reaction mixture was filtered through a celite bed and the celite bed was washed 2-3 times with 1,4-dioxane. The combined organic layers were concentrated to get the crude product which was purified by column chromatography (230-400 mesh silica gel; 0 to 2% MeOH in DCM) to afford the racemic trans-2,2-difluoro-N-(2-(2-fluorophenyl)-1-(1-(1-methyl-6-oxo-1,6-dihydropyridin-3-yl)-1H-indazol-5-yl)-5-oxopyrrolidin-3-yl)propanamide and further enantiomer separation was done by preparative chiral HPLC to afford 2,2-difluoro-N-((2S,3R)-2-(2-fluorophenyl)-1-(1-(1-methyl-6-oxo-1,6-dihydropyridin-3-yl)-1H-indazol-5-yl)-5-oxopyrrolidin-3-yl)propanamide (0.06 g, 13%; RT=5.90 min; Column Name: Chiralpak IA (250×4.6 mm) 5 μm, Mobile Phase: Hexane/EA/EtOH/DEA: 50/25/25/0.1, Flow Rate: 1.0 ml/min) and 2,2-difluoro-N-((2R,3S)-2-(2-fluorophenyl)-1-(1-(1-methyl-6-oxo-1,6-dihydropyridin-3-yl)-1H-indazol-5-yl)-5-oxopyrrolidin-3-yl)propanamide (0.07 g, 16%; RT=9.56 min; Column Name: Chiralpak IA (250×4.6 mm) 5 μm, Mobile Phase: Hexane/EA/EtOH/DEA: 50/25/25/0.1, Flow Rate: 1.0 ml/min).

$^1$H NMR (DMSO-$d_6$) δ: 9.45-9.43 (m, 1H), 8.27 (s, 1H), 8.19-8.18 (m, 1H), 7.78 (s, 1H), 7.72-7.68 (m, 1H), 7.62-7.59 (m, 1H), 7.48-7.45 (m, 1H), 7.42-7.38 (m, 1H), 7.27-7.25 (m, 1H), 7.16-7.08 (m, 2H), 6.54-6.51 (m, 1H), 5.53-5.52 (m, 1H), 4.48-4.46 (m, 1H), 3.49 (s, 3H), 3.16-3.09 (m, 1H), 2.70-2.64 (m, 1H), 1.80-1.71 (m, 3H).

EXAMPLE 7 trans-2,2-difluoro-N-(5-oxo-2-phenyl-1-(1-(pyridin-3-yl)-1H-indazol-5-yl)pyrrolidin-3-yl)propanamide

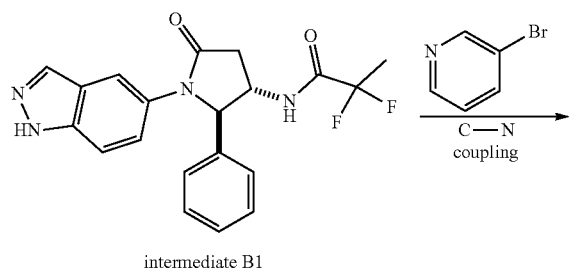

intermediate B1

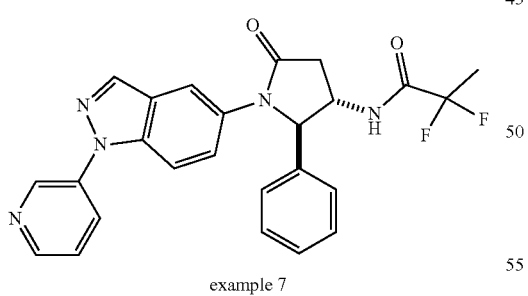

example 7

Starting from intermediate B1, example 7 was synthesized in analogy to the synthetic procedure described for example 9. Yield: 34%

$^1$H NMR (DMSO-$d_6$) δ: 9.51-9.50 (m, 1H), 8.99 (s, 1H), 8.58-8.57 (m, 1H), 8.39 (s, 1H), 8.18-8.16 (m, 1H), 7.91 (s, 1H), 7.85-7.82 (m, 1H), 7.69-7.67 (m, 1H), 7.61-7.58 (m, 1H), 7.37-7.23 (m, 5H), 5.34-5.32 (m, 1H), 4.31-4.23 (m, 1H), 3.14-3.08 (m, 1H), 2.65-2.60 (m, 1H), 1.83-1.74 (m, 3H).

EXAMPLE 9 trans-2,2-difluoro-N-(1-(1-(5-fluoropyridin-2-yl)-1H-indazol-5-yl)-5-oxo-2-phenylpyrrolidin-3-yl)propanamide

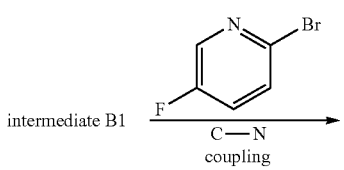

intermediate B1

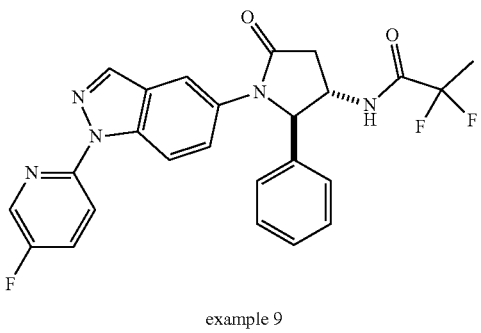

example 9

A stirred solution of intermediate B1 (0.200 g, 0.5208 mmol, 1.0 eq), 2-bromo-5-fluoropyridine (0.109 g, 0.624 mmol, 1.2 eq) and K$_3$PO$_4$ (0.220 g, 1.0416 mmol, 2.0 eq) in 1,4-dioxane (10 mL) was degassed with argon for 30 min. Then, trans-N,N'-dimethylcyclohexane-1,2-diamine (0.030 g, 0.2083 mmol, 0.4 eq) and CuI (0.020 g, 0.1041 mmol, 0.2 eq) were added and the reaction was stirred for 16 h at 90° C. in a sealed tube. After completion of the reaction, (monitored by TLC, TLC system 5% MeOH in DCM, Rf-0.4), the reaction mixture was filtered through a celite bed and the celite bed was washed 2-3 times with 1,4-dioxane. The combined organic layers were concentrated to get the crude product which was purified by column chromatography (230-400 mesh silica gel; 0 to 2% MeOH in DCM) to afford the compound and further purification was done by Prep HPLC to afford trans-2,2-difluoro-N-(1-(1-(5-fluoropyridin-2-yl)-1H-indazol-5-yl)-5-oxo-2-phenylpyrrolidin-3-yl)propanamide (0.057 g, 23%).

$^1$H NMR (DMSO-$d_6$) δ: 9.51-9.49 (m, 1H), 8.53-8.50 (m, 2H), 8.39 (s, 1H), 7.99-7.92 (m, 3H), 7.72-7.69 (m, 1H), 7.36-7.29 (m, 4H), 7.23-7.20 (m, 1H), 5.35-5.33 (m, 1H), 4.34-4.26 (m, 1H), 3.14-3.08 (m, 1H), 2.66-2.61 (m, 1H), 1.83-1.73 (m, 3H).

EXAMPLE 13

5-methyl-N-(trans-1-(1-(1-methyl-6-oxo-1,6-dihydropyridin-3-yl)-1H-indazol-5-yl)-5-oxo-2-phenylpyrrolidin-3-yl)thiazole-2-carboxamide

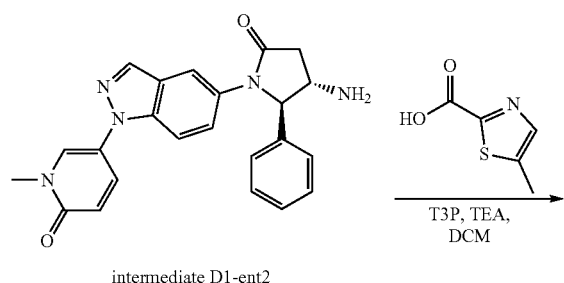

intermediate D1-ent2

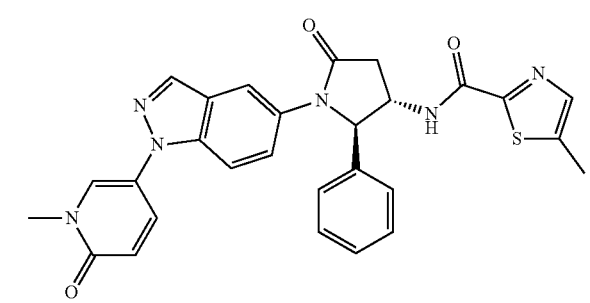

example 13

Triethylamine (0.09 ml, 0.626 mmol, 5.0 eq) and propylphosphonic anhydride solution (≥50 wt. % in EtOAc, T3P, 0.15 ml, 0.250 mmol, 2.0 eq) were added to a solution of 5-methylthiazole-2-carboxylic acid (20 mg, 0.138 mmol, 1.1 eq) in DCM (1.3 ml) and the reaction mixture was stirred at RT for 30 min. To this stirred mixture, a solution of 5-[5-(3-amino-5-oxo-2-phenyl-pyrrolidin-1-yl)indazol-1-yl]-1-methyl-pyridin-2-one (50 mg, 0.125 mmol, 1.0 eq) in DCM (1.3 ml) was added slowly in a dropwise fashion, and the resulting mixture was stirred at RT overnight. The reaction mixture was then diluted with DCM, a sat. NaHCO₃ solution was added, and the phases were separated through a hydrophobic frit. After removal of the solvent under reduced pressure, the crude residue was purified by HPLC to afford 5-(5-((2R,3S)-3-amino-5-oxo-2-phenylpyrrolidin-1-yl)-1H-indazol-1-yl)-1-methylpyridin-2(1H)-one (39 mg, 59%).

$^1$H NMR (DMSO-d$_6$) δ: 9.53 (d, 1H), 8.24 (s, 1H), 8.17 (d, 1H), 7.85-7.81 (m, 1H), 7.75 (d, 1H), 7.71 (dd, 1H), 7.63-7.53 (m, 2H), 7.40-7.33 (m, 2H), 7.30 (t, 2H), 7.25-7.18 (m, 1H), 6.54 (d, 1H), 5.45 (d, 1H), 4.51-4.43 (m, 1H), 3.50 (s, 3H), 3.09 (dd, 1H), 2.81-2.72 (m, 1H), 2.52 (d, 3H).

EXAMPLE 15

2,2-difluoro-N-((2R,3S)-2-(4-fluoro-3-methoxyphenyl)-1-(1-(1-methyl-6-oxo-1,6-dihydropyridin-3-yl)-1H-indazol-5-yl)-5-oxopyrrolidin-3-yl)propanamide

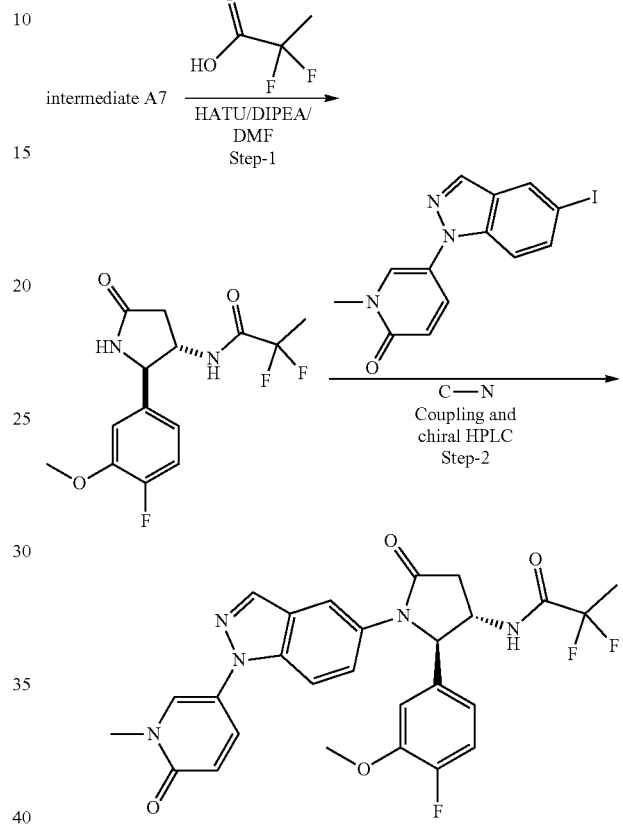

example 15

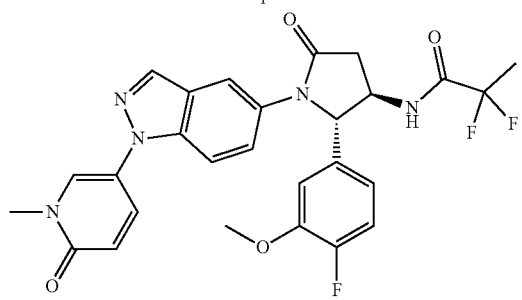

Step 1: To a stirred solution of intermediate A7 (3.12 g, 13.92 mmol, 1.0 eq) in DMF (30 mL), HATU (7.90 g, 20.89 mmol, 1.5 eq), DIPEA (12.0 ml, 69.64 mmol, 5.0 eq) and 2,2-difluoropropanoic acid (2.00 g, 18.10 mmol, 1.3 eq) were added and the reaction mixture was stirred for 16 h at RT. After completion, the reaction mixture was diluted with EtOAc and was washed with ice cold water, sat. NaHCO₃ and sat. NH₄Cl solution. The combined organic layers were concentrated to get the crude product which was purified by column chromatography (100-200 mesh silica gel; 2% MeOH-DCM; R$_f$-value-0.5) to afford trans-2,2-difluoro-N-(2-(4-fluoro-3-methoxyphenyl)-5-oxopyrrolidin-3-yl)propanamide (3.50 g, 80%).

Step 2: A stirred solution of trans-2,2-difluoro-N-(2-(4-fluoro-3-methoxyphenyl)-5-oxopyrrolidin-3-yl)propanamide (0.30 g, 0.95 mmol, 1:0 eq), 5-(5-iodo-1H-indazol-1-yl)-1-methylpyridin-2(1H)-one (0.40 g, 1.13 mmol, 1.2 eq) and $K_3PO_4$ (0.40 g, 1.89 mmol, 2.0 eq) in 1,4-dioxane (20 mL) was degassed with argon for 15 min. Then, trans-N,N'-dimethylcyclohexane-1,2-diamine (0.06 g, 0.38 mmol, 0.4 eq) and CuI (0.04 g, 0.19 mmol, 0.2 eq) were added and the reaction was stirred for 16 h at 90° C. After completion, the reaction mixture was filtered through a celite bed and the celite bed was washed 2-3 times with EtOAc. The combined organic layers were concentrated to get the crude product which was purified by column chromatography (100-200 mesh silica gel; 5% MeOH-DCM; $R_f$-value-0.5) to afford the racemic trans-2,2-difluoro-N-(2-(4-fluoro-3-methoxyphenyl)-1-(1-(1-methyl-6-oxo-1,6-dihydropyridin-3-yl)-1H-indazol-5-yl)-5-oxopyrrolidin-3-yl)propanamide. Further enantiomer separation was done by preparative chiral HPLC to afford 2,2-difluoro-N-((2S,3R)-2-(4-fluoro-3-methoxyphenyl)-1-(1-(1-methyl-6-oxo-1,6-dihydropyridin-3-yl)-1H-indazol-5-yl)-5-oxopyrrolidin-3-yl)propanamide (0.10 g; RT=10.31 min, Chiralpak ID (250×4.6 mm) 5 μm, Mobile phase: EtOH, Flow Rate: 0.5 ml/min) and 2,2-difluoro-N-((2R,3S)-2-(4-fluoro-3-methoxyphenyl)-1-(1-(1-methyl-6-oxo-1,6-dihydropyridin-3-yl)-1H-indazol-5-yl)-5-oxopyrrolidin-3-yl)propanamide (0.10 g; RT=13.00 min, Chiralpak ID (250×4.6 mm) 5 μm; Mobile phase: EtOH, Flow Rate: 0.5 ml/min) as a white solid.

$^1$H NMR (DMSO-$d_6$) δ: 9.43-9.41 (m, 1H), 8.26 (s, 1H), 8.20 (d, 1H), 7.84 (s, 1H), 7.73-7.69 (m, 1H), 7.62-7.54 (m, 2H), 7.19-7.17 (m, 1H), 7.12-7.07 (m, 1H), 6.87-6.84 (m, 1H), 6.54-6.52 (m, 1H), 5.29-5.27 (m, 1H), 4.32-4.30 (m, 1H), 3.78 (s, 3H), 3.49 (s, 3H), 3.12-3.06 (m, 1H), 2.66-2.61 (m, 1H), 1.83-1.73 (m, 3H).

EXAMPLE 17

2,2-difluoro-N-((2R,3S)-2-(4-fluorophenyl)-1-(1-(1-methyl-6-oxo-1,6-dihydropyridin-3-yl)-1H-indazol-5-yl)-5-oxopyrrolidin-3-yl)propanamide

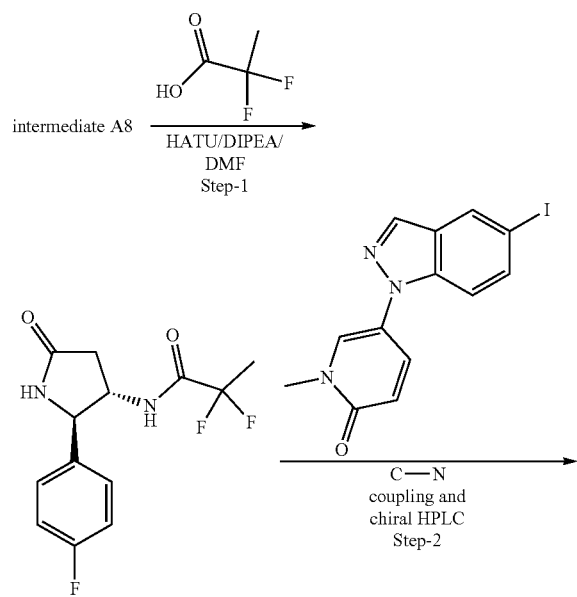

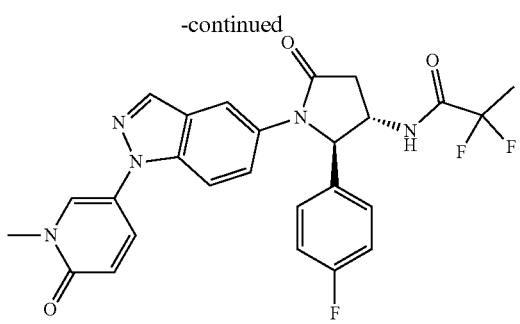

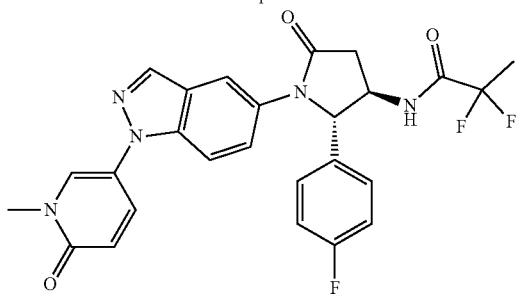

example 17

Step 1: To a stirred solution of 2,2-difluoro-propionic acid (0.44 g, 4.020 mmol, 1.2 eq) in DMF (6 mL), HATU (2.55 g, 6.701 mmol, 2.0 eq), DIPEA (2.95 mL, 6.701 mmol, 5.0 eq), and intermediate 8 (0.65 g, 3.350 mmol, 1.0 eq) were added at 0° C. and the reaction was stirred at RT for 16 h. After completion of the reaction (monitored by TLC), the reaction mixture was diluted with EtOAc (25 mL), washed with ice cold water (3×25 mL), dried over $Na_2SO_4$ and was concentrated under reduced pressure to get the crude product, which was purified by column chromatography (230-400 mesh silica gel; 2% MeOH-DCM) to afford trans-2,2-difluoro-N-(2-(4-fluorophenyl)-5-oxopyrrolidin-3-yl)propanamide (0.60 g, 63%).

Step 2: A stirred solution of trans-2,2-difluoro-N-(2-(4-fluorophenyl)-5-oxopyrrolidin-3-yl)propanamide (0.30 g, 1.048 mmol, 1.0 eq), 5-(5-iodo-1H-indazol-1-yl)-1-methyl-pyridin-2(1H)-one (0.44 g, 1.258 mmol, 1.2 eq) and $K_3PO_4$ (0.44 g, 2.097 mmol, 2.0 eq) in 1,4-dioxane (10 mL) was degassed with argon for 30 min. Then, trans-N,N'-dimethylcyclohexane-1,2-diamine (0.06 g, 0.419 mmol, 0.4 eq) and CuI (0.04 g, 0.209 mmol, 0.2 eq) were added and the reaction was stirred for 16 h at 90° C. in a sealed tube. After completion of the reaction (monitored by TLC), the reaction mixture was filtered through a celite bed and the celite bed was washed 2-3 times with 1,4-dioxane. The combined organic layers were concentrated to get the crude product which was purified by column chromatography (230-400 mesh silica gel; 2% MeOH in DCM) to afford the racemic trans-2,2-difluoro-N-(2-(4-fluorophenyl)-1-(1-(1-methyl-6-oxo-1,6-dihydropyridin-3-yl)-1H-indazol-5-yl)-5-oxopyrrolidin-3-yl)propanamide. Further enantiomer separation was done by preparative chiral HPLC to afford 2,2-difluoro-N-((2S,3R)-2-(4-fluorophenyl)-1-(1-(1-methyl-6-oxo-1,6-dihydropyridin-3-yl)-1H-indazol-5-yl)-5-oxopyrrolidin-3-yl) propanamide (0.12 g, 23%; RT=6.17 min; Column Name: Chiralpak IA (250×4.6 mm) 5 μm, Mobile Phase: Hexane/ EA/EtOH/DEA: 50/25/25/0.1, Flow Rate: 1.0 ml/min) and 2,2-difluoro-N-((2R,3S)-2-(4-fluorophenyl)-1-(1-(1-methyl-6-oxo-1,6-dihydropyridin-3-yl)-1H-indazol-5-yl)-5-oxopyrrolidin-3-yl)propanamide (0.12 g, 22%; RT=8.46 min; Column Name: Chiralpak IA (250×4.6 mm) 5 μm, Mobile Phase: Hexane/EA/EtOH/DEA: 50/25/25/0.1, Flow Rate: 1.0 ml/min).

$^1$H NMR (DMSO-d$_6$) δ: 9.46-9.44 (m, 1H), 8.25 (s, 1H), 8.19-8.18 (m, 1H), 7.83 (s, 1H), 7.72-7.69 (m, 1H), 7.61-7.53 (m, 2H), 7.42-7.38 (m, 2H), 7.15-7.11 (m, 2H), 6.54 (d, 1H), 5.33-5.31 (m, 1H), 4.32-4.26 (m, 1H), 3.49 (s, 3H), 3.12-3.05 (m, 1H), 2.66-2.61 (m, 1H), 2.49 (s, 1H), 1.82-1.72 (m, 3H).

EXAMPLE 18

1-fluoro-N-((2R,3S)-1-(1-(1-methyl-6-oxo-1,6-dihydropyridin-3-yl)-1H-indazol-5-yl)-5-oxo-2-phenylpyrrolidin-3-yl)cyclopropanecarboxamide

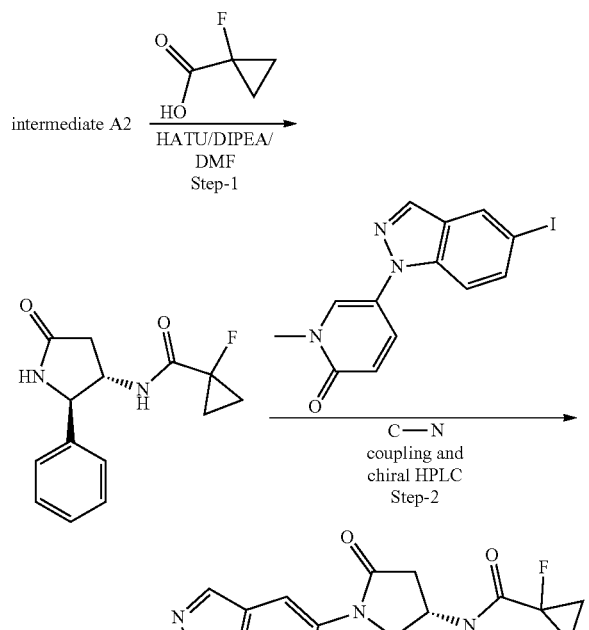

example 18

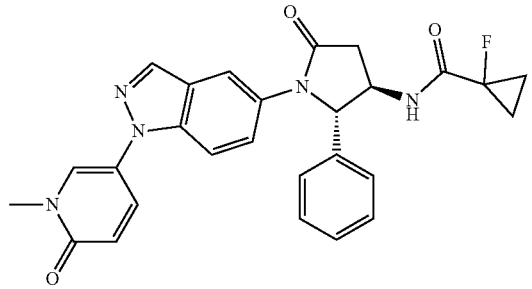

Step 1: To a stirred solution of 1-fluorocyclopropane-1-carboxylic acid (0.71 g, 6.818 mmol, 1.2 eq) in DMF (10 mL), HATU (4.32 g, 11.364 mmol, 2.0 eq), DIPEA (5.0 mL, 28.409 mmol, 5.0 eq) and intermediate A2 (1.00 g, 5.682 mmol, 1.0 eq) were added at 0° C. and the reaction was then stirred at RT for 16 h. After completion of the reaction (monitored by TLC, TLC system 5% MeOH in DCM, Rf-0.3), the reaction mixture was diluted with EtOAc (35 mL), washed with ice cold water (3×25 mL), dried over Na$_2$SO$_4$ and concentrated to get the crude product which was purified by column chromatography (230-400 mesh silica gel; 0 to 3% MeOH-DCM;) to afford trans-1-fluoro-N-(5-oxo-2-phenylpyrrolidin-3-yl)cyclopropanecarboxamide (0.64 g, 43%).

Step 2: A stirred solution of trans-1-fluoro-N-(5-oxo-2-phenylpyrrolidin-3-yl)cyclopropanecarboxamide (0.32 g, 1.220 mmol, 1.0 eq), 5-(5-iodo-1H-indazol-1-yl)-1-methylpyridin-2(1H)-one (0.51 g, 1.465 mmol, 1.2 eq) and K$_3$PO$_4$ (0.52 g, 2.441 mmol, 2.0 eq) in 1,4 dioxane (20 mL) was degassed with argon for 30 min. Then, trans-N,N'-dimethylcyclohexane-1,2-diamine (0.07 g, 0.480 mmol, 0.4 eq) and CuI (0.05 g, 0.244 mmol, 0.2 eq) were added and the reaction was stirred for 16 h at 90° C. in a sealed tube. After completion of the reaction (monitored by TLC, TLC system 5% MeOH in DCM, Rf-0.4), the reaction mixture was filtered through a celite bed and the celite bed was washed 2-3 times with 1,4-dioxane. The combined organic layers were concentrated to get the crude product which was purified by column chromatography (230-400 mesh silica gel; 0 to 2% MeOH in DCM) to afford the racemic trans-1-fluoro-N-(1-(1-(1-methyl-6-oxo-1,6-dihydropyridin-3-yl)-1H-indazol-5-yl)-5-oxo-2-phenylpyrrolidin-3-yl)cyclopropanecarboxamide. Further enantiomer separation was done by preparative chiral HPLC to afford 1-fluoro-N-((2S, 3R)-1-(1-(1-methyl-6-oxo-1,6-dihydropyridin-3-yl)-1H-indazol-5-yl)-5-oxo-2-phenylpyrrolidin-3-yl)cyclopropanecarboxamide (0.13 g, 22%; RT=6.68 min, Column Name: Chiralpak IA (250×4.6 mm) 5 μm, Mobile Phase: Hexane/EA/EtOH/DEA: 50/25/25/0.1, Flow Rate: 1.0 ml/min) and 1-fluoro-N-((2R,3S)-1-(1-(1-methyl-6-oxo-1,6-dihydropyridin-3-yl)-1H-indazol-5-yl)-5-oxo-2-phenylpyrrolidin-3-yl)cyclopropanecarboxamide (0.11 g, 18%; RT=8.97 min, Column Name: Chiralpak IA (250×4.6 mm) 5 μm, Mobile Phase: Hexane/EA/EtOH/DEA: 50/25/25/0.1, Flow Rate: 1.0 ml/min).

$^1$H NMR (DMSO-d$_6$) δ: 9.18-9.17 (m, 1H), 8.24 (s, 1H), 8.18 (s, 1H), 7.84 (s, 1H), 7.72-7.69 (m, 1H), 7.59 (s, 2H), 7.36-7.34 (m, 2H), 7.31-7.27 (m, 2H), 7.23-7.21 (m, 1H), 6.54-6.51 (m, 1H), 5.35-5.34 (m, 1H), 4.36-4.28 (m, 1H), 3.49 (s, 3H), 3.09-3.03 (m, 1H), 2.67-2.62 (m, 1H), 1.35-1.29 (m, 2H), 1.22-1.19 (m, 2H).

EXAMPLE 22 trans-2,2-difluoro-N-(1-(1-(6-methoxypyridin-3-yl)-1H-indazol-5-yl)-5-oxo-2-phenylpyrrolidin-3-yl)propanamide

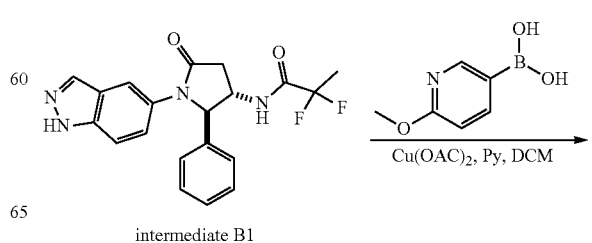

intermediate B1

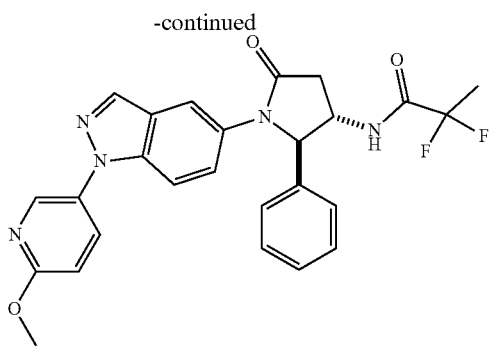

example 22

To a stirred solution of intermediate B1 (0.250 g, 0.651 mmol, 1.0 eq), (6-methoxypyridin-3-yl)boronic acid (0.200 g, 1.302 mmol, 2.0 eq) and pyridine (0.1 mL, 1.302 mmol, 2.0 eq) in DCM (20 mL) was added Cu(OAc)$_2$ (0.177 g, 0.976 mmol, 1.5 eq) and the reaction was stirred for 16 h at RT. After completion of the reaction (monitored by TLC, TLC system 5% MeOH in DCM, Rf-0.4), the solvent was removed under reduced pressure and the residue was partitioned between DCM and water. The aqueous layer was extracted twice with DCM (2×50 mL). The combined organic layers were washed with brine, dried over Na$_2$SO$_4$, filtered and concentrated under reduced pressure. The crude product was purified by preparative HPLC column chromatography to afford trans-2,2-difluoro-N-(1-(1-(6-methoxypyridin-3-yl)-1H-indazol-5-yl)-5-oxo-2-phenylpyrrolidin-3-yl)propanamide (0.105 g, 33%).

$^1$H NMR (DMSO-d$_6$) δ: 9.50-9.49 (m, 1H), 8.51-8.50 (m, 1H), 8.31 (s, 1H), 8.05-8.02 (m, 1H), 7.86 (s, 1H), 7.68-7.62 (m, 2H), 7.36-7.29 (m, 4H), 7.24-7.21 (m, 1H), 7.02 (d, 1H), 5.32-5.31 (m, 1H), 4.28-4.26 (m, 1H), 3.92 (s, 3H), 3.13-3.07 (m, 1H), 2.66-2.59 (m, 1H), 1.83-1.73 (m, 3H).

EXAMPLE 23 trans-2,2-difluoro-N-(5-oxo-2-phenyl-1-(1-(pyridin-4-yl)-1H-indazol-5-yl)pyrrolidin-3-yl)propanamide

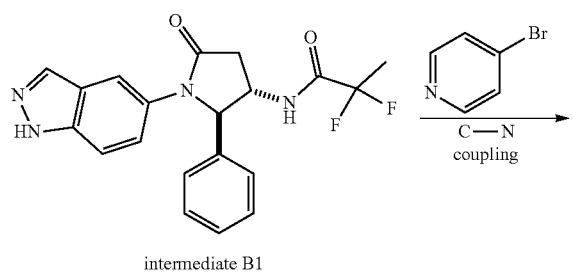

intermediate B1

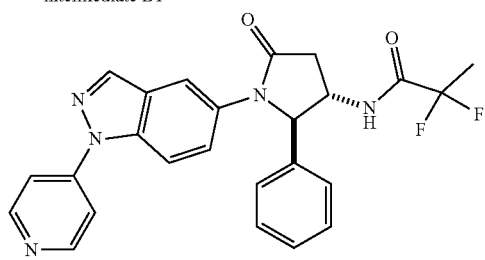

example 23

A stirred solution of intermediate B1 (0.200 g, 0.521 mmol, 1.0 eq), 4-bromo-pyridine (0.120 g, 0.624 mmol, 1.2 eq) and K$_3$PO$_4$ (0.276 g, 1.302 mmol, 2.5 eq) in 1,4-dioxane (10 mL) was degassed with argon for 30 min. Then, trans-N,N'-dimethylcyclohexane-1,2-diamine (0.030 g, 0.208 mmol, 0.4 eq) and CuI (0.020 g, 0.104 mmol, 0.2 eq) were added and the reaction was stirred for 16 h at 90° C. in a sealed tube. After completion of the reaction, (monitored by TLC, TLC system 5% methanol in DCM, Rf-0.4), the reaction mixture was filtered through a celite bed and the celite bed was washed 2-3 times with 1,4-dioxane. The combined organic layers were concentrated to get the crude product which was first purified by column chromatography (230-400 mesh silica gel; 0 to 2% MeOH in DCM) to afford the desired product which was further purified by preparative HPLC to afford trans-2,2-difluoro-N-(5-oxo-2-phenyl-1-(1-(pyridin-4-yl)-1H-indazol-5-yl)pyrrolidin-3-yl)propanamide (0.052 g, 22%).

$^1$H NMR (DMSO-d$_6$) δ: 9.52-9.50 (m, 1H), 8.68-8.66 (m, 2H), 8.45 (s, 1H), 8.06-8.03 (m, 1H), 7.95 (s, 1H), 7.85-7.84 (m, 2H), 7.75-7.72 (m, 1H), 7.37-7.30 (m, 4H), 7.25-7.23 (m, 1H), 5.36-5.34 (m, 1H), 4.32-4.26 (m, 1H), 3.15-3.08 (m, 1H), 2.66-2.60 (m, 1H), 1.83-1.74 (m, 3H).

EXAMPLE 24 trans-2,2-difluoro-N-(1-(1-(6-methylpyridin-3-yl)-1H-indazol-5-yl)-5-oxo-2-phenylpyrrolidin-3-yl)propanamide

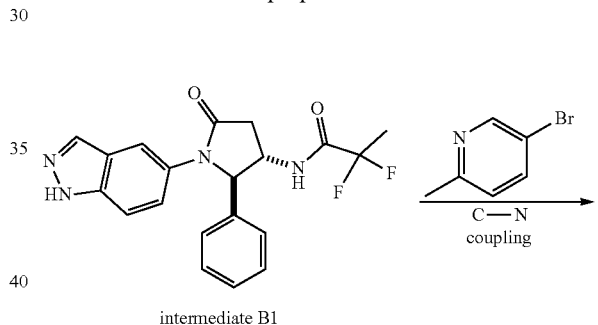

intermediate B1

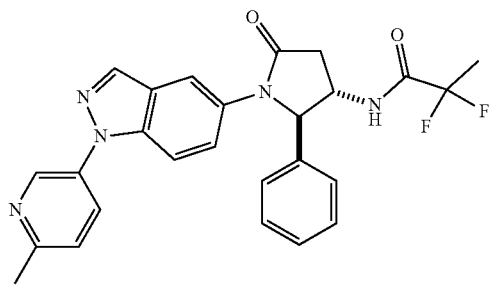

example 24

A stirred solution of intermediate B1 (0.200 g, 0.521 mmol, 1.0 eq), 5-bromo-2-methylpyridine (0.106 g, 0.624 mmol, 1.2 eq) and K$_3$PO$_4$ (0.220 g, 1.042 mmol, 2.0 eq) in 1,4-dioxane (10 mL) was degassed with argon for 30 min. Then, trans-N,N'-dimethylcyclohexane-1,2-diamine (0.030 g, 0.208 mmol, 0.4 eq) and CuI (0.020 g, 0.104 mmol, 0.2 eq) were added and the reaction was stirred for 16 h at 90° C. in a sealed tube. After completion of the reaction (monitored by TLC, TLC system 5% MeOH in DCM, Rf-0.4), the reaction mixture was filtered through a celite bed and the celite bed was washed 2-3 times with 1,4-dioxane. The combined organic layer was concentrated to get the crude product which was purified by column chromatography (230-400 mesh silica gel; 0 to 2% MeOH in DCM) to afford the crude compound and further purification was done by preparative HPLC to afford trans-2,2-difluoro-N-(1-(1-(6-methylpyridin-3-yl)-1H-indazol-5-yl)-5-oxo-2-phenylpyrrolidin-3-yl)propanamide (0.041 g, 17%).

$^1$H NMR (DMSO-d$_6$) δ: 9.51-9.50 (m, 1H), 8.81 (s, 1H), 8.35 (s, 1H), 8.04-8.02 (m, 1H), 7.89 (s, 1H), 7.78-7.75 (m, 1H), 7.67-7.65 (m, 1H), 7.45-7.43 (m, 1H), 7.36-7.29 (m, 3H), 7.24-7.23 (m, 1H), 5.33-5.31 (m, 1H), 4.30-4.24 (m, 1H), 3.14-3.09 (m, 1H), 2.64-2.59 (m, 1H), 2.54 (s, 3H), 1.83-1.73 (m, 3H).

EXAMPLE 25 trans-2,2-difluoro-N-(1-(1-(2-methylpyridin-4-yl)-1H-indazol-5-yl)-5-oxo-2-phenylpyrrolidin-3-yl)propanamide

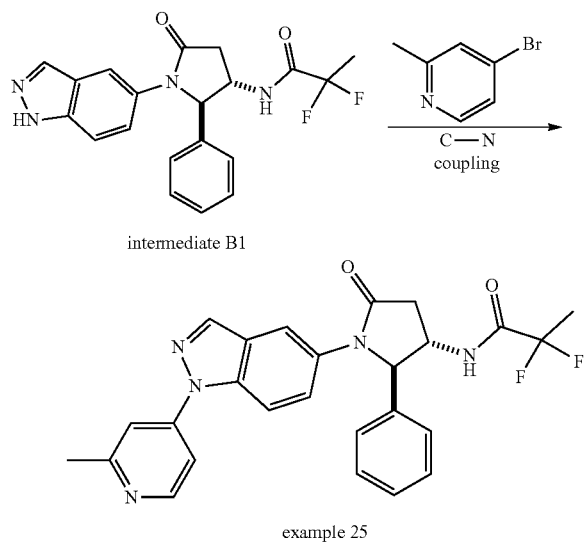

intermediate B1 example 25

Starting from intermediate B1 and 4-bromo-2-methylpyridine, example 25 was synthesized in analogy to the synthetic procedure described for example 24.

$^1$H NMR (DMSO-d$_6$) δ: 9.52-9.50 (m, 1H), 8.53-8.52 (m, 1H), 8.43 (s, 1H), 8.05 (d, 1H), 7.95 (s, 1H), 7.72-7.63 (m, 3H), 7.37-7.23 (m, 5H), 5.35-5.34 (m, 1H), 4.31-4.26 (m, 1H), 3.15-3.08 (m, 1H), 2.66-2.60 (m, 1H), 2.55 (s, 3H), 1.83-1.74 (m, 3H).

EXAMPLE 26

1-methyl-N-((2R,3S)-1-(1-(1-methyl-6-oxo-1,6-dihydropyridin-3-yl)-1H-indazol-5-yl)-5-oxo-2-phenylpyrrolidin-3-yl)cyclopropane-1-carboxamide

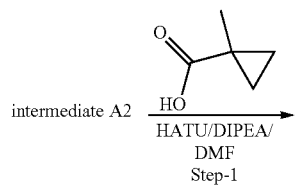

intermediate A2

HATU/DIPEA/DMF
Step-1

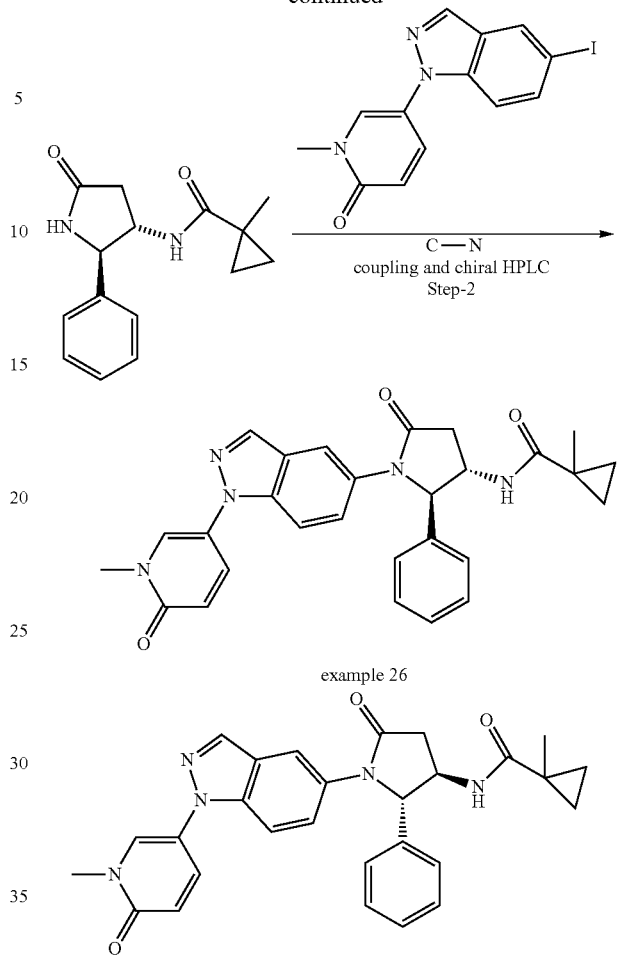

example 26

Step 1: To a stirred solution of 1-methylcyclopropane-1-carboxylic acid (0.68 g, 6.818 mmol, 1.2 eq) in DMF (10 ml,), HATU (4.32 g, 11.363 mmol, 2.0 eq), DIPEA (5.0 mL, 28.409 mmol, 5.0 eq) and intermediate A2 (1.00 g, 5.682 mmol, 1.0 eq) were added at 0° C. and the reaction was then stirred at RT for 16 h. After completion of the reaction (monitored by TLC, TLC system 5% MeOH in DCM, Rf-0.3), the reaction mixture was diluted with EtOAc (35 mL), washed with ice cold water (3×25 mL), dried over Na$_2$SO$_4$ and concentrated under reduced pressure to get the crude product which was purified by column chromatography (230-400 mesh silica gel; 0 to 3% MeOH-DCM) to afford trans-1-methyl-N-(5-oxo-2-phenylpyrrolidin-3-yl)cyclopropanecarboxamide (0.78 g, 53%).

Step 2: A stirred solution of trans-1-methyl-N-(5-oxo-2-phenylpyrrolidin-3-yl)cyclopropanecarboxamide (0.31 g, 1.20 mmol, 1.0 eq), 5-(5-iodo-1H-indazol-1-yl)-1-methylpyridin-2(1H)-one (0.51 g, 1.44 mmol, 1.2 eq) and K$_3$PO$_4$ (0.51 g, 2.40 mmol, 2.0 eq) in 1,4-dioxane (30 mL) was degassed with argon for 30 min. Then, trans-N,N'-dimethylcyclohexane-1,2-diamine (0.07 g, 0.48 mmol, 0.4 eq) and CuI (0.05 g, 0.24 mmol, 0.2 eq) were added and the reaction was stirred for 16 h at 90° C. in a sealed tube. After completion of the reaction (monitored by TLC, TLC system 5% MeOH in DCM, Rf-0.4), the reaction mixture was filtered through a celite bed and the celite bed was washed 2-3 times with 1,4-dioxane. The combined organic layers were concentrated to get the crude product which was purified by column chromatography (230-400 mesh silica gel; 0 to 2% MeOH in DCM) to afford the racemic trans-1-methyl-N-(1-(1-(1-methyl-6-oxo-1,6-dihydropyridin-3-yl)-1H-indazol-5-yl)-5-oxo-2-phenylpyrrolidin-3-yl)cyclopropanecarboxamide. Further enantiomer separation was done by preparative chiral HPLC to afford 1-methyl-N-((2S,3R)-1-(1-(1-methyl-6-oxo-1,6-dihydropyridin-3-yl)-1H-indazol-5-yl)-5-oxo-2-phenylpyrrolidin-3-yl)cyclopropanecarboxamide (0.12 g, 21%; RT=6.47 min, Column Name: Chiralpak IA (250×4.6 mm) 5 μm, Mobile Phase: Hexane/EA/EtOH/DEA: 50/25/25/0.1, Flow Rate: 1.0 ml/min) and 1-methyl-N-((2R,3S)-1-(1-(1-methyl-6-oxo-1,6-dihydropyridin-3-yl)-1H-indazol-5-yl)-5-oxo-2-phenylpyrrolidin-3-yl)cyclopropanecarboxamide (0.09 g, 16%; RT=8.22 min, Column Name: Chiralpak IA (250×4.6 mm) 5 μm, Mobile Phase: Hexane/EA/EtOH/DEA: 50/25/25/0.1, Flow Rate: 1.0 ml/min).

$^1$H NMR (DMSO-$d_6$) δ: 8.24 (s, 1H), 8.18-8.15 (m, 2H), 7.84 (s, 1H), 7.71-7.70 (m, 1H), 7.59 (s, 2H), 7.34-7.27 (m, 4H), 7.22-7.20 (m, 1H), 6.54 (d, 1H), 5.25-5.23 (m, 1H), 4.24-4.16 (m, 1H), 3.49 (s, 3H), 3.04-2.97 (m, 1H), 2.61-2.56 (m, 1H), 1.30 (s, 3H), 1.01-0.99 (m, 2H), 0.55-0.54 (m, 2H).

EXAMPLE 27 trans-2,2-difluoro-N-(1-(1-(2-methoxypyridin-4-yl)-1H-indazol-5-yl)-5-oxo-2-phenylpyrrolidin-3-yl)propanamide

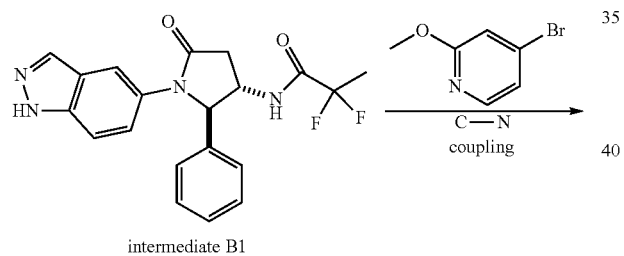

intermediate B1

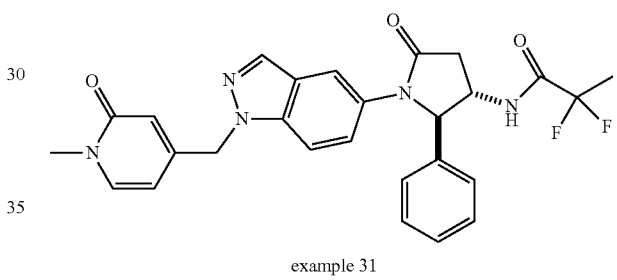

example 27

Starting from intermediate B1 and 4-bromo-2-methoxypyridine, example 27 was synthesized in analogy to the synthetic procedure described for example 24.

$^1$H NMR (DMSO-$d_6$) δ: 9.51-9.50 (m, 1H), 8.42 (s, 1H), 8.28-8.26 (m, 1H), 8.01-7.99 (m, 1H), 7.93 (s, 1H), 7.74-7.72 (m, 1H), 7.48-7.47 (m, 1H), 7.36-7.30 (m, 4H), 7.25-7.23 (m, 1H), 7.16 (s, 1H), 5.35-5.33 (m, 1H), 4.30-4.23 (m, 1H), 3.91 (s, 3H), 3.15-3.08 (m, 1H), 2.65-2.60 (m, 1H), 1.83-1.74 (m, 3H).

EXAMPLE 31 trans-2,2-difluoro-N-(1-(1-((1-methyl-2-oxo-1,2-dihydropyridin-4-yl)methyl)-1H-indazol-5-yl)-5-oxo-2-phenylpyrrolidin-3-yl)propanamide

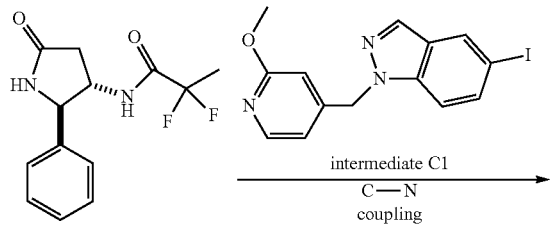

example 31

A stirred solution of trans-2,2-difluoro-N-(5-oxo-2-phenylpyrrolidin-3-yl)propanamide (for synthesis see example 4) (0.200 g, 0.746 mmol, 1.0 eq), intermediate C1 (0.326 g, 0.985 mmol, 1.2 eq) and $K_3PO_4$ (0.316 g, 1.492 mmol, 2.0 eq) in 1,4-dioxane (15 mL) was degassed with argon for 30 min. Then, trans-2,2-difluoro-N-(5-oxo-2-phenylpyrrolidin-3-yl)propanamide (0.042 g, 0.298 mmol, 0.4 eq) and CuI (0.028 g, 0.149 mmol, 0.2 eq) were added and the reaction was stirred for 16 h at 90° C. in a sealed tube. After completion of the reaction (monitored by TLC, TLC system 5% methanol in DCM, Rf-0.4), the reaction mixture was filtered through a celite bed and the celite bed was washed 2-3 times with 1,4-dioxane. The combined organic layers were concentrated to get the crude product which was purified by preparative HPLC to afford trans-2,2-difluoro-N-(1-(1-((1-methyl-2-oxo-1,2-dihydropyridin-4-yl)methyl)-1H-indazol-5-yl)-5-oxo-2-phenylpyrrolidin-3-yl)propanamide (0.130 g, 34%).

$^1$H NMR (DMSO-$d_6$) δ: 9.47-9.45 (m, 1H), 8.07 (s, 1H), 8.03-8.02 (m, 1H), 7.76 (s, 1H), 7.59-7.57 (m, 1H), 7.51-7.49 (m, 1H), 7.34-7.28 (m, 4H), 7.23-7.20 (m, 1H), 6.66 (d, 1H), 6.45 (s, 1H), 5.59 (s, 2H), 5.27-5.26 (m, 1H), 4.27-4.24 (m, 1H), 3.76 (s, 3H), 3.10-3.04 (m, 1H), 2.63-2.57 (m, 1H), 1.82-1.73 (m, 3H).

EXAMPLE 32 trans-2,2-difluoro-N-(1-(1-((1-methyl-1H-pyrazol-3-yl)methyl)-1H-indazol-5-yl)-5-oxo-2-phenylpyrrolidin-3-yl)propanamide

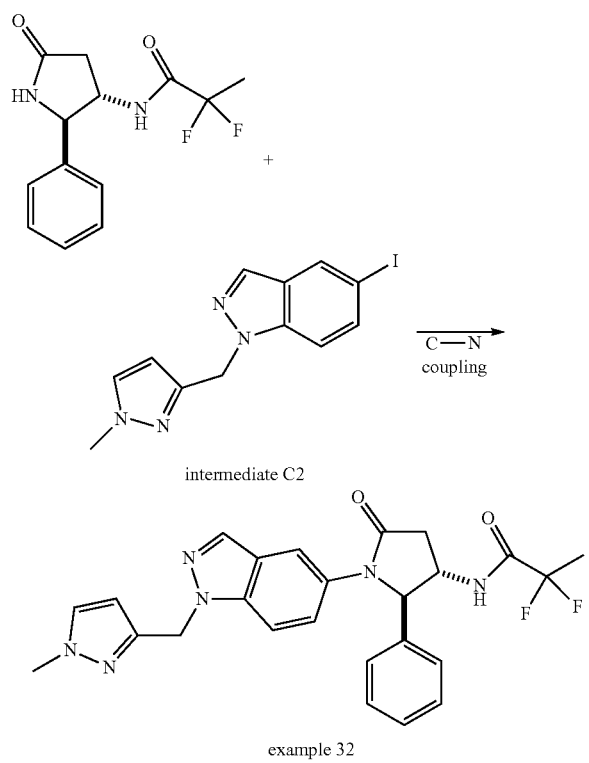

Starting from intermediate C2 and trans-2,2-difluoro-N-(5-oxo-2-phenylpyrrolidin-3-yl)propanamide, example 32 was synthesized in analogy to the synthetic procedure described for example 31.

$^1$H NMR (DMSO-$d_6$) δ: 9.42-9.44 (m, 1H), 7.93 (s, 1H), 7.68 (s, 1H), 7.52-7.55 (m, 1H), 7.49 (s, 1H), 7.43-7.45 (m, 1H), 7.24-7.30 (m, 4H), 7.16-7.19 (m, 1H), 5.97 (s, 1H), 5.42 (s, 2H), 5.22-5.23 (m, 1H), 4.22-4.23 (m, 1H), 3.70 (s, 3H), 3.00-3.06 (m, 1H), 2.54-2.59 (m, 1H), 1.69-1.79 (m, 3H).

EXAMPLE 33 trans-2,2-difluoro-N-(1-(1-((6-methoxypyridin-3-yl)methyl)-1H-indazol-5-yl)-5-oxo-2-phenylpyrrolidin-3-yl)propanamide

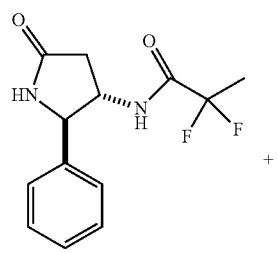

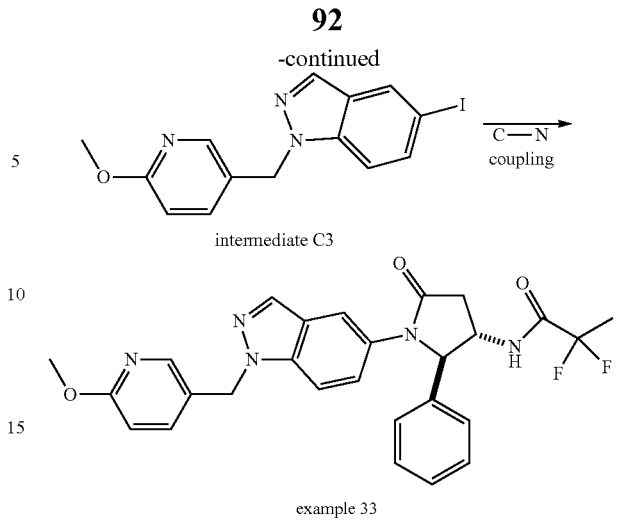

Starting from intermediate C3 and trans-2,2-difluoro-N-(5-oxo-2-phenylpyrrolidin-3-yl)propanamide, example 33 was synthesized in analogy to the synthetic procedure described for example 31.

$^1$H NMR (DMSO-$d_6$) δ: 9.45-9.47 (m, 1H), 8.15-8.16 (m, 1H), 8.01 (s, 1H), 7.72-7.73 (m, 1H), 7.67-7.69 (m, 1H), 7.48-7.55 (m, 2H), 7.27-7.33 (m, 4H), 7.20-7.22 (m, 1H), 6.70-6.72 (m, 1H), 5.52 (s, 2H), 5.25-5.26 (m, 1H), 4.23-4.25 (m, 1H), 3.77 (m, 3H), 3.03-3.10 (m, 1H), 2.57-2.62 (m, 1H), 1.72-1.82 (m, 3H).

EXAMPLE 34 trans-2,2-difluoro-N-(1-(1-((1-methyl-6-oxo-1,6-dihydropyridin-3-yl)methyl)-1H-indazol-5-yl)-5-oxo-2-phenylpyrrolidin-3-yl)propanamide

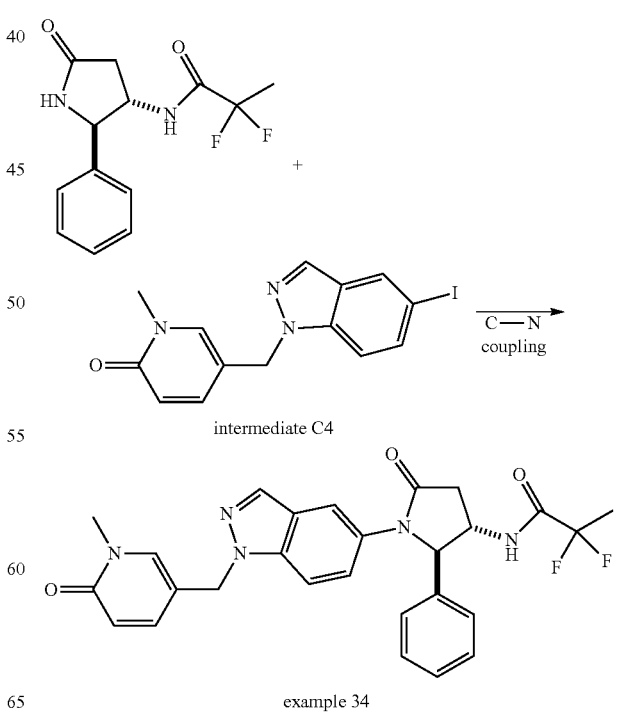

Starting from intermediate C4 and trans-2,2-difluoro-N-(5-oxo-2-phenylpyrrolidin-3-yl)propanamide, example 34 was synthesized in analogy to the synthetic procedure described for example 31.

$^1$H NMR (DMSO-d$_6$) δ: 9.45-9.47 (m, 1H), 8.00 (s, 1H), 7.83 (s, 1H), 7.73 (s, 1H), 7.68-7.71 (m, 1H), 7.49-7.51 (m, 1H), 7.21-7.34 (m, 6H), 6.29 (d, 1H), 5.25-5.28 (m, 3H), 4.28-4.22 (m, 1H), 3.37 (s, 3H), 3.03-3.10 (m, 1H), 2.61-2.62 (m, 1H), 1.73-1.82 (m, 3H).

EXAMPLE 35 trans-2,2-difluoro-N-(1-(1-(1-(cyclopropanecarbonyl)piperidin-4-yl)-1H-indazol-5-yl)-5-oxo-2-phenylpyrrolidin-3-yl)propanamide

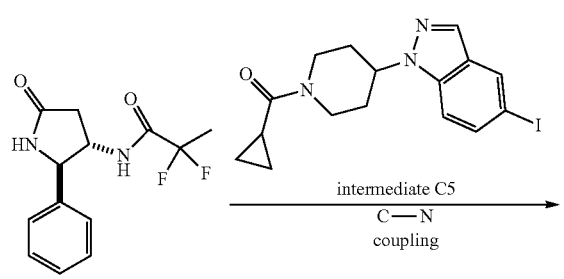

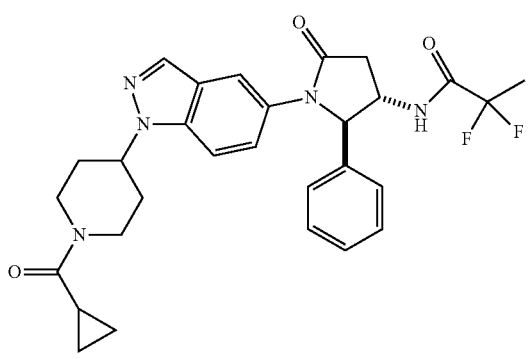

example 35

Starting from intermediate C5 and trans-2,2-difluoro-N-(5-oxo-2-phenylpyrrolidin-3-yl)propanamide, example 35 was synthesized in analogy to the synthetic procedure described for example 31.

$^1$H NMR (DMSO-d$_6$) δ: 9.47-9.45 (m, 1H), 8.00 (s, 1H), 7.72-7.71 (m, 1H), 7.66-7.64 (m, 1H), 7.52-7.50 (m, 1H), 7.35-7.28 (m, 4H), 7.23-7.21 (m, 1H), 5.28-5.26 (m, 1H), 4.88-4.83 (m, 1H), 4.61-4.56 (m, 2H), 4.27-4.25 (m, 1H), 3.11-3.05 (m, 1H), 2.95-2.93 (m, 1H), 2.63-2.58 (m, 1H), 2.02-1.97 (m, 5H), 1.83-1.73 (m, 4H), 0.73-0.69 (m, 4H).

EXAMPLE 38 trans-2,2-difluoro-N-(1-(1-((1-methyl-2-oxo-1,2-dihydropyridin-4-yl)methyl)-1H-indazol-5-yl)-5-oxo-2-phenylpyrrolidin-3-yl)propanamide

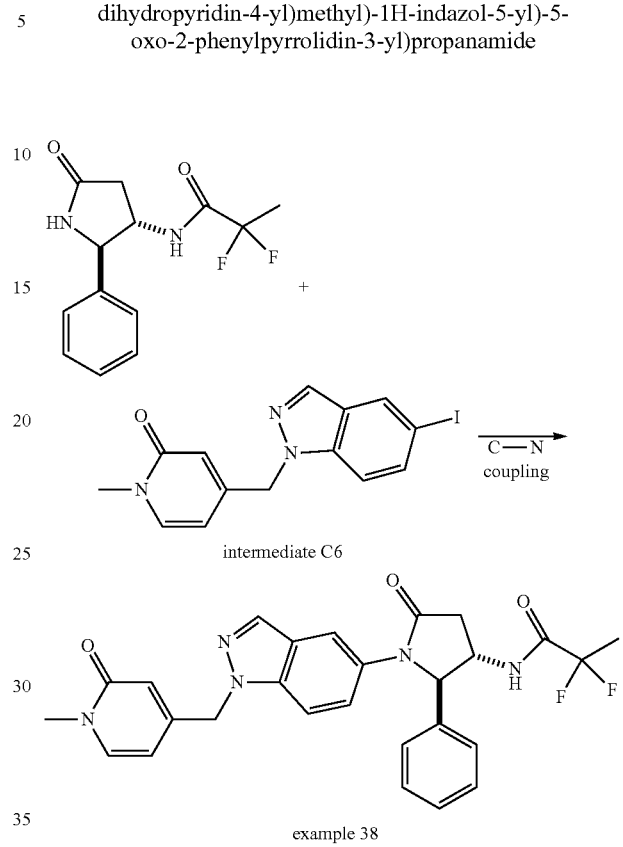

example 38

Starting from intermediate C6 and trans-2,2-difluoro-N-(5-oxo-2-phenylpyrrolidin-3-yl)propanamide, example 38 was synthesized in analogy to the synthetic procedure described for example 31.

$^1$H NMR (DMSO-d$_6$) δ: 9.47-9.45 (m, 1H), 8.07 (s, 1H), 7.76 (s, 1H), 7.58-7.49 (m, 3H), 7.34-7.28 (m, 4H), 7.23-7.21 (m, 1H), 5.96 (s, 1H), 5.90-5.88 (m, 1H), 5.43 (s, 2H), 5.28-5.26 (m, 1H), 4.26-4.24 (m, 1H), 3.10-3.04 (m, 1H), 2.62-2.57 (m, 1H), 1.82-1.73 (m, 3H).

EXAMPLE 39

N-((2R,3S)-2-(2-fluorophenyl)-1-(1-(1-methyl-6-oxo-1,6-dihydropyridin-3-yl)-1H-indazol-5-yl)-5-oxopyrrolidin-3-yl)cyclopropanecarboxamide

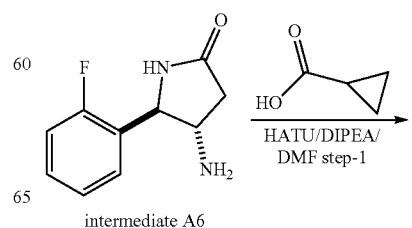

intermediate A6

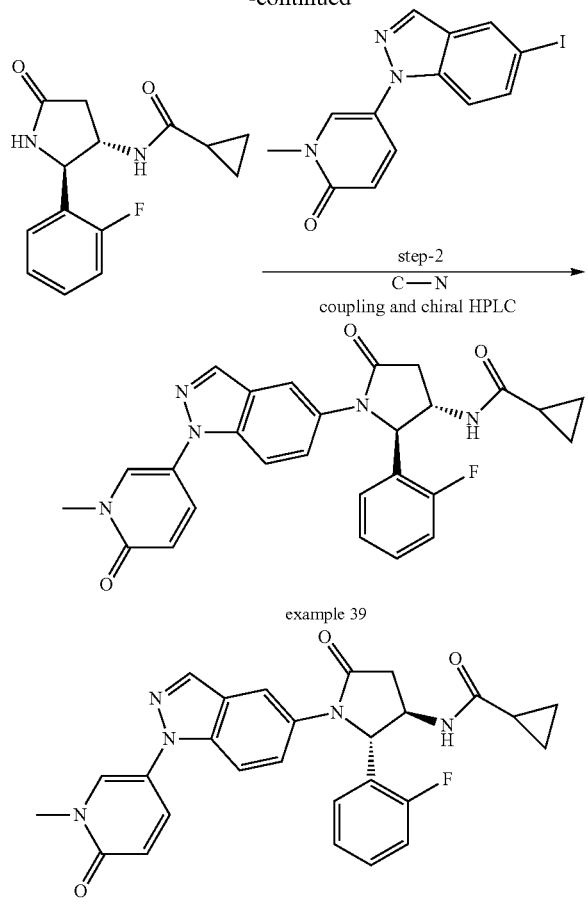

example 39

Step 1: To a stirred solution of cyclopropanecarboxylic acid (0.53 g, 6.18 mmol, 1.2 eq) in DMF (8 mL), HATU (4.00 g, 10.30 mmol, 2.0 eq), DIPEA (4.5 mL, 25.75 mmol, 5.0 eq) and intermediate A6 (1.00 g, 5.15 mmol, 1.0 eq) were added at 0° C. and the reaction was stirred at RT for 16 h. After completion of the reaction (monitored by TLC, TLC system 5% methanol in DCM, Rf-0.3), the reaction mixture was diluted with EtOAc (25 mL), washed with ice cold water (3×25 mL), dried over $Na_2SO_4$ and concentrated under reduced pressure to get the crude product which was purified by column chromatography (230-400 mesh silica gel; 0 to 2% MeOH-DCM;) to afford trans-N-(2-(2-fluorophenyl)-5-oxopyrrolidin-3-yl)cyclopropanecarboxamide (0.56 g, 41%).

Step 2: A stirred solution of trans-N-(2-(2-fluorophenyl)-5-oxopyrrolidin-3-yl)cyclopropanecarboxamide (0.250 g, 0.953 mmol, 1 eq), 5-(5-iodo-1H-indazol-1-yl)-1-methylpyridin-2(1H)-one (0.401 g, 1.144 mmol, 1.2 eq) and $K_3PO_4$ (0.404 g, 1.906 mmol, 2.0 eq) in 1,4-dioxane (10 mL) was degassed with argon for 30 min. Then, trans-N,N'-dimethylcyclohexane-1,2-diamine (0.054 g, 0.381 mmol, 0.4 eq) and CuI (0.036 g, 0.191 mmol, 0.2 eq) were added and the reaction was stirred for 16 h at 90° C. in a sealed tube. After completion of the reaction (monitored by TLC, TLC system 5% methanol in DCM, Rf-0.4), the reaction mixture was filtered through a celite bed and the celite bed was washed 2-3 times with 1,4-dioxane. The combined organic layers were concentrated under reduced pressure to get the crude product which was purified by column chromatography (230-400 mesh silica gel; 0 to 2% MeOH in DCM) to afford the racemic product. Further enantiomer separation was done by preparative chiral HPLC to afford N-((2S,3R)-2-(2-fluorophenyl)-1-(1-(1-methyl-6-oxo-1,6-dihydropyridin-3-yl)-1H-indazol-5-yl)-5-oxopyrrolidin-3-yl)cyclopropanecarboxamide (0.042 g, 9%; RT=6.96 min, Column Name: Chiralpak IA (250×4.6 mm) 5 μm, Mobile Phase: Hexane/EA/EtOH/DEA: 50/25/25/0.1, Flow Rate: 1.0 ml/min) and N-((2R,3S)-2-(2-fluorophenyl)-1-(1-(1-methyl-6-oxo-1,6-dihydropyridin-3-yl)-1H-indazol-5-yl)-5-oxopyrrolidin-3-yl)cyclopropanecarboxamide (0.042 g, 9%; RT=9.77 min, Column Name: Chiralpak IA (250×4.6 mm) 5 μm, Mobile Phase: Hexane/EA/EtOH/DEA: 50/25/25/0.1, Flow Rate: 1.0 ml/min).

$^1$H NMR (DMSO-$d_6$) δ: 8.86-8.85 (m, 1H), 8.27 (s, 1H), 8.19 (s, 1H), 7.81 (s, 1H), 7.71-7.69 (m, 1H), 7.62-7.60 (m, 1H), 7.52-7.49 (m, 1H), 7.39-7.35 (m, 1H), 7.25 (s, 1H), 7.15-7.09 (m, 2H), 6.54-6.52 (m, 1H), 5.44-5.43 (m, 1H), 4.36-4.31 (m, 1H), 3.49 (s, 3H), 3.13-3.06 (m, 1H), 1.58-1.55 (m, 1H), 0.68 (s, 4H).

EXAMPLE 40 trans-N-(1-(1-((2-methoxypyridin-4-yl)methyl)-1H-indazol-5-yl)-5-oxo-2-phenylpyrrolidin-3-yl)cyclopropanecarboxamide

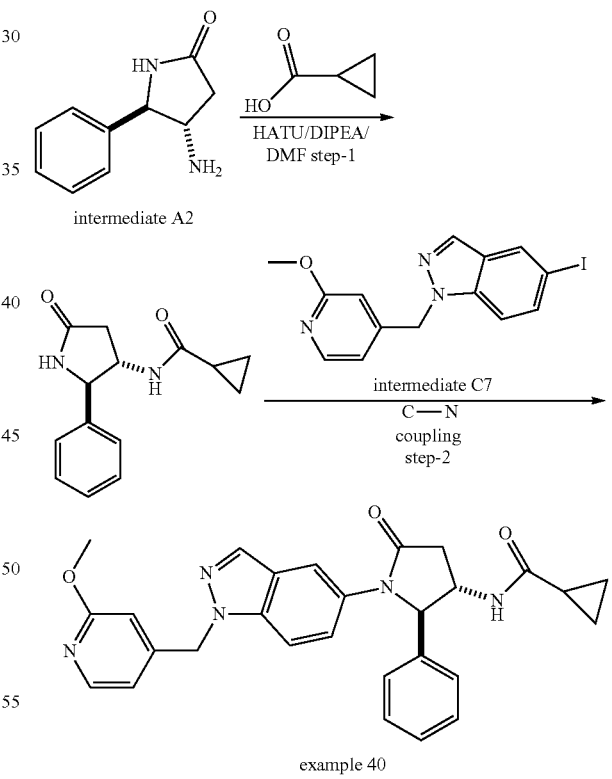

example 40

Step 1: To a stirred solution of cyclopropanecarboxylic acid (2.35 g, 27.27 mmol, 1.2 eq) in DMF (40 mL), HATU (17.22 g, 45.45 mmol, 2.0 eq), DIPEA (19.75 mL, 113.64 mmol, 5.0 eq) and intermediate A2 (4.00 g, 22.73 mmol, 1.0 eq) were added at 0° C. and the reaction mixture was then stirred at RT for 16 h. After completion of the reaction (monitored by TLC, TLC system 5% methanol in DCM, Rf-0.3), the reaction mixture was diluted with EtOAc (250 mL), washed with ice cold water (3×150 mL), dried over Na₂SO₄ and concentrated under reduced pressure to get the crude product which was purified by column chromatography (230-400 mesh silica gel; 0 to 3% MeOH-DCM) to afford trans-N-(5-oxo-2-phenylpyrrolidin-3-yl)cyclopropanecarboxamide (2.1 g, 39%).

Step 2: Starting from intermediate C7 and trans-N-(5-oxo-2-phenylpyrrolidin-3-yl)cyclopropanecarboxamide, example 40 was synthesized in analogy to the synthetic procedure described for example 31.

$^1$H NMR (DMSO-$d_6$) δ: 8.87-8.88 (m, 1H), 8.02-8.08 (m, 2H), 7.79 (s, 1H), 7.57-7.60 (m, 2H), 7.22-7.32 (m, 5H), 6.65-6.66 (m, 1H), 6.45 (s, 1H), 5.60 (s, 2H), 5.21-5.19 (m, 1H), 4.15-4.08 (m, 1H), 3.77 (s, 3H), 3.00-3.06 (m, 1H), 2.32-2.44 (m, 1H), 1.59 (s, 1H), 0.69-0.72 (m, 4H).

EXAMPLE 41

N-((2R,3S)-1-(1-(1-methyl-6-oxo-1,6-dihydropyridin-3-yl)-1H-indazol-5-yl)-5-oxo-2-(o-tolyl)pyrrolidin-3-yl)cyclopropanecarboxamide

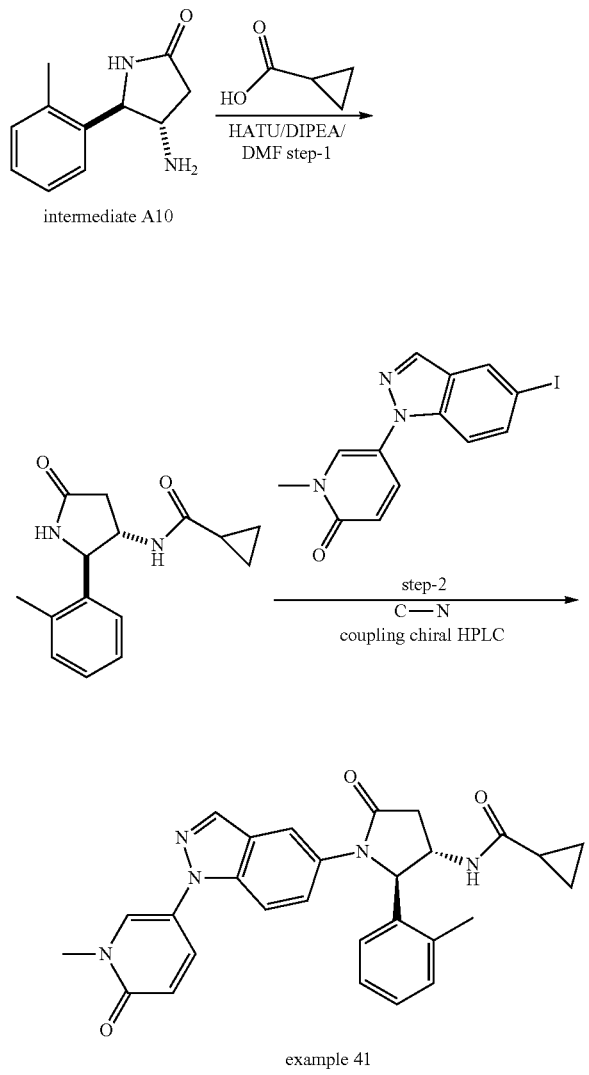

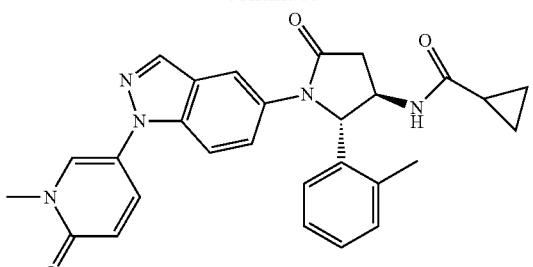

Step 1: To a stirred solution of cyclopropanecarboxylic acid (0.54 g, 6.31 mmol, 1.2 eq) in DMF (8.0 mL), HATU (3.90 g, 10.52 mmol, 2.0 eq), DIPEA (4.7 mL, 26.32 mmol, 5.0 eq) and intermediate A10 (1.00 g, 5.26 mmol, 1.0 eq) were added at 0° C. and the reaction mixture was then stirred at RT for 16 h. After completion of the reaction (monitored by TLC, TLC system 5% MeOH in DCM, Rf-0.3), the reaction mixture was diluted with EtOAc (25 mL), washed with ice cold water (3×25 mL), dried over Na₂SO₄ and concentrated under reduced pressure to get the crude product which was purified by column chromatography (230-400 mesh silica gel; 0 to 2% MeOH-DCM) to afford trans-N-(5-oxo-2-(o-tolyl)pyrrolidin-3-yl)cyclopropanecarboxamide (0.60 g, 43%).

Step 2: A stirred solution of trans-N-(5-oxo-2-(o-tolyl)pyrrolidin-3-yl)cyclopropanecarboxamide (0.40 g, 1.55 mmol, 1.0 eq), 5-(5-iodo-1H-indazol-1-yl)-1-methylpyridin-2(1H)-one (0.65 g, 1.86 mmol, 1.2 eq) and K₃PO₄ (0.66 g, 3.10 mmol, 2.0 eq) in 1,4-dioxane (10 mL) was degassed with argon for 30 min. Then, trans-N,N'-dimethylcyclohexane-1,2-diamine (0.09 g, 0.62 mmol, 0.4 eq) and CuI (0.06 g, 0.31 mmol, 0.2 eq) were added and the reaction mixture was stirred for 16 h at 90° C. in a sealed tube. After completion of the reaction (monitored by TLC, TLC system 5% MeOH in DCM, Rf-0.4), the reaction mixture was filtered through a celite bed and the celite bed was washed 2-3 times with 1,4-dioxane. The combined organic layers were concentrated to get the crude product which was purified by column chromatography (230-400 mesh silica gel; 0 to 2% MeOH in DCM) to afford the racemic product. Further enantiomer separation was done by preparative chiral HPLC to afford N-((2S,3R)-1-(1-(1-methyl-6-oxo-1,6-dihydropyridin-3-yl)-1H-indazol-5-yl)-5-oxo-2-(o-tolyl)pyrrolidin-3-yl)cyclopropanecarboxamide (0.14 g, 19%; RT=6.72 min, Column Name: Chiralpak IA (250×4.6 mm) 5 μm, Mobile Phase: Hexane/EA/EtOH/DEA: 50/25/25/0.1, Flow Rate: 1.0 ml/min) and N-((2R,3S)-1-(1-(1-methyl-6-oxo-1,6-dihydropyridin-3-yl)-1H-indazol-5-yl)-5-oxo-2-(o-tolyl)pyrrolidin-3-yl)cyclopropanecarboxamide (0.10 g, 14%; RT=8.13 min, Column Name: Chiralpak IA (250×4.6 mm) 5 μm, Mobile Phase: Hexane/EA/EtOH/DEA: 50/25/25/0.1, Flow Rate: 1.0 ml/min).

$^1$H NMR (DMSO-$d_6$) δ: 9.00-8.99 (m, 1H), 8.26 (s, 1H), 8.18 (s, 1H), 7.91 (s, 1H), 7.72-7.70 (m, 1H), 7.61 (s, 2H), 7.16-7.11 (m, 4H), 6.54 (d, 1H), 5.41-5.40 (m, 1H), 4.18-4.16 (m, 1H), 3.49 (s, 3H), 3.10-3.03 (m, 1H), 2.43-2.41 (m, 4H), 1.61-1.60 (m, 1H), 0.71-0.69 (m, 4H).

EXAMPLE 42

2,2-difluoro-N-((2R,3S)-2-(2-methoxypyridin-4-yl)-1-(1-(1-methyl-6-oxo-1,6-dihydropyridin-3-yl)-1H-indazol-5-yl)-5-oxopyrrolidin-3-yl)propanamide

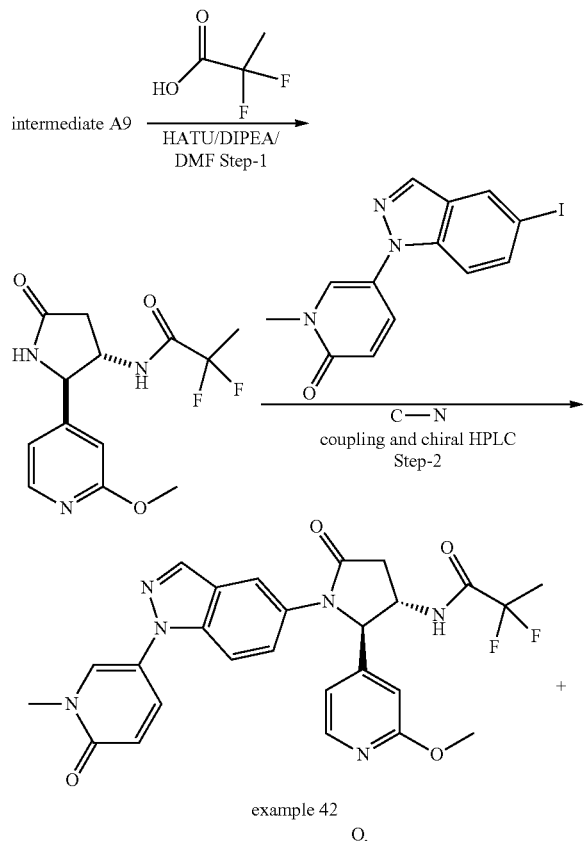

example 42

Step 1: To a stirred solution of 2,2-difluoropropanoic acid (0.64 g, 5.79 mmol, 1.2 eq) in DMF (10 mL), HATU (3.60 g, 9.65 mmol, 2.0 eq), DIPEA (4.2 mL, 24.13 mmol, 5.0 eq) and intermediate A9 (1.00 g, 4.83 mmol, 1.0 eq) were added at 0° C. and the reaction mixture was stirred at RT for 16 h. After completion of the reaction, (monitored by TLC, TLC system 5% MeOH in DCM, Rf-0.3), the reaction mixture was diluted with EtOAc (25 mL), washed with ice cold water (3×25 mL), dried over $Na_2SO_4$ and concentrated under reduced pressure to get the crude product which was purified by column chromatography (230-400 mesh silica gel; 0 to 2% MeOH-DCM;) to afford trans-2,2-difluoro-N-(2-(2-methoxypyridin-4-yl)-5-oxopyrrolidin-3-yl)propanamide (0.76 g, 52%).

Step 2: A stirred solution of trans-2,2-difluoro-N-(5-oxo-2-(2-methoxypyridin-4-yl)pyrrolidin-3-yl)propanamide (0.378 g, 1.26 mmol, 1.0 eq), 5-(5-iodo-1H-indazol-1-yl)-1-methylpyridin-2(1H)-one (0.531 g, 1.52 mmol, 1.2 eq) and $K_3PO_4$ (0.370 g, 2.53 mmol, 2.0 eq) in 1,4-dioxane (10 mL) was degassed with argon for 30 min. Then, trans-N,N'-dimethylcyclohexane-1,2-diamine (0.072 g, 0.51 mmol, 0.4 eq) and CuI (0.048 g, 0.25 mmol, 0.2 eq) were added and the reaction was stirred for 16 h at 90° C. in a sealed tube. After completion of the reaction (monitored by TLC, TLC system 5% methanol in DCM, Rf-0.4), the reaction mixture was filtered through a celite bed and the celite bed was washed 2-3 times with 1,4-dioxane. The combined organic layers were concentrated to get the crude product which was purified by column chromatography (230-400 mesh silica gel; 0 to 7% MeOH in DCM) to afford the racemic trans-2,2-difluoro-N-(2-(2-methoxypyridin-4-yl)-1-(1-(1-methyl-6-oxo-1,6-dihydropyridin-3-yl)-1H-indazol-5-yl)-5-oxopyrrolidin-3-yl)propanamide. Further enantiomer separation was done by preparative chiral HPLC to afford pure 2,2-difluoro-N-((2S,3R)-2-(2-methoxypyridin-4-yl)-1-(1-(1-methyl-6-oxo-1,6-dihydropyridin-3-yl)-1H-indazol-5-yl)-5-oxopyrrolidin-3-yl)propanamide (0.035 g, 5%; RT=11.93 min, Column Name: Chiralpak IA (250×4.6 mm) 5 μm, Mobile Phase: Hexane/EA/EtOH/DEA: 70/15/15/0.1, Flow Rate: 1.0 ml/min) and 2,2-difluoro-N-((2R,3S)-2-(2-methoxypyridin-4-yl)-1-(1-(1-methyl-6-oxo-1,6-dihydropyridin-3-yl)-1H-indazol-5-yl)-5-oxopyrrolidin-3-yl)propanamide (0.027 g, 4%; RT=14.72 min, Column Name: Chiralpak IA (250×4.6 mm) 5 μm, Mobile Phase: Hexane/EA/EtOH/DEA: 70/15/15/0.1, Flow Rate: 1.0 ml/min).

$^1$H NMR (DMSO-$d_6$) δ: 9.48-9.46 (m, 1H), 8.26 (s, 1H), 8.20 (d, 1H), 8.09 (d, 1H), 7.87 (s, 1H), 7.73-7.70 (m, 1H), 7.63-7.60 (m, 2H), 7.00-6.98 (m, 1H), 6.75 (s, 1H), 6.54-6.52 (m, 1H), 5.32-5.31 (m, 1H), 4.31-4.29 (m, 1H), 3.77 (s, 3H), 3.49 (s, 3H), 3.13-3.06 (m, 1H), 2.68-2.62 (m, 1H), 1.83-1.74 (m, 3H).

EXAMPLE 43

2,2-difluoro-N-((2R,3S)-1-(1-(1-methyl-6-oxo-1,6-dihydropyridin-3-yl)-1H-indazol-5-yl)-5-oxo-2-(o-tolyl)pyrrolidin-3-yl)propanamide

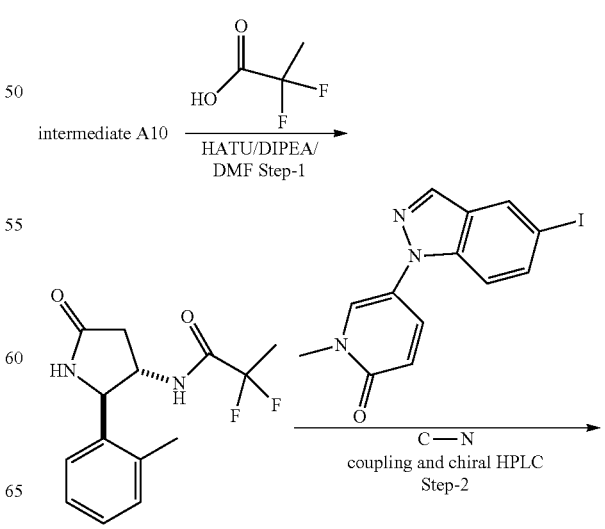

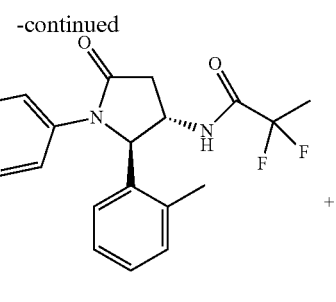

example 43

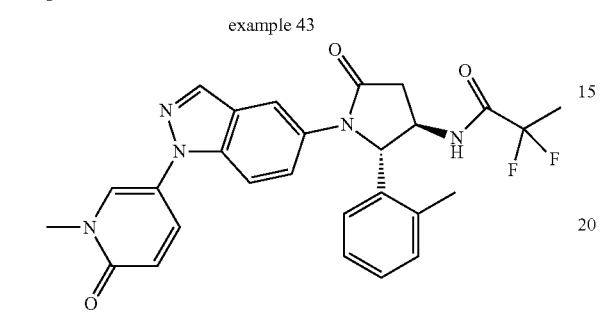

Step 1: To a stirred solution of 2,2-difluoropropanoic acid (0.70 g, 6.32 mmol, 1.2 eq) in DMF (8 mL), HATU (3.90 g, 10.52 mmol, 2.0 eq), DIPEA (4.7 mL, 26.32 mmol, 5.0 eq) and intermediate A10 (1.00 g, 5.26 mmol, 1.0 eq) were added at 0° C. and the reaction was then stirred at RT for 16 h. After completion of the reaction (monitored by TLC, TLC system 5% MeOH in DCM, Rf-0.3), the reaction mixture was diluted with EtOAc (25 mL), washed with ice cold water (3×25 mL), dried over Na$_2$SO$_4$ and concentrated under reduced pressure to get the crude product which was purified by column chromatography (230-400 mesh silica gel; 0 to 2% MeOH-DCM) to afford trans-2,2-difluoro-N-(5-oxo-2-(o-tolyl)pyrrolidin-3-yl)propanamide (0.60 g, 40%).

Step 2: A stirred solution of trans-2,2-difluoro-N-(5-oxo-2-(o-tolyl)pyrrolidin-3-yl)propanamide (0.25 g, 0.873 mmol, 1 eq), 5-(5-iodo-1H-indazol-1-yl)-1-methylpyridin-2 (1H)-one (0.37 g, 1.04 mmol, 1.2 eq) and K$_3$PO$_4$ (0.37 g, 1.746 mmol, 2.0 eq) in 1,4-dioxane (10 mL) was degassed with argon for 30 min. Then, trans-N,N'-dimethylcyclohexane-1,2-diamine (0.050 g, 0.35 mmol, 0.4 eq) and CuI (0.033 g, 0.175 mmol, 0.2 eq) were added and the reaction was stirred for 16 h at 90° C. in a sealed tube. After completion of the reaction (monitored by TLC, TLC system 5% MeOH in DCM, Rf-0.4), the reaction mixture was filtered through a celite bed and the celite bed was washed 2-3 times with 1,4-dioxane. The combined organic layers were concentrated to get the crude product which was purified by column chromatography (230-400 mesh silica gel; 0 to 2% MeOH in DCM) to afford the racemic trans-2,2-difluoro-N-(1-(1-(1-methyl-6-oxo-1,6-dihydropyridin-3-yl)-1H-indazol-5-yl)-5-oxo-2-(o-tolyl)pyrrolidin-3-yl)propanamide. Further enantiomer separation was done by preparative chiral HPLC to afford 2,2-difluoro-N-((2S,3R)-1-(1-(1-methyl-6-oxo-1,6-dihydropyridin-3-yl)-1H-indazol-5-yl)-5-oxo-2-(o-tolyl)pyrrolidin-3-yl)propanamide (0.08 g, 17%; RT=5.57 min, Column Name: Chiralpak IA (250×4.6 mm) 5 μm, Mobile Phase: Hexane/EA/EtOH/DEA: 50/25/25/0.1, Flow Rate: 1.0 ml/min) and 2,2-difluoro-N-((2R, 3S)-1-(1-(1-methyl-6-oxo-1,6-dihydropyridin-3-yl)-1H-indazol-5-yl)-5-oxo-2-(o-tolyl)pyrrolidin-3-yl)propanamide (0.07 g, 15%; RT=7.91 min, Column Name: Chiralpak IA (250×4.6 mm) 5 μm, Mobile Phase: Hexane/EA/EtOH/DEA: 50/25/25/0.1, Flow Rate: 1.0 ml/min).

$^1$H NMR (DMSO-d$_6$) δ: 9.61-9.60 (m, 1H), 8.26 (s, 1H), 8.18 (s, 1H), 7.86 (s, 1H), 7.71-7.69 (m, 1H), 7.62-7.55 (m, 2H), 7.15-7.12 (m, 4H), 6.54-6.51 (m, 1H), 5.54-5.52 (m, 1H), 4.30-4.24 (m, 1H), 3.49 (s, 3H), 3.16-3.09 (m, 1H), 2.58-2.54 (m, 1H), 2.37 (s, 3H), 1.83-1.73 (m, 3H).

EXAMPLE 46

N-(trans-1-(1-(1-methyl-1H-pyrazol-4-yl)-1H-indazol-5-yl)-5-oxo-2-phenylpyrrolidin-3-yl)-2,2-difluoropropanamide

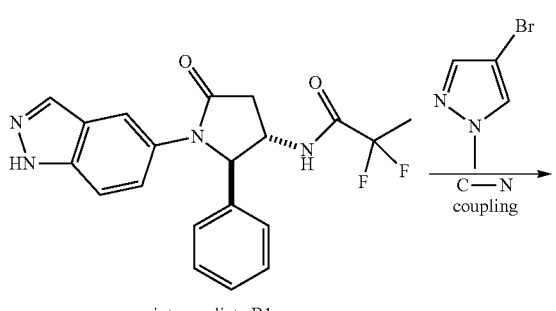

intermediate B1

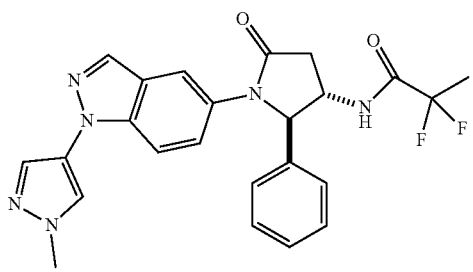

example 46

Intermediate B1 (80.0 mg, 0.208 mmol, 1.0 eq), copper iodide (7.9 mg, 0.042 mmol, 0.2 eq), sodium iodide (93.6 mg, 0.624 mmol, 3.0 eq), 4-bromo-1-methylpyrazole (67.0 mg, 0.416 mmol, 2.0 eq) and K$_3$PO$_4$ (132.5 mg, 0.624 mmol, 3.0 eq) are weighed out into a vial, a stir bar was added, the vial was sealed and was purged with nitrogen. 1,4-Dioxane (1.5 mL) was added, followed by trans-N,N-dimethylcyclohexane-1,2-diamine (0.012 g, 0.083 mmol, 0.4 eq). The mixture was heated to 110° C. for 16 hours. The mixture was cooled to RT and was then diluted with DCM and water. The mixture was filtered through a hydrophobic frit and was then purified via column chromatography to afford N-(trans-1-(1-(1-methyl-1H-pyrazol-4-yl)-1H-indazol-5-yl)-5-oxo-2-phenylpyrrolidin-3-yl)-2,2-difluoropropanamide (73.4 mg, 76%).

¹H NMR (DMSO-d₆) δ: 9.48 (d, 1H), 8.24 (s, 1H), 8.20 (d, 1H), 7.84 (d, 1H), 7.82 (d, 1H), 7.64-7.56 (m, 2H), 7.35 (d, 2H), 7.31 (t, 2H), 7.24-7.20 (m, 1H), 5.30 (d, 1H), 4.34-4.24 (m, 1H), 3.90 (s, 3H), 3.12-3.07 (m, 1H), 2.63 (dd, 1H), 1.78 (t, 3H).

EXAMPLE 47

N-(trans-1-(1-(5-fluoropyrimidin-2-yl)-1H-indazol-5-yl)-5-oxo-2-phenylpyrrolidin-3-yl)-2,2-difluoropropanamide

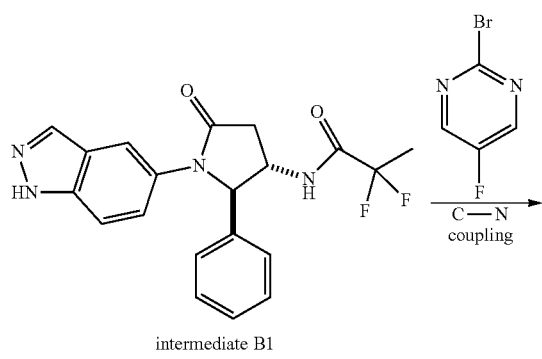

intermediate B1

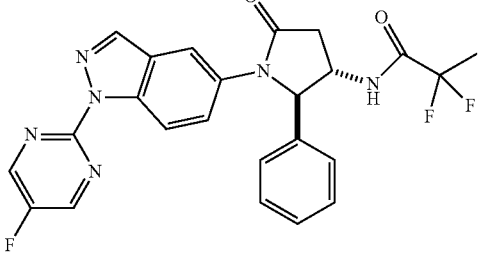

example 47

Starting from intermediate B1, example 47 was synthesized in analogy to the synthetic procedure described for example 46, substituting 4-bromo-1-methylpyrazole for 2-bromo-5-fluoropyrimidine and prolonging the reaction time to 40 hours. Example 47 was obtained in 57% yield (57.1 mg).

¹H NMR (DMSO-d₆) δ: 9.49 (d, 1H), 8.97 (s, 2H), 8.45 (dt, 1H), 8.42 (d, 1H), 7.95 (d, 1H), 7.72 (dd, 1H), 7.36 (dd, 2H), 7.31 (t, 2H), 7.25-7.20 (m, 1H), 5.36 (d, 1H), 4.40-4.24 (m, 1H), 3.12 (dd, 1H), 2.66 (dd, 1H), 1.77 (t, 3H).

The examples in Table 1 were synthesized in analogy to Example 13.

| Ex. # | Intermediate | Structure | Yield (%) | ¹H NMR |
|---|---|---|---|---|
| 44 | intermediate D1-ent2 | 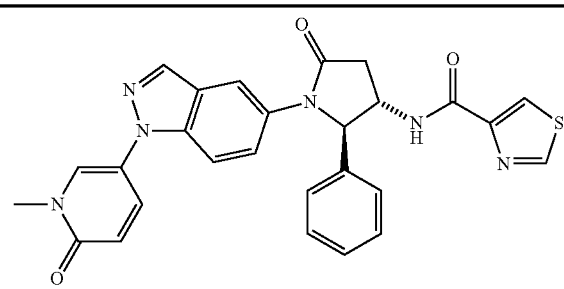 | 100 | ¹H NMR (DMSO-d₆) δ: 9.26 (d, 1H), 9.21 (dd, 1H), 8.35 (dd, 1H), 8.24 (d, 1H), 8.16 (d, 1H), 7.83 (dd, 1H), 7.71 (dd, 1H), 7.61-7.53 (m, 2H), 7.41-7.36 (m, 2H), 7.29 (t, 2H), 7.24-7.17 (m, 1H), 6.54 (d, 1H), 5.46 (d, 1H), 4.56-4.48 (m, 1H), 3.50 (s, 3H), 3.09 (dd, 1H), 2.81-2.71 (m, 1H) |
| 45 | intermediate D1-ent2 | 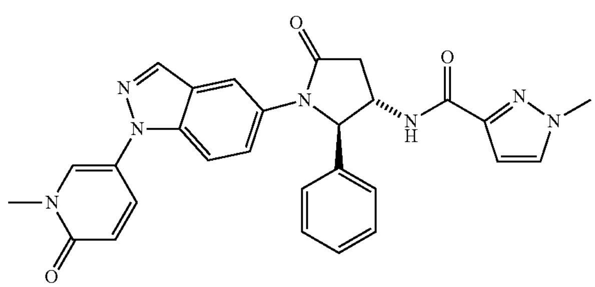 | 67 | ¹H NMR (DMSO-d₆) δ: 8.88 (d, 1H), 8.24 (d, 1H), 8.17 (d, 1H), 7.83 (dd, 1H), 7.78 (d, 1H), 7.71 (dd, 1H), 7.62-7.53 (m, 2H), 7.41-7.35 (m, 2H), 7.29 (t, 2H), 7.24-7.18 (m, 1H), 6.64 (d, 1H), 6.54 (d, 1H), 5.42 (d, 1H), 4.51-4.43 (m, 1H), 3.93 (s, 3H), 3.50 (s, 3H), 3.06 (dd, 1H), 2.73 (dd, 1H) |
| 48 | intermediate D1-ent2 | 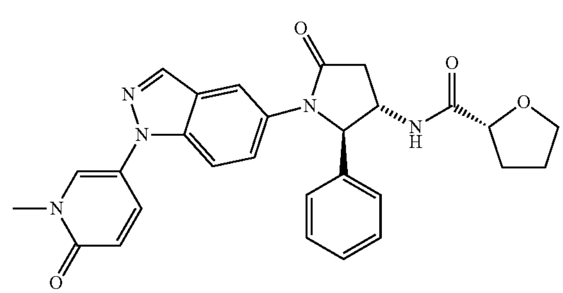 [SMILES: Cn1cc(-n2ncc3cc(N4C(=O)C[C@H](NC(=O)[C@H]5CCCO5)[C@H]4c4ccccc4)ccc32)ccc1=O] | 93 | ¹H NMR (DMSO-d₆) δ: 8.53 (d, 1H), 8.24 (d, 1H), 8.17 (d, 1H), 7.80 (dd, 1H), 7.70 (dd, 1H), 7.59 (dt, 1H), 7.52 (dd, 1H), 7.35-7.31 (m, 2H), 7.28 (dd, 2H), 7.24-7.17 (m, 1H), 6.54 (d, 1H), 5.27 (d, 1H), 4.31-4.26 (m, 1H), 4.24 (dd, 1H), 4.01-3.92 (m, 1H), 3.84-3.77 (m, 1H), 3.50 (s, 3H), 2.99 (dd, 1H), 2.62 (dd, 1H), 2.16-2.06 (m, 1H), 1.88-1.75 (m, 3H) |

| Ex. # | Intermediate | Structure | Yield (%) | 1H NMR |
|---|---|---|---|---|
| 49 | intermediate D1-ent2 | 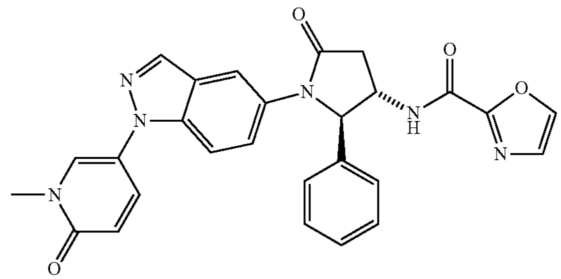 [SMILES: Cn1cc(-n2ncc3cc(N4C(=O)C[C@H](NC(=O)c5ncco5)[C@H]4c4ccccc4)ccc32)ccc1=O] | 39 | 1H NMR (DMSO-d6) δ: 9.74 (d, 1H), 8.33 (d, 1H), 8.24 (s, 1H), 8.17 (d, 1H), 7.86 (t, 1H), 7.71 (dd, 1H), 7.58 (d, 2H), 7.49 (d, 1H), 7.41-7.35 (m, 2H), 7.31 (t, 2H), 7.26-7.19 (m, 1H), 6.54 (d, 1H), 5.44 (d, 1H), 4.50-4.42 (m, 1H), 3.50 (s, 3H), 3.11 (dd, 1H), 2.75 (dd, 1H) |
| 50 | intermediate D1-ent2 | 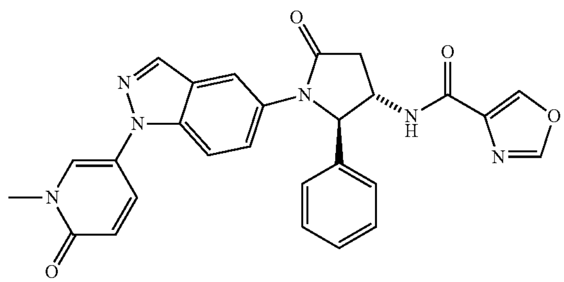 [SMILES: Cn1cc(-n2ncc3cc(N4C(=O)C[C@H](NC(=O)c5cocn5)[C@H]4c4ccccc4)ccc32)ccc1=O] | 76 | 1H NMR (DMSO-d6) δ: 9.11 (d, 1H), 8.65 (d, 1H), 8.55 (d, 1H), 8.24 (d, 1H), 8.17 (d, 1H), 7.84 (dd, 1H), 7.71 (dd, 1H), 7.62-7.53 (m, 2H), 7.41-7.35 (m, 2H), 7.30 (t, 2H), 7.21 (td, 1H), 6.54 (d, 1H), 5.43 (d, 1H), 4.53-4.44 (m, 1H), 3.50 (s, 3H), 3.08 (dd, 1H), 2.74 (dd, 1H) |
| 51 | intermediate D1-ent2 | 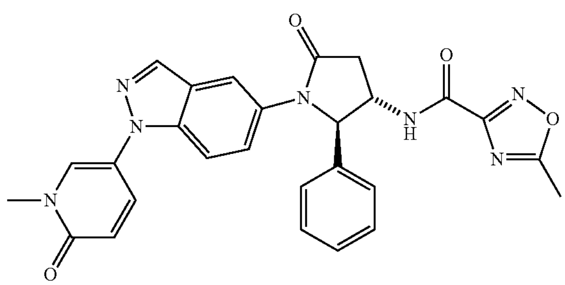 | 50 | 1H NMR (DMSO-d6) δ: 9.79 (d, 1H), 8.24 (s, 1H), 8.17 (d, 1H), 7.85 (dd, 1H), 7.71 (ddd, 1H), 7.62-7.54 (m, 2H), 7.41-7.33 (m, 2H), 7.31 (dd, 2H), 7.26-7.19 (m, 1H), 6.57-6.51 (m, 1H), 5.43 (d, 1H), 4.53-4.45 (m, 1H), 3.50 (s, 3H), 3.12 (dd, 1H), 2.72 (dd, 1H), 2.68 (s, 3H) |

Human Glucocorticoid Receptor (hGR) Ligand-Binding Assay

The human lymphoblast cell line IM9 (ATCC, Bethesda, Md.) were cultivated in RPMI 1640 media containing 10% fetal bovine serum, penicillin (100 U/ml), streptomycin (100 μg/ml), and 2 mM L-glutamine at 370 and 7% CO2 in a humidified incubator. Cells were centrifuged for 10 minutes at 1500 g and were washed in PBS and repelleted. Cell were then resuspended in homogenization buffer consisting of: 10 mM TES, 10 mM sodium molybdate, 1 mM EDTA, pH 7.4, 20 mM 2-mercaptoethanol, and 10% glycerol. Disruption of the cells was performed by nitrogen cavitation using 2×15 minutes at 600 to 750 psi nitrogen in a N2 cavitator at 0° C. The cell preparation was then centrifuged at 27,000 g for 15 minutes, and the resultant supernatant (=cytosol of IM9 cells) was centrifuged at 103,000 g for 60 minutes at 4° C. The amount of protein in the supernatant fraction was determined using a BCA assay kit and aliquots were snap frozen in a dry ice-acetone bath and stored at −70° C. Competitive binding assays were done in duplicate in homogenization buffer with a total volume of 200 μl. To this end, 1 mg of IM9 cytosol, 0.05 μCi (1.5 nM) of 3H-dexamethasone (1 μM) and compounds according to the present invention (=unlabeled competitors of dexamethasone; range of concentrations) were mixed. The reaction was stopped after incubation at 0° C. for 16 to 18 hours by the addition of 100 μl of a charcoal-dextran mixture (2% activated charcoal, 0.5% dextran in 10 mM Tris, 1 mM EDTA, pH 7.4). Another incubation step at 0° C. for 10 minutes followed before the samples were centrifuged for 5 minutes at 8200 g. 100 μl of the supernatant) was finally assayed for radioactivity by liquid scintillationspectrometry, and the IC50 values were determined graphically and were converted to Ki values.

The results are summarized in Table 2 below (% inhibition hGR at 1 μM; 40%<A<60%, 60%<B<85%, 85%<C).

TABLE 2

| EXAMPLE | % inhibition hGR at 1 μM |
|---|---|
| 1 | C |
| 2 | C |
| 3 | C |
| 4 | C |
| 5 | C |
| 6 | C |
| 7 | C |
| 9 | C |
| 13 | C |
| 15 | B |
| 17 | C |
| 18 | C |
| 22 | B |
| 23 | C |
| 24 | B |
| 25 | C |

TABLE 2-continued

| EXAMPLE | % inhibition hGR at 1 μM |
|---|---|
| 26 | B |
| 27 | B |
| 31 | C |
| 32 | B |
| 33 | C |
| 34 | A |
| 35 | B |
| 38 | B |
| 39 | B |
| 40 | A |
| 41 | A |
| 42 | B |
| 43 | C |
| 44 | B |
| 45 | B |
| 46 | C |
| 47 | B |
| 48 | B |
| 49 | C |
| 50 | B |
| 51 | C |

The invention claimed is:
1. A compound according to general formula (I),

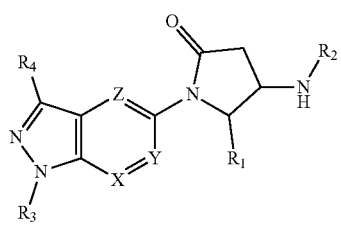

wherein
$R_1$ represents —$C_{1-10}$-alkyl; —$C_{3-10}$-cycloalkyl; —$C_{1-6}$-alkylene-$C_{3-10}$-cycloalkyl; 3 to 7 membered heterocycloalkyl; —$C_{1-6}$-alkylene-(3 to 7 membered heterocycloalkyl); aryl; —$C_{1-6}$-alkylene-aryl; 5 or 6-membered heteroaryl; or —$C_{1-6}$-alkylene-(5 or 6-membered heteroaryl);

$R_2$ represents —C(=O)—$C_{1-10}$-alkyl; —C(=O)—$C_{3-10}$-cycloalkyl; —C(=O)—$C_{1-6}$-alkylene-$C_{3-10}$-cycloalkyl; —C(=O)-(3 to 7 membered heterocycloalkyl); —C(=O)—$C_{1-6}$-alkylene-(3 to 7 membered heterocycloalkyl); —C(=O)-aryl; —C(=O)—$C_{1-6}$-alkylene-aryl; —C(=O)-(5 or 6-membered heteroaryl); —C(=O)—$C_{1-6}$-alkylene-(5 or 6-membered heteroaryl); —S(=O)$_{1-2}$—$C_{1-10}$-alkyl; —S(=O)$_{1-2}$—$C_{3-10}$-cycloalkyl; —S(=O)$_{1-2}$—$C_{1-6}$-alkylene-$C_{3-10}$-cycloalkyl; —S(=O)$_{1-2}$-(3 to 7 membered heterocycloalkyl); —S(=O)$_{1-2}$—$C_{1-6}$-alkylene-(3 to 7 membered heterocycloalkyl); —S(=O)$_{1-2}$-aryl; —S(=O)$_{1-2}$—$C_{1-6}$-alkylene-aryl; —S(=O)$_{1-2}$-(5 or 6-membered heteroaryl); or —S(=O)$_{1-2}$—$C_{1-6}$-alkylene-(5 or 6-membered heteroaryl);

$R_3$ represents 3 to 7 membered heterocycloalkyl; —$C_{1-6}$-alkylene-(3 to 7 membered heterocycloalkyl); 5 or 6-membered heteroaryl; —$C_{1-6}$-alkylene-(5 or 6-membered heteroaryl); —C(=O)-(3 to 7 membered heterocycloalkyl); —C(=O)—$C_{1-6}$-alkylene-(3 to 7 membered heterocycloalkyl); —C(=O)-(5 or 6-membered heteroaryl); —C(=O)—$C_{1-6}$-alkylene-(5 or 6-membered heteroaryl); —S(=O)$_{1-2}$-(3 to 7 membered heterocycloalkyl); —S(=O)$_{1-2}$—$C_{1-6}$-alkylene-(3 to 7 membered heterocycloalkyl); —S(=O)$_{1-2}$-(5 or 6-membered heteroaryl); or —S(=O)$_{1-2}$—$C_{1-6}$-alkylene-(5 or 6-membered heteroaryl);

$R_4$ represents —H; —F; —Cl; —Br; —I; —CN; —$CH_3$; —$CF_3$; —$CF_2H$; —$CFH_2$ or cyclopropyl;

X represents N or $CR_5$; wherein $R_5$ represents —H; —F; —Cl; —Br; —I; —CN; —$C_{1-10}$-alkyl or —$C_{3-10}$-cycloalkyl;

Y represents N or $CR_6$; wherein $R_6$ represents —H; —F; —Cl; —Br; —I; —CN; —$C_{1-10}$-alkyl or —$C_{3-10}$-cycloalkyl;

Z represents N or $CR_7$; wherein $R_7$ represents —H; —F; —Cl; —Br; —I; —CN; —$C_{1-10}$-alkyl or —$C_{3-10}$-cycloalkyl;

wherein —$C_{1-10}$-alkyl, —$C_{1-4}$-alkyl and —$C_{1-6}$-alkylene- in each case independently from one another is linear or branched, saturated or unsaturated;

wherein —$C_{1-10}$-alkyl, —$C_{1-4}$-alkyl, —$C_{1-6}$-alkylene-, —$C_{3-10}$-cycloalkyl and 3 to 7 membered heterocycloalkyl in each case independently from one another are unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —C(=O)—$C_{1-6}$-alkyl; —C(=O)—OH; —C(=O)—O$C_{1-6}$-alkyl; —C(=O)—$NH_2$; —C(=O)—NH($C_{1-6}$-alkyl); —C(=O)—N($C_{1-6}$-alkyl)$_2$; —OH; =O; —$OCF_3$; —$OCF_2H$; —$OCFH_2$; —$OCF_2Cl$; —$OCFCl_2$; —O—$C_{1-6}$-alkyl; —O—C(=O)—$C_{1-6}$-alkyl; —O—C(=O)—O—$C_{1-6}$-alkyl; —O—(CO)—NH($C_{1-6}$-alkyl); —O—C(=O)—N($C_{1-6}$-alkyl)$_2$; —O—S(=O)$_2$—$NH_2$; —O—S(=O)$_2$—NH($C_{1-6}$-alkyl); —O—S(=O)$_2$—N($C_{1-6}$-alkyl)$_2$; —$NH_2$; —NH($C_{1-6}$-alkyl); —N($C_{1-6}$-alkyl)$_2$; —NH—C(=O)—$C_{1-6}$-alkyl; —NH—C(=O)—O—$C_{1-6}$-alkyl; —NH—C(=O)—$NH_2$; —NH—C(=O)—NH($C_{1-6}$-alkyl); —NH—C(=O)—N($C_{1-6}$-alkyl)$_2$; —N($C_{1-6}$-alkyl)-C(=O)—$C_{1-6}$-alkyl; —N($C_{1-6}$-alkyl)-C(=O)—O—$C_{1-6}$-alkyl; —N($C_{1-6}$-alkyl)-C(=O)—$NH_2$; —N($C_{1-6}$-alkyl)-C(=O)—NH($C_{1-6}$-alkyl); —N($C_{1-6}$-alkyl)-C(=O)—N($C_{1-6}$-alkyl)$_2$; —NH—S(=O)$_2$OH; —NH—S(=O)$_2$—$C_{1-6}$-alkyl; —NH—S(=O)$_2$—O—$C_{1-6}$-alkyl; —NH—S(=O)$_2$—$NH_2$; —NH—S(=O)$_2$—NH($C_{1-6}$-alkyl); —NH—S(=O)$_2$N($C_{1-6}$-alkyl)$_2$; —N($C_{1-6}$-alkyl)-S(=O)$_2$—OH; —N($C_{1-6}$-alkyl)-S(=O)$_2$—$C_{1-6}$-alkyl; —N($C_{1-6}$-alkyl)-S(=O)$_2$—O—$C_{1-6}$-alkyl; —N($C_{1-6}$-alkyl)-S(=O)$_2$—$NH_2$; —N($C_{1-6}$-alkyl)-S(=O)$_2$—NH($C_{1-6}$-alkyl); —N($C_{1-6}$-alkyl)-S(=O)$_2$—N($C_{1-6}$-alkyl)$_2$; —$SCF_3$; —$SCF_2H$; —$SCFH_2$; —S—$C_{1-6}$-alkyl; —S(=O)—$C_{1-6}$-alkyl; —S(=O)$_2$—$C_{1-6}$-alkyl; —S(=O)$_2$—OH; —S(=O)$_2$—O—$C_{1-6}$-alkyl; —S(=O)$_2$—$NH_2$; —S(=O)$_2$—NH($C_{1-6}$-alkyl); —S(=O)$_2$—N($C_{1-6}$-alkyl)$_2$; —$C_{3-6}$-cycloalkyl; 3 to 6-membered heterocycloalkyl; phenyl; 5 or 6-membered heteroaryl; —O—$C_{3-6}$-cycloalkyl; —O-(3 to 6-membered heterocycloalkyl); —O-phenyl; —O-(5 or 6-membered heteroaryl); —C(=O)—$C_{3-6}$-cycloalkyl; —C(=O)-(3 to 6-membered heterocycloalkyl); —C(=O)-phenyl; —C(=O)-(5 or 6-membered heteroaryl); —S(=O)$_2$—($C_{3-6}$-cycloalkyl); —S(=O)$_2$-(3 to 6-membered heterocycloalkyl); —S(=O)$_2$-phenyl or —S(=O)$_2$-(5 or 6-membered heteroaryl);

wherein aryl and 5 or 6-membered heteroaryl in each case independently from one another are unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —$C_{1-4}$-alkylene-$CF_3$; —$C_{1-4}$-alkylene-$CF_2H$; —$C_{1-4}$-alkylene-$CFH_2$; —C(=O)—$C_{1-6}$-alkyl; —C(=O)—OH; —C(=O)

—OC$_{1-6}$-alkyl; —C(=O)—NH(OH); —C(=O)—NH$_2$; —C(=O)—NH(C$_{1-6}$-alkyl); —C(=O)—N(C$_{1-6}$-alkyl)$_2$; —OH; =O; —OCF$_3$; —OCF$_2$H; —OCFH$_2$; —OCF$_2$Cl; —OCFCl$_2$; —O—C$_{1-6}$-alkyl; —O—C$_{3-6}$-cycloalkyl; —O-(3 to 6-membered heterocycloalkyl); —NH$_2$; —NH(C$_{1-6}$-alkyl); —N(C$_{1-6}$-alkyl)$_2$; —NH—C(=O)—C$_{1-6}$-alkyl; —N(C$_{1-6}$-alkyl)-C(=O)—C$_{1-6}$-alkyl; —NH—C(=O)—NH$_2$; —NH—C(=O)—NH(C$_{1-6}$-alkyl); —NH—C(=O)—N(C$_{1-6}$-alkyl)$_2$; —N(C$_{1-6}$-alkyl)-C(=O)—NH(C$_{1-6}$-alkyl); —N(C$_{1-6}$-alkyl)-C(=O)—N(C$_{1-6}$-alkyl)$_2$; —NH—S(=O)$_2$—C$_{1-6}$-alkyl; —SCF$_3$; —S—C$_{1-6}$-alkyl; —S(=O)—C$_{1-6}$-alkyl; —S(=O)$_2$—C$_{1-6}$-alkyl; —S(=O)$_2$—NH$_2$; —S(=O)$_2$—NH(C$_{1-6}$-alkyl); —S(=O)$_2$—N(C$_{1-6}$-alkyl)$_2$; —C$_{3-6}$-cycloalkyl; —C$_{1-4}$-alkylene-C$_{3-6}$-cycloalkyl; 3 to 6-membered heterocycloalkyl; —C$_{1-4}$-alkylene-(3 to 6-membered heterocycloalkyl); phenyl or 5 or 6-membered heteroaryl;

in the form of the free compound or a physiologically acceptable salt thereof.

2. The compound according to claim 1, wherein
X represents CR$_5$, Y represents CR$_6$; and Z represents CR$_7$; or
X represents N, Y represents CR$_6$; and Z represents CR$_7$; or
X represents CR$_5$, Y represents N; and Z represents CR$_7$; or
X represents CR$_5$, Y represents CR$_6$; and Z represents N; or
X represents N, Y represents N; and Z represents CR$_7$; or
X represents N, Y represents CR$_6$; and Z represents N; or
X represents CR$_5$, Y represents N; and Z represents N; or
X represents N, Y represents N; and Z represents N.

3. The compound according to claim 2, wherein optionally present R$_5$ represents —H; optionally present R$_6$ represents —H; and/or optionally present R$_7$ represents —H.

4. The compound according to claim 1, wherein R$_1$ represents —C$_{3-10}$-cycloalkyl; —C$_{1-6}$-alkylene-C$_{3-10}$-cycloalkyl; aryl; or 5 or 6-membered heteroaryl.

5. The compound according to claim 1, wherein R$_2$ represents —C(=O)—C$_{1-10}$-alkyl; —C(=O)—C$_{3-10}$-cycloalkyl; —C(=O)—C$_{1-6}$-alkylene-C$_{3-10}$-cycloalkyl; —C(=O)-(3 to 7 membered heterocycloalkyl); —C(=O)-(5 or 6-membered heteroaryl); —S(=O)$_2$—C$_{1-10}$alkyl; —S(=O)$_2$—C$_{3-10}$-cycloalkyl; —S(=O)$_2$—C$_{1-6}$-alkylene-C$_{3-10}$-cycloalkyl; or —S(=O)$_2$-(5 or 6-membered heteroaryl).

6. The compound according to claim 1, wherein R$_3$ represents 3 to 7 membered heterocycloalkyl; 5 or 6-membered heteroaryl; or —C$_{1-6}$-alkylene-(5 or 6-membered heteroaryl).

7. The compound according to claim 1, wherein R$_4$ represents —H.

8. The compound according to claim 1, wherein R$_1$ represents
cyclopropyl, unsubstituted;
—CH$_2$-cyclopropyl, unsubstituted;
phenyl, unsubstituted or mono- or disubstituted with substituents independently of one another selected from the group consisting of —F, —Cl, —Br, —CH$_3$, —CF$_3$, —CN, cyclopropyl and —OCH$_3$, wherein phenyl is optionally annealed to a dioxolane ring by a substituent —O—CH$_2$CH$_2$—O—; or
pyridyl, unsubstituted or mono- or disubstituted with substituents independently of one another selected from the group consisting of —F, —Cl, —Br, —CH$_3$, —CF$_3$, —CN, and —OCH$_3$.

9. The compound according to claim 1, wherein R$_2$ represents —C(=O)—C$_{1-10}$-alkyl, unsubstituted or mono- or disubstituted with substituents independently of one another selected from the group consisting of —F, —Cl, and —Br;
—C(=O)-cyclopropyl, unsubstituted or mono- or disubstituted with substituents independently of one another selected from the group consisting of —F, —Cl, —Br, —CH$_3$, —CF$_3$, —CN, and —OCH$_3$;
—C(=O)-cyclobutyl, unsubstituted or mono- or disubstituted with substituents independently of one another selected from the group consisting of —F, —Cl, —Br, —CH$_3$, —CF$_3$, —CN and —OCH$_3$;
—C(=O)-2-tetrahydrofuranyl, unsubstituted;
—C(=O)-(5- to 6-membered heteroaryl), wherein said 5- to 6-membered heteroaryl is selected from the group consisting of thiazolyl, pyrazolyl, oxazolyl and 1-oxa-2,4-diazolyl, 1,2,5-oxadiazolyl, isoxazolyl, isothiazolyl, wherein in each case said 5- to 6-membered heteroaryl is unsubstituted or mono- or disubstituted with substituents independently of one another selected from the group consisting of —F, —Cl, —Br, —CH$_3$, —CF$_3$, —CN, =O, and —OCH$_3$;
—S(=O)$_2$—C$_{1-10}$-alkyl, unsubstituted;
—S(=O)$_2$-cyclopropyl, unsubstituted;
—S(=O)$_2$—CH$_2$-cyclopropyl, unsubstituted; or
—S(=O)$_2$-(5- to 6-membered heteroaryl), wherein said 5- to 6-membered heteroaryl is selected from the group consisting of thiazolyl, pyrazolyl, oxazolyl and 1-oxa-2,4-diazolyl, 1,2,5-oxadiazolyl, isoxazolyl, isothiazolyl, wherein in each case said 5- to 6-membered heteroaryl is unsubstituted or mono- or disubstituted with substituents independently of one another selected from the group consisting of —F, —Cl, —Br, —CH$_3$, —CF$_3$, —CN, =O, and —OCH$_3$.

10. The compound according to claim 1, wherein R$_3$ represents piperidinyl, unsubstituted or substituted with —C(=O)-cyclopropyl;
5- to 6-membered heteroaryl selected from the group consisting of pyrazolyl, pyridyl, and pyrimidinyl, wherein in each case said 5- to 6-membered heteroaryl is unsubstituted or mono- or disubstituted with substituents independently of one another selected from the group consisting of —F, —Cl, —Br, —CH$_3$, —CF$_3$, —CN, =O, and —OCH$_3$; or
—CH$_2$-(5- to 6-membered heteroaryl) selected from the group consisting of —CH$_2$-pyrazolyl, —CH$_2$-pyridyl, and —CH$_2$-pyrimidinyl, wherein in each case said 5- to 6-membered heteroaryl is unsubstituted or mono- or disubstituted with substituents independently of one another selected from the group consisting of —F, —Cl, —Br, —CH$_3$, —CF$_3$, —CN, =O, and —OCH$_3$.

11. The compound according to claim 1, wherein
R$_1$ represents phenyl, unsubstituted or mono- or disubstituted with substituents independently of one another selected from the group consisting of —F, —Cl, —Br, —CH$_3$—CF$_3$, —CN, cyclopropyl and —OCH$_3$; and/or
R$_2$ represents —C(=O)—C$_{1-6}$-alkyl; —C(=O)-cyclopropyl; or —C(=O)-cyclobutyl, unsubstituted or mono- or disubstituted with substituents independently of one another selected from the group consisting of —F, —Cl, and —Br; and/or
R$_3$ represents N-methyl-2-oxo-pyridyl.

12. The compound according to claim 1 selected from the group consisting of

1 N-[(2R,3S)-2-(3-chlorophenyl)-1-[1-(1-methyl-6-oxo-3-pyridyl)indazol-5-yl]-5-oxo-pyrrolidin-3-yl]-2,2-difluoro-propanamide 2 2,2-difluoro-N-[rac-(2R,3S)-2-(2,4-difluorophenyl)-1-[1-(1-methyl-6-oxo-3-pyridyl)indazol-5-yl]-5-oxo-pyrrolidin-3-yl]propanamide 3 2,2-difluoro-N-[rac-(2R,3S)-2-(2,3-dihydro-1,4-benzodioxin-6-yl)-1-[1-(1-methyl-6-oxo-3-pyridyl)indazol-5-yl]-5-oxo-pyrrolidin-3-yl]propanamide 4 2,2-difluoro-N-[(2R,3S)-1-[1-(1-methyl-6-oxo-3-pyridyl)indazol-5-yl]-5-oxo-2-phenyl-pyrrolidin-3-yl]propanamide 5 2,2-difluoro-N-[(2R,3S)-2-(3-fluorophenyl)-1-[1-(1-methyl-6-oxo-3-pyridyl)indazol-5-yl]-5-oxo-pyrrolidin-3-yl]propanamide 6 2,2-difluoro-N-[(2R,3S)-2-(2-fluorophenyl)-1-[1-(1-methyl-6-oxo-3-pyridyl)indazol-5-yl]-5-oxo-pyrrolidin-3-yl]propanamide 7 2,2-difluoro-N-[rac-(2R,3S)-5-oxo-2-phenyl-1-[1-(3-pyridyl)indazol-5-yl]pyrrolidin-3-yl]propanamide 9 2,2-difluoro-N-[rac-(2R,3S)-1-[1-(5-fluoro-2-pyridyl)indazol-5-yl]-5-oxo-2-phenyl-pyrrolidin-3-yl]propanamide 13 5-methyl-N-[(2R,3S)-1-[1-(1-methyl-6-oxo-3-pyridyl)indazol-5-yl]-5-oxo-2-phenyl-pyrrolidin-3-yl]thiazole-2-carboxamide 15 2,2-difluoro-N-[(2R,3S)-2-(4-fluoro-3-methoxy-phenyl)-1-[1-(1-methyl-6-oxo-3-pyridyl) indazol-5-yl]-5-oxo-pyrrolidin-3-yl]propanamide 17 2,2-difluoro-N-[(2R,3S)-2-(4-fluorophenyl)-1-[1-(1-methyl-6-oxo-3-pyridyl)indazol-5-yl]-5-oxo-pyrrolidin-3-yl]propanamide 18 1-fluoro-N-[(2R,3S)-1-[1-(1-methyl-6-oxo-3-pyridyl)indazol-5-yl]-5-oxo-2-phenyl-pyrrolidin-3-yl]cyclopropanecarboxamide 22 2,2-difluoro-N-[rac-(2R,3S)-1-[1-(6-methoxy-3-pyridyl)indazol-5-yl]-5-oxo-2-phenyl-pyrrolidin-3-yl]propanamide 23 2,2-difluoro-N-[rac-(2R,3S)-5-oxo-2-phenyl-1-[1-(4-pyridyl)indazol-5-yl]pyrrolidin-3-yl]propanamide 24 2,2-difluoro-N-[rac-(2R,3S)-1-[1-(6-methyl-3-pyridyl)indazol-5-yl]-5-oxo-2-phenyl-pyrrolidin-3-yl]propanamide 25 2,2-difluoro-N-[rac-(2R,3S)-1-[1-(2-methyl-4-pyridyl)indazol-5-yl]-5-oxo-2-phenyl-pyrrolidin-3-yl]propanamide 26 1-methyl-N-[(2R,3S)-1-[1-(1-methyl-6-oxo-3-pyridyl)indazol-5-yl]-5-oxo-2-phenyl-pyrrolidin-3-yl]cyclopropanecarboxamide 27 2,2-difluoro-N-[rac-(2R,3S)-1-[1-(2-methoxy-4-pyridyl)indazol-5-yl]-5-oxo-2-phenyl-pyrrolidin-3-yl]propanamide 31 2,2-difluoro-N-[rac-(2R,3S)-1-[1-[(2-methoxy-4-pyridyl)methyl]indazol-5-yl]-5-oxo-2-phenyl-pyrrolidin-3-yl]propanamide 32 2,2-difluoro-N-[rac-(2R,3S)-1-[1-[(1-methylpyrazol-3-yl)methyl]indazol-5-yl]-5-oxo-2-phenyl-pyrrolidin-3-yl]propanamide 33 2,2-difluoro-N-[rac-(2R,3S)-1-[1-[(6-methoxy-3-pyridyl)methyl]indazol-5-yl]-5-oxo-2-phenyl-pyrrolidin-3-yl]propanamide 34 2,2-difluoro-N-[rac-(2R,3S)-1-[1-[(1-methyl-6-oxo-3-pyridyl)methyl]indazol-5-yl]-5-oxo-2-phenyl-pyrrolidin-3-yl]propanamide 35 2,2-difluoro-N-[rac-(2R,3S)-1-[1-[1-(cyclopropanecarbonyl)-4-piperidyl]indazol-5-yl]-5-oxo-2-phenyl-pyrrolidin-3-yl]propanamide 38 2,2-difluoro-N-[rac-(2R,3S)-1-[1-[(1-methyl-2-oxo-4-pyridyl)methyl]indazol-5-yl]-5-oxo-2-phenyl-pyrrolidin-3-yl]propanamide 39 N-[(2R,3S)-2-(2-fluorophenyl)-1-[1-(1-methyl-6-oxo-3-pyridyl)indazol-5-yl]-5-oxo-pyrrolidin-3-yl]cyclopropanecarboxamide 40 N-[rac-(2R,3S)-1-[1-[(2-methoxy-4-pyridyl)methyl]indazol-5-yl]-5-oxo-2-phenyl-pyrrolidin-3-yl]cyclopropanecarboxamide 41 N-[(2R,3S)-1-[1-(1-methyl-6-oxo-3-pyridyl)indazol-5-yl]-2-(o-tolyl)-5-oxo-pyrrolidin-3-yl]cyclopropanecarboxamide 42 2,2-difluoro-N-[(2R,3S)-2-(2-methoxy-4-pyridyl)-1-[1-(1-methyl-6-oxo-3-pyridyl)indazol-5-yl]-5-oxo-pyrrolidin-3-yl]propanamide 43 2,2-difluoro-N-[(2R,3S)-1-[1-(1-methyl-6-oxo-3-pyridyl)indazol-5-yl]-2-(o-tolyl)-5-oxo-pyrrolidin-3-yl]propanamide 44 N-[(2R,3S)-1-[1-(1-methyl-6-oxo-3-pyridyl)indazol-5-yl]-5-oxo-2-phenyl-pyrrolidin-3-yl]thiazole-4-carboxamide 45 1-methyl-N-[(2R,3S)-1-[1-(1-methyl-6-oxo-3-pyridyl)indazol-5-yl]-5-oxo-2-phenyl-pyrrolidin-3-yl]pyrazole-3-carboxamide 46 2,2-difluoro-N-[rac-(2R,3S)-1-[1-(1-methylpyrazol-4-yl)indazol-5-yl]-5-oxo-2-phenyl-pyrrolidin-3-yl]propanamide 47 2,2-difluoro-N-[rac-(2R,3S)-1-[1-(5-fluoropyrimidin-2-yl)indazol-5-yl]-5-oxo-2-phenyl-pyrrolidin-3-yl]propanamide 48 (R)—N-[(2R,3S)-1-[1-(1-methyl-6-oxo-3-pyridyl)indazol-5-yl]-5-oxo-2-phenyl-pyrrolidin-3-yl]tetrahydrofuran-2-carboxamide 49 N-[(2R,3S)-1-[1-(1-methyl-6-oxo-3-pyridyl)indazol-5-yl]-5-oxo-2-phenyl-pyrrolidin-3-yl]oxazole-2-carboxamide 50 N-[(2R,3S)-1-[1-(1-methyl-6-oxo-3-pyridyl)indazol-5-yl]-5-oxo-2-phenyl-pyrrolidin-3-yl]oxazole-4-carboxamide and 51 5-methyl-N-[(2R,3S)-1-[1-(1-methyl-6-oxo-3-pyridyl)indazol-5-yl]-5-oxo-2-phenyl-pyrrolidin-3-yl]-1,2,4-oxadiazole-3-carboxamide in the form of the free compound or a physiologically acceptable salt thereof.

13. A pharmaceutical dosage form comprising a compound according to claim 1.

14. A method for treatment of pain and/or inflammation in a subject, comprising a step of administering to the subject a compound according to claim 1.

15. A method for treatment of asthma, rheumatoid arthritis, inflammatory bowel disease, chronic obstructive pulmonary disease, acute respiratory distress syndrome, cystic fibrosis, osteoarthritis, polymyalgia rheumatica, giant cell arteritis, Sjögren syndrome, Duchenne muscular dystrophy, vasculitis, Behçet's disease, ulcerative colitis and/or Crohn's disease, comprising administering to a subject a compound according to claim 1.

* * * * *